(12) United States Patent
Zipper

(10) Patent No.: US 10,413,473 B2
(45) Date of Patent: Sep. 17, 2019

(54) SEXUAL STIMULATION DEVICE USING LIGHT THERAPY, VIBRATION AND PHYSIOLOGICAL FEEDBACK

(71) Applicant: Ralph Zipper, Melbourne, FL (US)

(72) Inventor: Ralph Zipper, Melbourne, FL (US)

( * ) Notice: Subject to any disclaimer, the term of this patent is extended or adjusted under 35 U.S.C. 154(b) by 290 days.

(21) Appl. No.: 14/681,943

(22) Filed: Apr. 8, 2015

(65) Prior Publication Data

US 2016/0000642 A1   Jan. 7, 2016

Related U.S. Application Data

(60) Continuation-in-part of application No. 14/456,151, filed on Aug. 11, 2014, now Pat. No. 9,610,214, (Continued)

(51) Int. Cl.
*A61H 19/00* (2006.01)
*A61N 5/06* (2006.01)
(Continued)

(52) U.S. Cl.
CPC .............. *A61H 19/34* (2013.01); *A61H 19/44* (2013.01); *A61H 23/0263* (2013.01); (Continued)

(58) Field of Classification Search
CPC .................... A61H 19/34; A61H 19/44; A61H 2201/0153; A61H 2201/10; A61H 19/40; (Continued)

(56) References Cited

U.S. PATENT DOCUMENTS 4,722,326 A    2/1988   Ruderian
5,067,480 A   11/1991   Woog
(Continued)

FOREIGN PATENT DOCUMENTS

DE     202009011528 U1    1/2010
WO     WO2011159906       12/2011

OTHER PUBLICATIONS

International Search Report, dated Nov. 6, 2013, ISA/US, Alexandria, Virginia, United States.
(Continued)

*Primary Examiner* — Christine H Matthews
(74) *Attorney, Agent, or Firm* — Stephen C. Thomas

(57) ABSTRACT

A sexual stimulation apparatus and method which may comprise a plurality of light sources for photostimulation of the vagina, clitoris, or both; a plurality of vibrators for mechanical stimulation of the vagina, clitoris, or both; a handle for ease of operation; a controller and programmable memory for containing modes of operation and driving the light sources and vibrators of the invention; a vaginal finger; a clitoral finger; a handle for ease of use; a keypad for user entry of commands; and a charging and programming port. The invention comprises sensors that sense physiologic parameters of a user and adjust sexual stimulation parameters to achieve a desired sexual stimulation effect. Blood oxygen level, temperature, pulse rate and muscle electrical activity may be sensed by the invention. The invention also comprises a flexible covering that provides smooth sliding engagement with the vagina and clitoris of a user.

11 Claims, 26 Drawing Sheets

Related U.S. Application Data which is a division of application No. 13/828,445, filed on Mar. 14, 2013, now Pat. No. 8,801,600.

(60) Provisional application No. 61/610,899, filed on Mar. 14, 2012.

(51) Int. Cl.
 *A61H 23/02* (2006.01)
 *A61H 23/00* (2006.01)

(52) U.S. Cl.
 CPC .......... *A61N 5/0624* (2013.01); *A61H 23/006* (2013.01); *A61H 2201/0153* (2013.01); *A61H 2201/10* (2013.01); *A61H 2201/501* (2013.01); *A61H 2201/5005* (2013.01); *A61H 2201/5015* (2013.01); *A61H 2201/5038* (2013.01); *A61H 2201/5061* (2013.01); *A61H 2201/5097* (2013.01); *A61H 2230/045* (2013.01); *A61H 2230/085* (2013.01); *A61H 2230/208* (2013.01); *A61N 2005/0611* (2013.01)

(58) Field of Classification Search
 CPC ............ A61H 23/00; A61H 2201/5061; A61N 2005/0611; A61N 5/0624; A61N 5/0622
 See application file for complete search history.

(56) References Cited

U.S. PATENT DOCUMENTS

| | | | |
|---|---|---|---|
| 5,336,159 A | 8/1994 | Cheng | |
| 5,925,002 A | 7/1999 | Wallman | |
| 6,110,102 A | 8/2000 | Harrison | |
| 6,190,307 B1 | 2/2001 | Tsai | |
| 6,741,895 B1* | 5/2004 | Gafni | A61B 5/4337 600/38 |
| 6,932,779 B2 | 8/2005 | Kasai | |
| 7,341,566 B2 | 3/2008 | Nan | |
| 7,419,475 B2 | 9/2008 | Ferber | |
| 7,749,178 B2 | 7/2010 | Imboden | |
| 7,815,582 B2 | 10/2010 | Imboden | |
| 2003/0199946 A1 | 10/2003 | Gutwein | |
| 2003/0232303 A1 | 12/2003 | Black | |
| 2005/0113725 A1 | 5/2005 | Masuda | |
| 2005/0197982 A1 | 8/2005 | Fox | |
| 2006/0069330 A1 | 3/2006 | Nan | |
| 2006/0084837 A1 | 4/2006 | Klearman | |
| 2006/0135892 A1 | 6/2006 | Nan | |
| 2007/0149903 A1 | 6/2007 | Nan | |
| 2008/0071138 A1 | 3/2008 | Mertens | |
| 2008/0091127 A1 | 4/2008 | Nan | |
| 2008/0119767 A1 | 5/2008 | Berry | |
| 2008/0139980 A1 | 6/2008 | Fladl | |
| 2008/0306417 A1 | 12/2008 | Imboden | |
| 2009/0099413 A1 | 4/2009 | Kobashikawa | |
| 2009/0093673 A1 | 9/2009 | Lee | |
| 2010/0174136 A1 | 7/2010 | Shim | |
| 2010/0268021 A1 | 10/2010 | Standfest et al. | |
| 2011/0034837 A1 | 2/2011 | Lee | |
| 2011/0071445 A1 | 3/2011 | Imboden | |
| 2011/0098613 A1 | 4/2011 | Thomas | |
| 2011/0105837 A1 | 5/2011 | Lee | |
| 2011/0124959 A1 | 5/2011 | Murison | |
| 2011/0218395 A1* | 9/2011 | Stout | A61F 5/00 600/38 |
| 2011/0224584 A1 | 9/2011 | Pryor | |
| 2011/0319707 A1 | 12/2011 | Mertens | |
| 2012/0215141 A1 | 8/2012 | Peddicord | |
| 2012/0220907 A1 | 8/2012 | Zinn | |
| 2012/0291208 A1 | 11/2012 | Edwards | |

OTHER PUBLICATIONS

International Preliminary Report on Patentability, dated Jan. 28, 2014, ISA/US, Alexandria, Virginia, United States.
Written Opinion of the International Searching Authority, dated Jun. 11, 2013, ISA/US, Alexandria Virginia, United States.
Non-Final office action, U.S. Appl. No. 13/828,445, dated Nov. 12, 2013, Alexandria Virginia, United States.
European Search Report, dated Apr. 13, 2015, European patent office 80298 Munich Germany.

\* cited by examiner

Fig. 9

Exemplary Vibration Patterns

| Description | Vibrator State |
|---|---|
| Constant ("C") | Vibrator on at constant power level |
| In Phase Pulse ("IPP") | Vibrator on for 0.4 seconds and off for 0.4 seconds |
| Out of Phase Pulse ("OPP") | Vibrator off for 0.4 seconds and on for 0.4 seconds |
| In Phase Wave ("IPW") | Vibrator intensity modulated as a sine wave with a 1.2 second period in phase as between vaginal and clitoral vibrators |
| Out of Phase Wave ("OPW") | Vibrator intensity modulated as a sine wave with a 1.2 second period out of phase as between vaginal and clitoral vibrators |
| Fast Pulse ("FP") | Vibrator on for 0.2 seconds and off for 0.2 seconds |

Fig. 10

Exemplary Mode of Operation

| | Elapsed Time (sec) | 0-60 | 60-180 | 180-300 | 300-480 | 480- |
|---|---|---|---|---|---|---|
| Vaginal Finger | LED Pattern | PW1 | PW2 | PW3 | PW4 | PW4 |
| | Vibrator Pattern and Intensity | C LOW | C MEDIUM | IPW MEDIUM | IPW HIGH | C MEDIUM |
| Clitoral Finger | LED Pattern | LSO 1 | LSO 2 | LSO 3 | LSO 4 & 5 | LSO 4 & 5 |
| | Vibrator Pattern and Intensity | C LOW | C MEDIUM | OPW MEDIUM | OPW HIGH | C MEDIUM |

Fig. 11

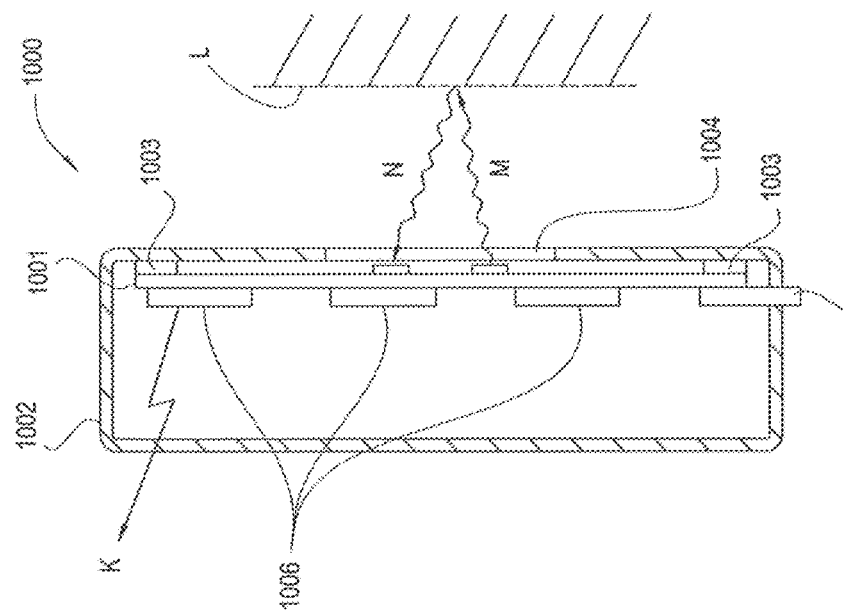
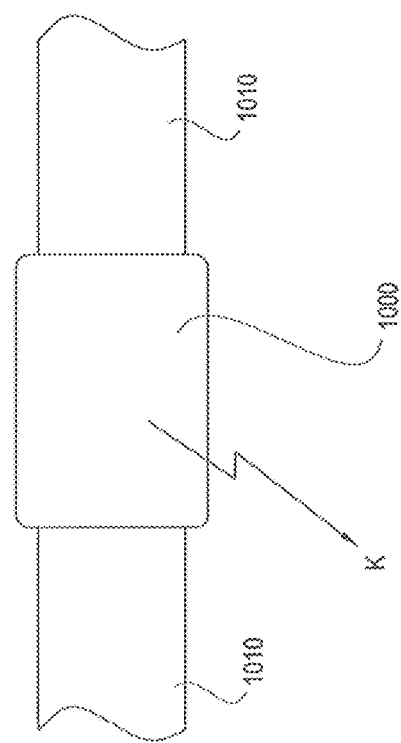
Fig. 19b
Fig. 19a

SEXUAL STIMULATION DEVICE USING LIGHT THERAPY, VIBRATION AND PHYSIOLOGICAL FEEDBACK

CROSS REFERENCE TO RELATED APPLICATIONS

This application is a continuation-in-part (CIP) application of non-provisional application Ser. No. 14/456,151, filed Aug. 11, 2014, which is herein incorporated by reference in its entirety and which is a divisional of non-provisional application Ser. No. 13/828,445 filed Mar. 14, 2013 which is also incorporated herein by reference in its entirety and which was a non-provisional patent application claiming the benefit of provisional application Ser. No. 61/610,899 filed with the United States Patent and Trademark Office on Mar. 14, 2012, which is also herein incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The improved sexual stimulation device of the invention relates generally to the field of female sexual stimulation devices, more specifically, handheld sexual stimulation devices using vibration stimulation, light energy stimulation, and biological feedback in combination in order to achieve sexual stimulation of a user.

2. Background Art

A variety of handheld sexual stimulating devices have been described in the art, many of which are commercially available, and some of which have been the subject of patents. The devices of the prior art may combine mechanical stimulation such as vibration with another form of stimulation, such as heat, to achieve a sexually stimulating effect for a user.

However, it would be desirable for a user's physiologic response to sexual stimulation to be used as feedback in order to improve the stimulation experience. None of the sexual stimulation devices of the prior art combine the use of physiological feedback, therapeutic light energy for photo-stimulation and/or photo-biomodulation and/or mechanical stimulation in a single apparatus which provides multiple modes of use including programmable mechanical stimulation and light energy control, multiple frequencies of light energy, at least one mechanical stimulators, which may be a source of vibration, a plurality of therapeutic light sources which may illuminate body tissue and may thereby increase blood flow, improve tissue health, and decrease microbes and therefore improve sexual stimulation and genital health; and a plurality of pre-programmed modes of operation. None of the devices of the prior art utilize physiological sensors to monitor the physiologic parameters of a user and changes thereto that are experienced while a user is using the device for sexual stimulation; nor do the aforementioned devices utilize data provided by physiological sensors to change at least one parameter of sexual simulation being applied to a user's body by the sexual stimulation device, or alert the user of such physiologic states and or changes thereto.

"Mechanical stimulation", as used herein, is defined as mechanical manipulation of a body surface that is perceivable by a user wherein said mechanical manipulation may be achieved by any means including but not limited to vibration, sonic pulses, rubbing, tapping, application of pressure to a body surface of a user, application of pressure to a body surface of a user that varies in intensity, and any other form of mechanical manipulation of surface body tissue in a perceptible manner.

"Therapeutic light", as used herein, refers to any light, visible or not visible, that exerts an effect to the biologic or chemical status of the tissue or microbe to which it is applied, with such effect or effects being other than that of the activation or modification photosensitive receptors of the human eye. Examples of therapeutic effects may include but not be limited to alteration of cellular respiration, alteration or activation of enzyme or enzyme pathways, alteration in mitochondrial activity, the production or reduction in adenosine triphosphate or similar molecules, the production or reduction of nitric oxide or similar chemicals, changes in blood pressure, muscle relaxation, muscle contraction, cellular activation, modification of the inflammatory response, modification of the healing response, hastening of microbe activity, alteration of microbe activity, and microbe death. Therapeutic light may be referred to as photostimulation when the effects of said light are stimulating in nature. Therapeutic light may be referred to as photomodulation or photobiomodulation when the effects of said light are other than stimulatory or beyond stimulatory.

"Physiological feedback" as used herein means the use of measured heart rate information, measured temperature information, electrical activity of muscles as measured by electomyographic means, or measured blood oxygen saturation of hemoglobin of a user as input information for determining at least one parameter of sexual simulation being applied to a user's body.

"Physiologic parameters" as used herein means heart rate; temperature blood oxygenation saturation of hemoglobin, or simply "blood oxygen saturation"; blood pressure, secretion of fluids, or electrical activity of muscles as measured by electomyographic means.

"Parameter of sexual stimulation" as used herein means the intensity or pattern of mechanical stimulation applied to the user by the invention or the pattern of mechanical stimulation applied to the user by the invention from any of the sources of mechanical stimulation, individually; the intensity, frequency or pattern of light stimulation applied to the user by the invention or the pattern of light stimulation applied to the user by the invention from any of the sources of light stimulation, individually; an audio signal produced be the invention, or any combination of these.

"Physiologic sensor", "sensor" or "sensors", as used herein, are defined as devices capable of sensing any of the physiologic parameters of a user and providing a sensor signal representing a sensed physiologic parameter to a controller capable of executing computer readable instruction. "Physiologic sensor", "sensor" or "sensors" may include but is not limited to pulse oximeters, digital temperature sensors, EMG sensors, heart rate sensors, or sensors that measure secretions, in any combination.

"Physiologic state", as used herein, refers to a user presenting with a predetermined range of at least one physiologic parameter.

Vibrators, personal message devices, and other adult toys which comprise the general category of sexual stimulation devices are typically used to create a sexual response in a user. The sexual responses of humans are divided into four sequential stages known as the sexual response cycle. These stages are known as the Excitement Phase, Plateau Phase, Orgasmic Phase, and Resolution phase. Each phase is defined by alteration or changes in physiologic parameters of a subject. During the Excitement Phase, blood flow increases and vasocongestion occurs. In female subjects there is often a tightening of the vaginal opening and an increase in secretion or lubrication. In male subjects, the erection of the penis and upward movement of the testes occur. In both male and female subjects there may be an increase in respiration, heart rate, and changes in blood oxygen saturation of hemoglobin. During the Plateau Phase both male and female subjects typically experience further muscle tightening, increases in respiration and heart rate and changes in blood oxygen saturation of hemoglobin. Male subjects may experience rhythmic contraction of pelvic musculature. Female subjects may experience an increase in lubrication or secretion and further pelvic muscle tightening. The Orgasmic Phase is often associated with further increases in respiration, heart rate, and secretions. Both male and female subjects often experience rapid muscle contractions in pelvic musculature including muscle surrounding the vagina and anus. It is during this phase that male subjects ejaculate. The Resolution Phase is characterized by muscle relaxation, decreased blood pressure, and decreases in heart rate and respiration rate, and changes in hemoglobin oxygen saturation. Male subjects experience a loss of erection. Changes in blood pressure are also common in each phase of the sexual response cycle.

Users of vibrators, personal massagers or other sexual stimulation devices of the prior art must consciously monitor their own physiologic states in order to determine if and when to change the mode of use at least one parameter of sexual simulation being applied to a user's body by the sexual stimulation device. One example of such user-monitoring is a typical case in which a user senses that their muscles are becoming tighter, or that lubrication is increasing, whereupon the user may decide to reduce or increase the intensity of vibration produced by a vibrating sexual stimulation device. As another example, a user may make a decision to change the rate or intensity of a vibrating sexual stimulation device if the user senses their heart rate is increasing or decreasing during stimulation. These are but two examples of many in which a user may sense their own biological condition and use the sensed condition to make a decision as to how to vary at least one parameter of sexual simulation being applied to a user's body by the sexual stimulation device to achieve a desired effect. However, this prior art method of effecting volitional changes in at least one parameter of sexual simulation being applied to a user's body by a sexual stimulation device by depressing a button or other control interface on the sexual stimulation device based upon subjective assessment of physiologic condition by the user may be improved upon.

One drawback with the prior art method described above is that it requires mental concentration by a user during sexual stimulation by a sexual stimulation device; however, this mental concentration may act to reduce the effect of the stimulation because, generally, it is desired that a user remain mentally relaxed in order to achieve maximum effects of sexual stimulation. Another drawback of the prior art method described above is that user assessments of physiologic conditions by simple feeling are subjective. Such feelings are not objective measurements of the actual physiological conditions of a user of a sexual stimulation device. The subjective assessments made by the user are thus prone to error and misinterpretation, leading to decisions on the part of the user to vary at least one parameter of sexual simulation being applied to a user's body by the sexual stimulation device in a non-optimum manner. Additionally, the prior art method described above requires the user to be distracted, at least momentarily, to interact with the control interface of the device.

Users of vibrators, personal massagers or other adult devices presently in the art must consciously monitor their own physiologic states in order to determine if and when to change the behavior of such a device. In one example of such a user feeling that their muscles are getting tighter or lubrication is increasing may decide to slow down or increase the intensity of vibration associated with a vibrating device. In another example the user may make a decision to change one or more parameter(s) of sexual stimulation of the device if that user feels their heart rate is increasing or decreasing. This method of effecting volitional changes in the device behavior with button pushes or similar based upon subjective assessment of physiologic states is flawed. One problem with this method is that it requires a certain level of mental concentration by the user in a situation that would otherwise demand mental relaxation. Another problem is that subjective assessments of physiologic states are not objective data collections and, as such, are prone to error. Additionally, this method requires the user to be distracted, at least momentarily, to interact with the control interface of the device.

What is needed in the art, then, is a sexual stimulation device that is adapted to provide physiological feedback during use by a user, so that at least one parameter of sexual simulation being applied to a user's body by the sexual stimulation device can be varied, or changed, to achieve a desired simulation effect based on a variance between at least one sensed physiologic parameter and at least one predetermined physiologic parameter.

Applicant's invention, described and claimed herein, which, in part, utilizes physiological feedback to affect changes to the mode of operation of the sexual stimulation device, solves the aforementioned problems and therefore provides a significant improvement and inventive step over the state of the art.

BRIEF SUMMARY OF THE INVENTION

The present invention comprises a system and method that has one or more of the following features and/or steps, which alone or in any combination may comprise patentable subject matter.

A sexual stimulation device and method of the invention may comprise at least one physiologic sensor to monitor at least one physiologic parameter of a user and changes thereto while the user is using the device for sexual simulation and is experiencing one or more of the phases of sexual arousal. The device and method of the invention may utilize physiological information provided by said at least one physiologic sensor to be compared to a predetermined value for that physiologic parameter for the purpose of computing a variance between the predetermined value and the sensed value, and to change at least one parameter of sexual simulation being applied to a user's body by a sexual stimulation device in response to the variance, in order, for example, to achieve a desired sexual stimulation effect on the user, without direct input from the user. This not only frees the user of the duty of self-monitoring of the their physiologic parameters and removes the errors associated with subjective measurements of physiologic parameters by a user, but may allow the user to experience a journey through the sexual response cycle without the need to provide user input to the device. Additionally, the device and method of the invention may utilize internal memory, such as non-transitory computer readable memory, not only to initiate preprogrammed changes in at least one parameter of sexual simulation being applied to a user's body by a sexual stimulation device based on at least one of the user's sensed physiologic parameters, but the device and method of the invention may also use such memory to store self-initiated changes of at least one parameter of sexual simulation being applied to a user's body by the sexual stimulation device for future recall and use. In one example of this later memory function, a user may use physiologic parameter information provided by the at least one physiologic sensor to effect a change at least one parameter of sexual simulation being applied to a user's body by a sexual stimulation device. If the user finds that such changes result in a better user experience, the user may opt to save such changes to non-transitory computer readable or other memory. At time of subsequent use, the user may opt to utilize read the stored changes from memory and command the device to initiate such changes automatically during use by the user.

In accordance with one embodiment of the improved sexual stimulation device and method of the invention, the invention may comprise mechanical stimulation means, which may be vibrating sexual stimulation provided by a source of mechanical vibration such as an offset motor vibrator; and may further comprise therapeutic light simulation, which may be one or more therapeutic light sources such as Light Emitting Diodes or lasers; and may further comprise at least one physiologic sensor to monitor a user's physiologic state and changes thereto while the user is using the device for sexual simulation.

In accordance with an alternate embodiment of the invention, the device and method of the invention is a sexual stimulation device for male use which may comprise a light source for increased stimulation and/or therapeutic effect; mechanical stimulation such as an offset motor vibrator; and may optionally comprise at least one physiologic sensor to monitor a user's physiologic state and changes thereto while the user is using the device for sexual simulation.

In the prior art, female sexual stimulation devices have been designed to vibrate and stimulate the nerves of sexually sensitive areas of the female anatomy, for instance the clitoris or Gräfenberg Spot (G-spot). Although effective, this method of stimulation typically bypasses or rapidly moves through one of the most important phases of the sexual response cycle which is the arousal phase. This phase, also known as the excitement phase, is characterized by increased blood flow to the clitoris and vagina as well as an increase in muscle tone to the vagina and anus. The present invention may utilize therapeutic light energy to enhance genital blood flow. The ability of specific wavelengths of light to stimulate blood flow through the application of light energy is well established throughout medical literature. The application of light energy to certain parts of the body may improve blood flow and may therefore improve sexual response with or without a partner Improved blood flow can also extend a woman's sexual lifespan. The device and method of the invention may cause greater clitoral swelling and signs of improved genital blood flow, which may result in enhanced or more frequent orgasms (or both). Additionally, the present invention may utilize specific wavelengths of therapeutic light to decrease vaginal and vulvar bacteria and fungi populations. The medical and environmental literature is replete with data demonstrating specific wavelengths of light to be bactericidal, bacterostatic, fungicidal and fungistatic. The application of such light energy to the vagina, vulva, clitoris, and penis may reduce bacterial and fungal infections that may be caused by the use of stimulating devices or exist unrelated to such.

A preferred physical embodiment of the apparatus of the invention comprises a handle portion which may house control elements such as buttons, switches and the like; a vaginal finger which may contain at least one vibrator and at least one light source for insertion into the vagina of a female user; and a clitoral finger which may contain at least one vibrator and at least one light source for application to the clitoris of a female user. The vaginal finger may be adapted to directly apply mechanical stimulation such as vibration and light stimulation on or near the Gräfenberg Spot, or G-spot, of a female user; and the clitoral finger may be adapted to directly apply mechanical stimulation such as vibration and light stimulation on or near the clitoris of a user. In this manner, vibration and light stimulation are directly applied to the areas of the female anatomy known to result in maximum arousal and sexual stimulation. The improved sexual stimulation device and method of the invention may be used in numerous orientations and modes which are limited only by the imagination of the user or the user's partner, and are therefore not to be limited by the best mode described herein. Although the preferred embodiments combine therapeutic wavelengths of light with mechanical stimulation in the form of vibration, for instance offset vibrator motors, other forms of mechanical stimulation such as that used in neck massagers and massaging chairs may also comprise the invention.

In yet a further embodiment, the invention may comprise a handle portion which may house control elements such as buttons and switches, and sensor elements such as accelerometers, temperature sensors, and other environmental sensors known in the art; and at least one finger projecting from said handle comprising at least one means of mechanical stimulation such as an offset vibrator motor. The at least one finger may further comprise physiological sensor elements. Sensor elements in the handle or at least one finger may be in electrical communication either directly or indirectly with a controller which may be a microprocessor, microcontroller, or other controller capable of executing computer readable instructions as is known in the electrical arts. Sensor elements in the handle or at least one finger may also be in direct or indirect electrical communication with a serial peripheral interface bus which is also in communication with said controller. The controller may also be in electrical communication with the sexual simulation elements of the invention, thus allowing control of at least one parameter of sexual simulation being applied to a user's body by the sexual stimulation device. The invention may further comprise an alerting element capable of generating a visual, tactile, vibrotactile or auditory alert. Said alerting element may also be in electrical communication with the controller or sensors, or both, of the invention, either directly or indirectly. Thus the alerting element may provide auditory, visual, tactile, vibrotactile or other alerts based upon the status or changes in the status at least one parameter of sexual simulation being applied to a user's body by the sexual stimulation device; a measured physiological parameter of a user; or other information as may be pre-determined. The device and method of the invention may utilize physiological sensors to monitor physiologic parameters of the user during sexual stimulation by the sexual stimulation device, and, using these measured physiologic parameters, the controller of the invention may control the sexual stimulation elements of the invention to vary at least one parameter of sexual simulation being applied to a user's body by the sexual stimulation device in order to achieve a desired effect on the user. The invention may utilize the measured data from said at least one physiologic sensor to alert the user of specific physiologic parameters and/or changes thereto. This not only frees the user of the duty of self-monitoring of their physiologic state and removes the errors associated with such subjective measurements, but this also allows the user to experience a journey through the sexual response cycle without the need to provide user input to the device. Additionally, the claimed invention may utilize internal non-transitory computer readable memory in electrical communication with a microprocessor, firmware controller, programmable logic, or other circuitry that is able to execute program instructions to contain instructions not only to control at least one parameter of sexual simulation being applied to a user's body by the sexual stimulation device based on measured physiologic parameters, but may also use such non-transitory computer readable memory to store user-initiated changes in at least one parameter of sexual simulation being applied to a user's body by the sexual stimulation device for future use. In one example of storing of device-initiated changes in at least one parameter of sexual simulation being applied to a user's body by the sexual stimulation device related to measured physiologic conditions, a user may use alert information provided by the at least one physiologic sensor to make changes in at least one parameter of sexual simulation being applied to a user's body by the sexual stimulation device. If the user finds that such changes in at least one parameter of sexual simulation being applied to a user's body by the sexual stimulation device resulted in a more desirable user experience, the user may store, or save, such changes to the non-transitory computer readable memory of the invention. During subsequent use of the invention, the user may opt to recall and utilize such stored changes in at least one parameter of sexual simulation being applied to a user's body by the sexual stimulation device by utilizing the control interface of the invention to cause the invention to access the stored changes and cause the controller to initiate such changes automatically. In one example of such use of stored changes, the stored changes may be stored in such a manner as to be commanded when a specific measured physiological parameter of a user reaches a pre-determined threshold level.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating the preferred embodiments of the invention and are not to be construed as limiting the invention. The drawings of the various figures may not be to scale and some features may be exaggerated or minimized in order to clearly describe the invention. In the drawings:

FIG. 9 depicts exemplary light source patterns for an exemplary embodiment of the invention which comprises light source groups having a blue light source, a red light source, and a near infrared light source.

FIG. 10 depicts exemplary vibrator patterns for an exemplary embodiment of the invention having a vaginal finger vibrator and a clitoral finger vibrator.

FIG. 11 depicts a table of preferred modes of vibration and light stimulation for a preferred embodiment of the improved stimulation sexual device of the invention.

FIG. 19A depicts a front view of the optional spring-clip pulse oximeter sensor of the invention which may be, but is not necessarily, attached to a belt to be worn on the abdomen of a user.

FIG. 19B depicts a cross sectional view of the optional spring-clip pulse oximeter sensor of the invention which may be, but is not necessarily, attached to a belt to be worn on the abdomen of a user.

DETAILED DESCRIPTION OF THE INVENTION

Figure 1:
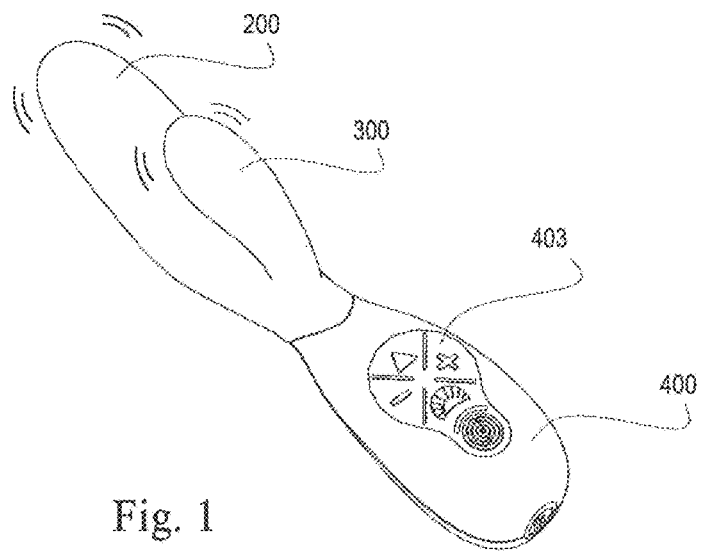
FIG. 1 depicts a perspective front view of a first physical embodiment of the sexual stimulation device of the invention.

The following documentation provides a detailed description of the invention.

The invention is a device primarily intended for sexual stimulation of a female user. The improved sexual stimulation device of the invention may comprise a vaginal finger which may further comprise at least one therapeutic light source and a means for mechanical stimulation, which may comprise a vibrator; a clitoral finger which may further comprise at least one therapeutic light source and a means for mechanical stimulation, which may comprise a vibrator, and a handle which may comprise a keypad, controller, and a battery. The apparatus of the invention may use mechanical stimulation which may also be combined with a therapeutic light source or multiple therapeutic light sources so that, when applied to the body of a user it provides a therapeutic effect on the tissue of the vagina, and or vulva and or clitoris as described below.

The light source or light sources of the invention may be automatically powered when the mechanical energy element of the invention is powered to an ON state, or may be configured so as to operate independently from the source or sources of mechanical energy of the invention. At least one light source, but preferably a plurality of light sources, may provide light energy that exits the device at one or more points, preferably at a point along the length of the vaginal finger and also at a point along the length of the clitoral finger, which may irradiate the tissue in the vagina and may irradiate the body of the user on or near the clitoris or vulva. A preferred embodiment of the improved sexual stimulation device of the invention may comprise both a vaginal vibrator and a clitoral vibrator. The vaginal vibrator and clitoral vibrator may comprise any vibrating element small enough to fit within the envelope of vaginal and clitoral fingers of the invention. In a preferred embodiment, the vaginal vibrator and clitoral vibrator may be defined as a DC motor with offset weights mounted on the motor shaft such that the center of mass of the weight is offset from the axis of rotation of the motor. When such motors are powered to an on state, a vibration results from the offset nature of the center of mass of the weight mounted onto the vibrator motor shaft. While the vibrators of the preferred embodiment may exhibit any rate of vibration, a preferred range of vibration rate is 5,000 to 25,000 rpm. Such offset vibration motors are well known in the art for use as sources of vibration. One such vibration motor is supplied by Shenzhen Kinmore Motor Co. of Guangdong, China, part number FF-N20VA-09170 R6x4.8. However, any small source of vibration or mechanical energy may be used as the vibration elements of the invention. For instance, sonic pulses have been shown to have a vibratory effect, and may be used as a vibration source in either the vaginal finger, the clitoral finger (for those embodiments that comprise a clitoral finger), or both. An alternate embodiment of the invention may thus use at least one sonic pulse generator as a source of vibration; or, alternatively, may comprise mechanical stimulation means that produce other forms of mechanical stimulation such as, for example, rubbing, tapping, pressure, or pressure that varies with time. Any combination of these mechanical stimulation means may comprise the invention.

The invention may emit therapeutic light energy that irradiates the areas of the Gräfenberg Spot inside the user's vagina, and may also irradiate the area on or near the clitoris and or elsewhere on the vulva or perineum. As used herein, the terms "the area of the Gräfenberg Spot" means the Gräfenberg Spot and the area of the user's tissue surrounding the Gräfenberg Spot extending outward from the Gräfenberg Spot for two inches. The Gräfenberg Spot, often called the G-Spot, is defined as a bean-shaped area of the vagina. Some women report that it is an erogenous zone which, when stimulated, can lead to strong sexual arousal, powerful orgasms and female ejaculation. The G-Spot is typically described as being located one to three inches (2.5 to 7.6 cm) along the front (anterior) vaginal wall between the vaginal opening and the urethra, and two inches wide, and is a sexually sensitive area. It is one objective of the invention to irradiate the G-spot, and the area in proximity to the G-spot, of a user's body with light energy; it is another object of the invention to provide mechanical stimulation to the G-spot, and the area in proximity to the G-spot, of a user's body. The emitted light energy may also be directed through a broader or de-focused beam to surrounding tissues of the vagina. The concentration or de-focusing of light energy on specific areas such as the Gräfenberg Spot or clitoris may be achieved by varying the placement of the light energy exit points of the invention, which may be a single or a plurality of exit points, and which may be covered by a wavelength transparent material, at appropriate positions on the apparatus in order for the exiting light energy to impact the intended area or areas. Similar alterations in light projection may be created by placing a lens or lenses over the light source or sources.

The light energy delivered by the device may be within a plurality of different ranges of wavelength. The light sources of the invention may be any light source such as Light Emitting Diode (LED), laser diode, organic LED (OLED) or any other light source which is compact enough to be enclosed in the apparatus. The wavelength of the light source, or sources, of the invention may be any wavelength, but is preferably in the range from 400 nm to 1000 nm. A plurality of light sources, which may be of different wavelengths, may be utilized; it is not necessary that a single source be used or that each of a plurality of sources emit light of the same wavelength. A preferred embodiment utilizes a plurality of light sources that, taken together, enables the invention to emit more than one wavelength range of light energy. The light energy used may be such to limit therapeutic penetration to less than 5 mm from the tissue surface and to have greater than 50% drop off of energy beyond such depth because the intended nerves and vessels that are the subject of stimulation are essentially superficial. Light energy may be delivered in continuous or pulsed form, where the pulses may take any shape and be of any duration. The power level of the light energy emitted by the light sources of the invention may be modulated in any fashion such as, for example, pulse width modulation, but preferably is controlled by increasing or decreasing the electrical current through the light source. "Light source" as used herein means a device that converts electrical energy to light energy such as an LED, OLED semiconductor laser, or any other device that exhibits this characteristic.

More specifically, a preferred embodiment of the improved sexual stimulation device of the invention comprises more specific ranges of bandwidth and output power of the light sources which are now described. The selection of bandwidth and output power of the therapeutic light sources for this preferred embodiment is based upon the demonstrated effects of photo-stimulation or photo-biomodulation. It has been demonstrated that light sources emitting energy in the infrared and near infrared spectrum may provide photo-stimulation and photo-biomodulation for the temporary relief of minor muscle and joint pain, muscle spasm, pain and stiffness, by promoting relaxation of the muscle tissue and temporarily increasing local blood circulation. As used herein, the term "light therapy" refers to the use of one or more light sources of any type that emits light with a wavelength between about 400 and 1000 nm.

Light therapy induces a variety of photo-thermal and photo-chemical processes in the body. Infrared light, near infrared light, and red light affect cellular mitochondria and activate surrounding enzymes resulting in the release of Nitric Oxide, ATP, and trigger photo neurological responses which result in changes in local pressure, temperature and permeability of cellular membranes, and stimulation of the immune, lymphatic and vascular systems. Organic nitrates are used every day in emergency rooms around the world to improve blood flow to the heart. There is also an inverse relationship between nitric oxide pathways and atherosclerosis. Patients with impaired NO pathways seem to have higher amounts of blood vessel plaques (narrowed blood vessels with poor blood flow and oxygen delivery to tissues). Over time, improved NO pathways may decrease atherosclerosis and create healthier "younger" blood vessels. Within the 400 to 1000 nm range is therapeutic blue light. Blue light energy has a bactericidal and bacteriostatic effect and has been shown to kill and disrupt growth of pathogenic bacteria. This inactivation mechanism, known to be oxygen dependent, is thought to be a result of the photo-excitation of naturally occurring endogenous porphyrins, which act as endogenous photosensitizers within the bacterial cells. This porphyrin excitation leads to energy transfer and, ultimately, the production of highly cytotoxic, oxygen-derived species, most notably, singlet oxygen. Although ultraviolet light is also lethal to many pathogenic bacteria, as we know, UV light is very detrimental to the skin. Blue light is much safer. Over time, blue light can safely lead to a reduction in pathogenic bacteria on skin and mucous membrane surfaces. Near IR light, also within this preferred spectrum of therapeutic light, damages the genetic material inside of fungus (DNA). DNA damage leads to impaired fungal growth. Over time the yeast population on skin and mucous membranes decreases. The use of IR light to treat toe nail fungus is now common medical practice.

Wavelength and power density are the two most prominent factors that determine the effectiveness of a light therapy source. The wavelength of the light source determines the absorption rate and penetration depth of the light energy in biological tissue. The power density of the light source, in combination with its wavelength, determines the effect the emitted light produces on body tissue, bacteria, and fungi. The effects of light therapy with therapeutic light have been studied for applications in, for example, pain relief and tissue healing: in, fact, about 2,700 clinical reports have been published in peer reviewed technical journals or conference proceedings with more than 70% of the reports indicating that light therapy is effective for tissue healing and pain relief. Clinical reports demonstrate that light therapy is effective, for instance, for the relief of muscle and joint pain, muscle spasm, pain and stiffness associated with arthritis, by promoting relaxation of the muscle tissue and temporarily increasing local blood circulation, without side effects. An even greater amount of data exist for the effects of light on bacteria and fungi.

It has also been shown that various pulse formats have a positive effect on photo-stimulation. Off-times between light pulses of 50 ms to 500 ms may have the greatest effect on cell organelles and plasma membranes. It is postulated that when this range of pulse formats is used, the re-oxidation of cytochrome c oxidase is optimized. This optimization leads to increase energy in the cell leading to improved blood flow and tissue repair. Pulsing of the light source is used to optimize the photo-biological response though a temporal optimization as well as dosage control. Optimal dosages of light range from of 0.001 J/cm$^2$ up to 3000 J/cm$^2$. These dosages can be controlled through changing the intensity of the light source, changing the irradiation time, and by light source pulse shape and timing. Therapeutic results can be seen using intensities ranging from 0.001 W/cm$^2$ to 100 W/cm$^2$.

Studies have concluded that photo-stimulation can increase blood flow. Increased blood flow is critical for bodily functions and is an important factor in the excitement phase of sexual stimulation. Photo-stimulation enhances vasodilatation and proliferation of the microvasculature as well as increases the level of oxygen content to tissue of the irradiated area, in this case, the G-spot area, and the area surrounding the clitoris. In a recent study which compared a photo-stimulated group of human test subjects to a non-photo-stimulated group of human test subjects, the photo-stimulated group increased blood flow to the exposed area for over 12 hours. This study showed the capillaries of the human subjects were enlarged and thus blood flow increased as a result of photo-stimulation. Photo-stimulation activates the powerhouse for the cell to increase the rate at which it produces energy. This activation increases the production of critical biochemical substances such Nitric Oxide (NO) and Vascular Endothelial Growth Factors (VEGF). These growth factors also promote new blood vessel growth. These biological responses to light therapy explain why photo-stimulation can have both an immediate and cumulative effect on a subject's level of sensation during sexual stimulation. As noted above, it has also been shown in laboratory studies that light energy in certain bandwidths may also have an anti-bacterial effect. Clinical studies have verified this anti-bacterial effect on patients for light sources between 405 nm and 420 nm. It has also been shown that a combination of blue and red output from LEDs can be a very effective treatment of both inflammation and antibacterial results. Recent studies have shown that blue LEDs irradiating the skin may result in a seven to fifteen times increase in the NO level in tissue as deep as 18 mm below the skin's surface.

Based on the effects of light therapy on human tissue, it is a feature of a preferred embodiment of the invention that blue light sources emitting light energy in the ranges of 400 nm to 515 nm or 530 nm to 670 nm at a output of at least 300 millicandelas peak with a half-power output angle of +/−60 degrees, red light energy in the ranges of 610 nm to 640 nm at a output of 300 millicandelas peak with a half-power output angle of +/−60 degrees, and infrared light energy in the range of 820 nm to 880 nm at an output radiant flux of at least 300 mW peak with a half-power output angle of +/−60 degrees with each light source irradiating in pulses of equal on and off times between 50 msec and 500 msec, is one embodiment of many that creates the desired effects on tissues associated with the use of adult pleasure objects. Said effects are including, but not limited to, improved blood flow, improved blood vessel health, tissue regeneration, tissue tightening, improved cellular respiration, improved lubrication, decreased bacteria, decreased fungi, enhanced arousal and even pain relief. These effects may be directly caused in a user by use of the improved sexual stimulation device of the invention, as described herein. It is to be noted that this is just one of many embodiments of the invention, and any number of light sources emitting light energy within the range of 400 nm to 1000 nm at any radiant flux or millicandela output and angle may be used in any light source group of the invention. In order to emit the various bandwidths of light energy, each light source group may comprise more than one type of light source. For example, in the preferred embodiment described for which multiple frequencies of light are emitted by a light source group, a light source group may comprise light emitters which are defined as a plurality of LEDs, a plurality of lasers, or a plurality of light sources comprising a combination of LEDs and lasers. The light sources of the invention may be adapted to provide continuous output or provide output energy in pulses of any wave shape. "Half power angle" as used herein means the off-axis angle where the light source's luminous intensity is half the intensity at direct on-axis view. The axis of the light source is defined as the line of the vector of maximum intensity emanating from the light source.

In the various embodiments, the light energy may be pulsed on and off and may be any output energy with the ranges of output energies set forth herein. These light source output wavelengths may be administered in pulses that are in phase or out of phase as between light sources, and may be of any timing desired. It is an aspect of the invention that such light source pulse shape and timing may be, for some embodiments, programmable by use of a controller in communication with the light sources. The controller may be programmed by the user to produce a desired pulse shape and timing for the light sources of the invention. Alternatively the controller may be preprogrammed by a non-user.

In another preferred embodiment, these wavelengths, pulse widths, rest periods, and output power may be combined with mechanical energy such as that provided by an unbalanced vibration motor typical to that found in an adult sex toy, or any other method of mechanical energy delivery known in the art. In this manner, light therapy and mechanical stimulation, and, more specifically, vibration, may be applied together, or in alternating patterns of the user's choice, in order to achieve a desired stimulation effect.

In a preferred embodiment of the device, the light sources may be delivered to the tissue through an optical diffusing element, such as, for example, a silicone cover, to assure a homogeneous exposure of light to the selected tissue. In an alternate embodiment the device, the light sources may produce a selected pattern of optical energy to deliver optical energy to specific spots to provide differential exposure to unique spots on the tissue.

Yet further alternate embodiments will have preprogrammed light energy pulse patterns and or vibration patterns. The preferred embodiment comprises separate buttons for activating and choosing vibrations patterns and or light energy patterns.

In some of the specific preferred embodiments described herein, the mechanical stimulation example given is described as mechanical vibration produced by, for example and not by way of limitation, an offset vibrator motor. However, it is to be understood that the scope of the alternate embodiments of the invention includes all types of mechanical simulation devices and methods known in the art and which are adaptable to the invention without undue experimentation, such as sonic vibrators and mechanical manipulators of any type that produce rubbing, tapping, pressure, pressure that varies in intensity over time, and all other methods for mechanical stimulation.

Embodiments of the Physical Structure of the Invention

The physical structure elements of the invention may comprise a handle portion and a vaginal finger either alone or in combination with a clitoral finger or a urethral protuberance. The mechanical stimulation elements, light source elements, electrical components, physiologic sensors, and the associated mechanical structure and mounting hardware of these elements and components may reside in one more of the physical structure elements. The physical structure of the invention may, but does not necessarily, include a clitoral finger element or a protuberance element: these elements of the physical structure are optional and may be present in some embodiments of the invention, and not present in other embodiments, as described below.

In a first physical embodiment, the invention comprises a handle portion, a vaginal finger, and a clitoral finger. In a second physical embodiment, the invention comprises a handle portion and a vaginal finger. In a third physical embodiment, the invention comprises a handle portion, a vaginal finger, and a urethral protuberance.

Description of the First Physical Embodiment

Referring now to FIG. 1, a first physical embodiment of the sexual stimulation device of the invention is shown in perspective view. In this first physical embodiment the invention comprises vaginal finger 200, clitoral finger 300, handle 400 and keypad 403. When used by a female user, the female user would, in the most general case, hold the invention with one hand or both hands by handle 400 and slidingly engage vaginal finger 200 in the female user's vagina such that vaginal finger 200 applies mechanical simulation or vaginal light energy 201, or both, within the vagina at or near the user's G-spot, while clitoral finger 300 may apply clitoral light energy 301 or mechanical simulation, or both, at or near the user's clitoris. The application of light energy or mechanical simulation, or both, at or near the G-spot and/or clitoris in continuous fashion, or in patterns of vibration and light therapy as may be programmed into the invention, operate to cause more rapid and intense sexual stimulation than is possible without the invention. One exemplary method of the invention may comprise the following steps: applying lubrication, a lubricating light coupling agent or a combination of such agents as desired to vaginal finger 200 or clitoral finger 300, or both, slidingly engaging vaginal finger 200 in a vagina while resting clitoral finger 300 on or near a clitoris, turning the vaginal light source group 202 and clitoral light source group 302 of the apparatus ON, turning the vaginal vibrator 204 and clitoral vibrator 304 of the apparatus ON, and holding and applying movement as desired by grasping handle 400. Alternatively, light source groups and or vibrators may be turned on prior to contact of fingers to body tissue. The invention may further comprise control circuitry located in the handle 400 of the invention which may be used to operate the invention in one or more of many possible operational modes which are discussed further herein. Keypad 403 may cover the internal circuitry of the invention in such a manner as to provide environmental protection for the circuitry while at the same time allowing a user to control the operation of the invention by pressing on keypad 403 which is in physical contact with and engages switches 500 in electrical communication with the control circuitry. In normal use, handle 400 remains outside the body of the user. It can further be seen from FIG. 1 that vaginal finger 200, clitoral finger 300 and handle 400 form a unitary structure. In an alternate embodiment, clitoral finger 300 may not be present: in this alternate embodiment vaginal finger 200 and handle 400 form a unitary structure.

Figure 2:
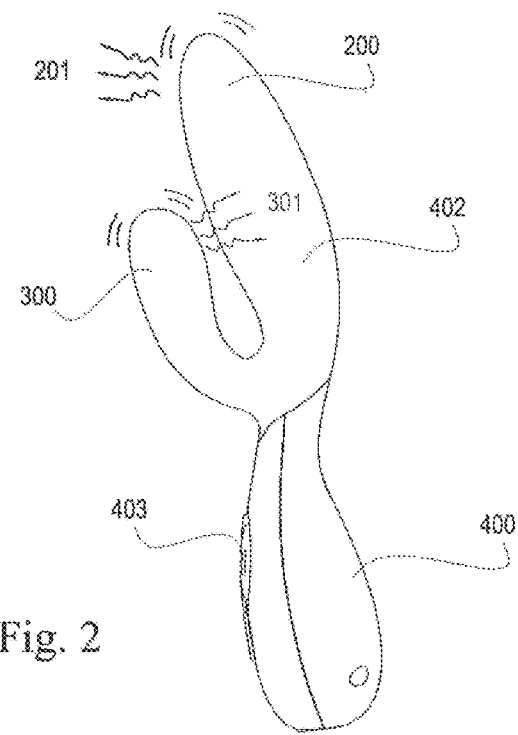
FIG. 2 depicts a side view of a first physical embodiment of the sexual stimulation device of the invention.

Referring to FIG. 2, vaginal finger 200 and the clitoral finger 300 are shown as vibrating, as during normal use in the preferred embodiment shown. Vaginal light energy 201 may also irradiate body tissue at or near the G-pot as it radiates from a side of distal end of vaginal finger 200 through flexible cover 402. Clitoral light energy 301 may irradiate body tissue at or near a user's clitoris as it radiates from the distal end of clitoral finger 300 through flexible cover 402. Flexible cover 402 may cover vaginal finger 200 and clitoral finger 300 and may, in a preferred embodiment, provide a hypo allergenic cleanable covering for vaginal finger 200 and clitoral finger 300. Flexible cover 402 may be fabricated from any material suitable for this purpose and transmissive at frequencies of 400 nm to 1000 nm including, but not limited to, silicone. The use of silicone in this preferred embodiment exhibits reduced friction characteristics which facilitates sliding engagement of vaginal finger 200 into the vagina of a user and also facilitates reduced frictional properties when clitoral finger 300 is in contact with the body of a user on or near the clitoris. Keypad 403 covers switches 500 (not shown in FIG. 2) which, in this preferred embodiment, are located within handle 400. The anterior side of keypad 403 is directly pressed by a user, for example by a user's finger, in order to activate controls of the invention. The posterior side of keypad 403 comprises keyboard button nipples which engage switches 500 (not shown in FIG. 2) disposed on a surface of controller printed wiring board 418 (not shown in FIG. 2) when a user presses any of the depressible control buttons disposed on the anterior side of keypad 403. In this way, a user may control the improved sexual stimulation device 100 to power the device on or off, and to command to operate in any of the modes described herein.

Figure 3:
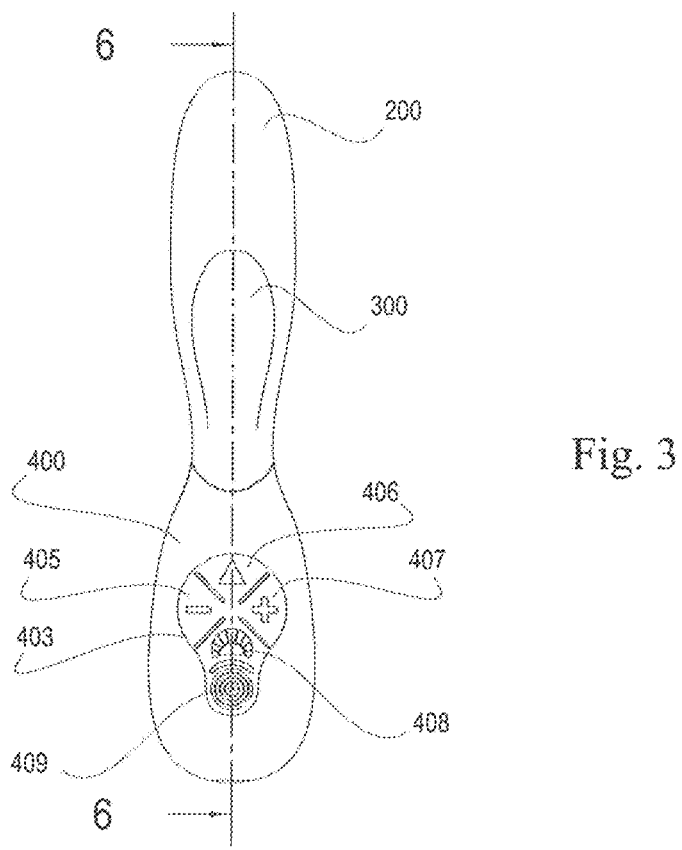
FIG. 3 depicts a front view of a first physical embodiment of the sexual stimulation device of the invention.

Referring now to FIG. 3, a front view of a preferred embodiment of the improved sexual stimulation device 100 of the invention is shown. Keypad 403 comprises a first depressible control button 405, a second depressible control button 406, a third depressible control button 407, fourth depressible control button 408, and fifth depressible control button 409 which are operated by a user to control the device. As described further herein, pressing downward on a depressible control button of the invention causes a keypad button nipple 428 (not shown in FIG. 3 but described further herein) disposed on the underside of keypad 403 to engage switches 500 (not shown in FIG. 3), which are in electrical communication with controller 501, providing commands as desired by the user to controller 501 (not shown in FIG. 3). The functions of the five depressible control buttons depicted in FIG. 3 are discussed hereinbelow. It is to be noted that the operational modes described herein are exemplary. Due to the programmable nature of controller 501 the depressible control buttons of the invention may be programmed to provide any combination of vibrator or light source on state, vibrator or light source off state, intensity of light, intensity of vibration, selection of pre-programmed vibration pulse shapes or continuous operation, selection of pre-programmed light energy pulse shapes or continuous operation, test modes, light energy and vibration display modes, and the like, may be programmed into the invention, selected and operated by a user pressing the depressible control buttons of the invention, which may be programmed to command any of these operations. Mechanical stimulating components other than vibrating motors may be substituted for vibrating motors and similarly controlled.

Figure 4:
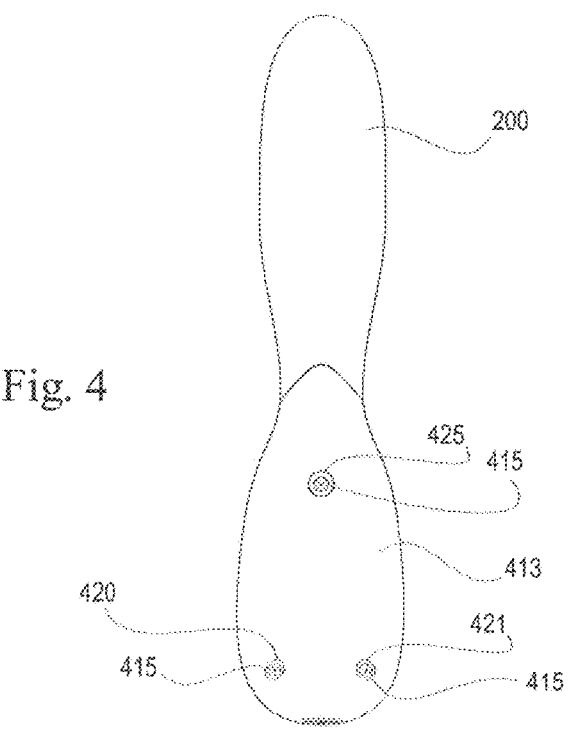
FIG. 4 depicts a rear view of a first physical embodiment of the sexual stimulation device of the invention.

Referring now to FIG. 4, a rear view of a preferred embodiment of the improved sexual stimulation device 100 of the invention is depicted. Shown in FIG. 4 are first cavity 420, second cavity 421 and third cavity 425, which may provide recessed insertion points for handle rear cover fastener 415 which are inserted through first cavity 420, second cavity 421 and third cavity 425 and are threadingly engaged into receiving female threads located on main support structure 412 (not shown in FIG. 4), and are therefore used to hold handle rear cover 413 into place. Alternatively, such cavities may be replaced by molded pins communicating with glue bosses rather than screw bosses.

Figure 5:
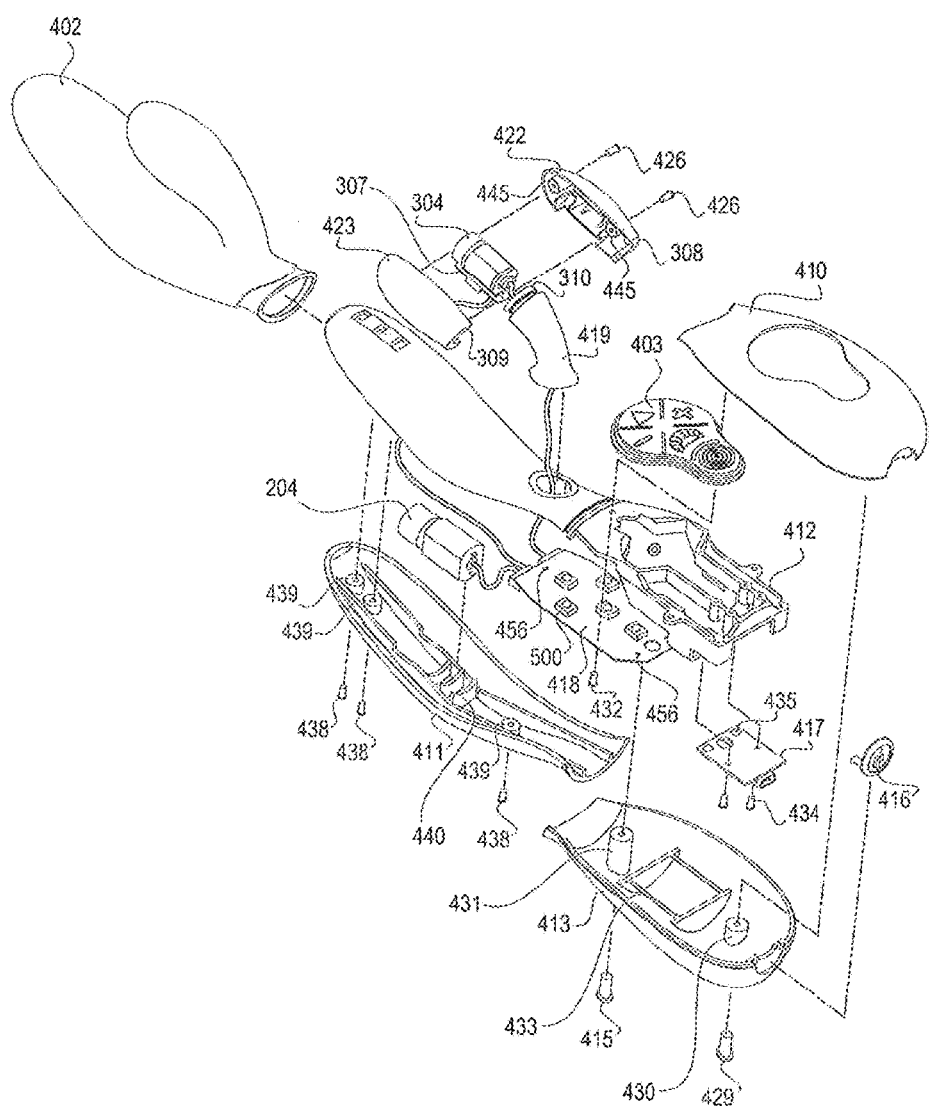
FIG. 5 depicts an exploded view of a first physical embodiment of the improved sexual stimulation device of the invention.

Referring now to FIG. 5, an exploded view of a preferred embodiment of the improved sexual stimulation device 100 of the invention is depicted. It is to be noted that, while a specific structure is shown in FIG. 5, there are many equivalent structures which are covered by the claims, and that the scope of the invention includes equivalent structures as would be understood by a person of ordinary skill in the mechanical arts.

Still referring to FIG. 5, main support structure 412 may be an elongate mechanical structure, preferably molded from plastic, but also, if desired, cast from metal or machined from any stable substantially rigid material such as plastic, phenolic, or other materials known in the art. Main support structure 412 provides support and attachment points for the various components and internal elements of the invention. The attachment points may generally be female bosses which are adapted to receive male threaded fasteners, and which may be threaded with female threads or may receive self-threading male threaded fasteners. All such female bosses may also serve as adhesive bosses to receive male pins and adhesive. Bosses, screw and pins may be decreased in number or removed in entirety if ultrasonic or similar welding is used to secure surfaces.

Still referring to FIG. 5, the attachments of keypad 403 and handle front cover plate 410 are discussed. Keypad 403 rests upon main support structure 412 and may be preferably bonded into place thereon using any suitable adhesive for bonding keypad 403, which may be fabricated from, for example, silicone, silicone compounds or any flexible polymer material. Alternatively, keypad 403 may be allowed to simply rest in place, sandwiched between handle front cover plate and main support structure 412. Keypad 403 may comprise a plurality of keypad button nipples 428 (not shown in FIG. 5) that act to engage switches 500 when a depressible control button is depressed. Handle front cover plate 410 may be attached to main support structure 412 by handle front cover fastener 429, which may reside in handle front cover fastener recess 430, with the male threaded portion of handle front cover fastener 429 protruding thru handle front cover fastener recess 430 and being threadingly received by a female boss disposed on the underside of handle front cover 410 (not shown in FIG. 5). Likewise, handle front cover plate 410 is attached at its forward end by second handle front cover fastener 432 which may pass through an opening in main support structure 412 to be threadingly received by a female boss disposed on the underside of handle front cover 410 (not shown in FIG. 5). In this manner, keypad 403 and handle front cover plate 410 are held in place, allowing keypad button nipples 428 (not shown in FIG. 5) to rest, or nearly rest, upon switches 500 such that depression of any of the depressible control buttons 405-409 cause activation of a switch underneath, sending commands to controller 501 (not shown in FIG. 5) on controller printed wiring board 418.

Referring still to FIG. 5, the attachment of controller printed wiring board 418, USB port printed wiring board 417, handle rear cover 413, and battery 503 (not shown in FIG. 5) is discussed. USB port printed wiring board 417 may be structurally attached to main support structure 412 by USB printed wiring board fasteners 434, which pass through clearance holes in USB port printed wiring board 417 to be threadingly received by female bosses disposed on the underside of main support structure 412 (not shown in FIG. 5). USB printed wiring board fasteners 434 may be electrically connected to controller printed wiring board 418 by wires or direct solder connection between them at USB printed wiring board solder attachments 435 or equivalent electrical connection structures known in the art. Alternatively, USB port printed wiring board 417 may be fabricated as a unitary element of controller printed wiring board 418. USB port printed wiring board 417 may comprise an electrical Universal Serial Bus (USB) charging port connector 451 to a charging or programming mating connector; however, the form of the electrical connection may take any form known or conceived in the electrical arts such as USB, micro-USB, custom design connection, or any other standard electrical connection suitable to fit within the envelope allowable. Controller printed wiring board 418 attaches to main support structure 412 by threaded fasteners (not shown in FIG. 5) passing through clearance holes 456 to be threadingly received by female bosses disposed on the underside of main support structure 412 (not shown in FIG. 5). Rear handle cover 413 is attached to main support structure 412 by handle rear cover fastener 415, which resides in handle rear cover fastener recess 431 with the male threaded portion of handle rear cover fastener 415 protruding through handle rear cover fastener recess 431 and being threadingly received by a female boss disposed on the underside of main support structure 412 (not shown in FIG. 5). Battery 503 (not shown in FIG. 5 for clarity sake, but shown in FIG. 6) may be sandwiched in place between the underside of controller printed wiring board 418 and battery support structure 433, and may be electrically connected with battery wires 436 (not shown in FIG. 5, but shown in FIG. 6) to controller printed wiring board 418 by a solder or other standard technique for making electrically conductive connection. Battery 503 may further comprise a battery compressive covering 437 such as compressible foam (not shown in FIG. 5 but shown in FIG. 6), or layers of compressive material fabricated from any suitable compressive material, so that it is sandwiched and held in place between the underside of controller printed wiring board 418 and battery support structure 433 with a compressive fit to prevent movement of the battery during shipping and use. Charging port connector 451 may be wired to communicate directly with controller 501 to facilitate programming. Likewise, a Bluetooth® chip and or WiFi chip may be used for similar purpose. Alternative methods of charging well known in the art such as inductive charging may be substituted for USB charging. The invention may further comprise an inductive charging circuit as is known in the art, such that the device may be charged by simply placing it in an inductive charging cradle.

Still referring to FIG. 5, vaginal finger rear cover plate 411 may attach to main support structure 412 by vaginal finger rear cover fasteners 438 which reside in vaginal finger rear cover recesses 439 with the male threaded portion of handle rear cover fastener 438 protruding through vaginal finger rear cover recesses 439 and being threadingly received by female bosses disposed on the underside of main support structure 412 (not shown in FIG. 5). Vaginal vibrator 204 may be supported on its underneath side by vaginal finger vibrator retaining structure 440 when vaginal finger rear cover plate 411 is attached in place. Vaginal vibrator 204 may be further held in place by main support structure vaginal supports 441 (not shown in FIG. 5 but shown in FIG. 6). Vaginal vibrator 204 may be engaged with main support structure vaginal vibrator supports 441 with a press fit or other engagement and for further retention may be bonded into place with adhesives.

Still referring to FIG. 5, clitoral finger base 419 rests upon main support structure 412 and is held in place by operation of flexible cover 402 which may provide, preferably, a covering with a slight compressive fit over clitoral finger 300 as well as vaginal finger 200. Clitoral finger base 419 is preferably fabricated from a flexible material such as, for instance, silicone or any similar flexible material. A preferred embodiment of the invention further comprises a clitoral finger first cover 422 and a clitoral finger second cover 423 of similar opposed cross section such that, when brought together as shown in FIG. 5 create a substantially smooth shape. While a preferred shape for the assembled clitoral finger is depicted in FIG. 2, the shape of clitoral finger 300 may be any shape suitable for pleasant contact on or near the clitoris of the user. Clitoral vibrator 304 may be attached to clitoral finger printed wiring board 307 (not shown in FIG. 5), upon which clitoral light source group 302 (not called out in FIG. 5) may also be mounted with electrical connection thereto. Clitoral finger printed wiring board 307 is held in place in clitoral finger vibrator structure 457 by clitoral finger printed wiring board retaining structure 444 (not shown in FIG. 5, but shown in FIG. 6) formed in clitoral finger first cover 422 which substantially forms a groove adapted to accept clitoral printed wiring board 307 in a press fit engagement. Clitoral vibrator 304 may be attached to clitoral finger printed wiring board 307 by adhesive bonding or any other means of attachment known in the mechanical arts. Clitoral finger first cover 422 is attached to clitoral finger second cover 423 by clitoral finger fasteners 426 which reside in clitoral finger first cover fastener recesses 445 with the male threaded portion of clitoral finger fasteners 426 protruding through clitoral finger first cover fastener recesses 445 and being threadingly received by female bosses disposed on an inside surface of clitoral finger second cover 423 (not shown in FIG. 5). Clitoral finger base 419 may further comprise clitoral finger base retaining groove 310 which is adapted to receive clitoral finger first cover retaining ring half 308 and clitoral finger second cover retaining ring half 309 such that, when clitoral finger fasteners 426 are installed and tightened, clitoral finger first cover retaining ring half 308 and clitoral finger second cover retaining ring half 309 are brought together to lock the assembled clitoral finger 300 components into place by operation of the retention properties of clitoral finger base retaining groove 310 holding clitoral finger first cover retaining ring half 308 and clitoral finger second cover retaining ring half 309 in place, as is shown in cross section view in FIG. 6.

Still referring to FIG. 5, main support structure 412, handle front cover plate 410, handle rear cover 413, vaginal finger rear cover plate 411, clitoral finger first cover 422, and clitoral finger second cover 423 may be fabricated from any material rigid enough to structurally support the assembly and repeated use of the improved sexual stimulation device 100 of the invention. Preferably, these components may be fabricated from any plastic material in order to facilitate ease of manufacture and minimize weight. Still within the scope of the invention, but less preferred, are other rigid materials such as metals, phenolic materials, organic materials, or any other materials rigid enough to support the assembly and repeated use of the invention. Such materials are known in the art.

Figure 6:
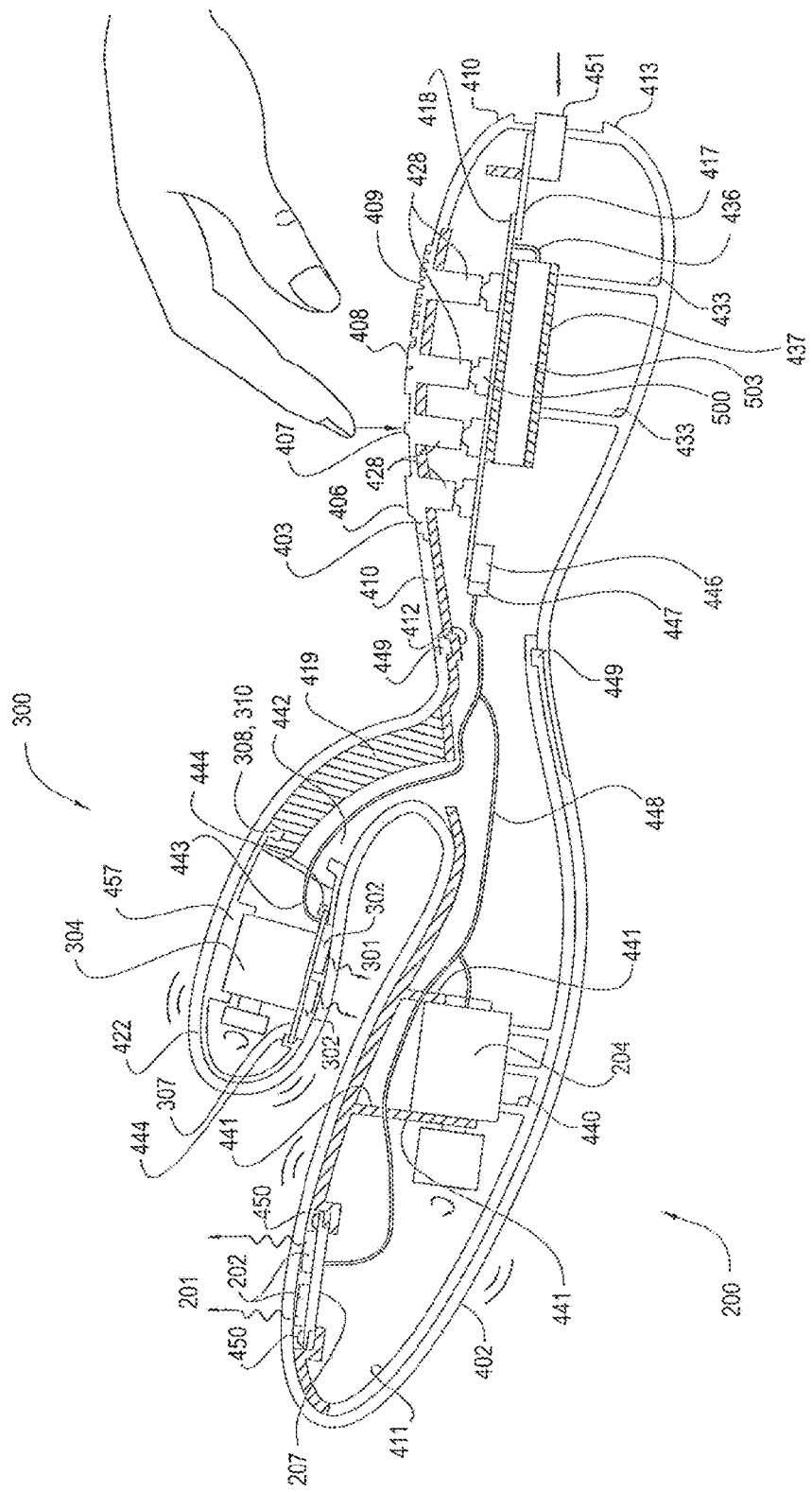
FIG. 6 depicts a cross-sectional view of a first physical embodiment of the improved sexual stimulation device of the invention, further depicting the location of the electrical components of the invention.

Referring now to FIG. 6, a cross sectional view of a preferred embodiment of the improved sexual stimulation device 100 of the invention is depicted. Keypad 403 is shown as being pressed by the finger of a user by depressing, for example, third depressible control button 407 which causes a keypad button nipple 428 to depress and activate the corresponding switch 500, which is mounted on controller printed wiring board 418. Thus a user may command and operate the improved sexual stimulation device 100 of the invention as desired by turning it on or off, manually changing modes, and commanding pre-programmed modes of operation, or the like. Battery 503 may be sandwiched in place between the underside of controller printed wiring board 418 and battery support structure 433, and may be electrically connected with battery wires 436 to controller printed wiring board 418 by a solder or other standard technique for making electrically conductive connection. Battery 503 may further comprise a battery compressive covering 437, or layers of compressive material fabricated from any suitable compressive material, so that it is sandwiched and held in place between the underside of controller printed wiring board 418 and battery support structure 433 with a compressive fit to prevent movement of the battery during shipping and use. Controller printed wiring board connector 446 mates mechanically and electrically with wiring connector 447, enabling the connection and disconnection of clitoral finger wires 443 and vaginal finger wires 448 from controller printed wiring board 418 to facilitate assembly and repair.

Still referring to FIG. 6, flexible cover 402 covers vaginal finger 200 and clitoral finger 300 with a slight compressive fit, and may be further captured in place by flexible cover retaining step 449 which may be received by a matching groove in main support structure 412 and rear handle cover 413 as shown in FIG. 6. Further, vaginal vibrator 204 may be supported on its underneath side by vaginal finger vibrator retaining structure 440 when vaginal finger rear cover plate 411 is attached in place to vaginal vibrator 204 is further held in place by main support structure vaginal supports 441. Vaginal vibrator 204 may be engaged with main support structure vaginal vibrator supports 441 with a press fit engagement and for further retention may be bonded into place with adhesives. Vaginal finger printed wiring board 207 is held in place by vaginal printed wiring board fasteners 450 which are received by holes in main support structure 412 and which are adapted to receive vaginal printed wiring board fasteners 450, which may be standard threaded fasteners, self-tapping or any other fastener type known in the art. When vaginal printed wiring board 207 is mounted as shown, vaginal light energy 201 from vaginal light energy source group 202 may exit vaginal finger 200 by passing through flexible cover 402 which is transmissive at the light frequencies stated herein. Vaginal finger wires 448 establish electrical communication between vaginal printed wiring board 207, vaginal vibrator 204, and controller printed wiring board 418. Clitoral finger printed wiring board 307 is held in place in clitoral finger 300 by clitoral finger printed wiring board retaining structure 444 formed in clitoral finger first cover 422 which substantially forms a groove adapted to accept clitoral printed wiring board 307 in a press fit engagement. Clitoral vibrator 304 may be attached to clitoral printed wiring board 307 by adhesive bonding or any other means of attachment known in the mechanical arts. When clitoral printed wiring board 307 is mounted as shown, clitoral light energy 301 from clitoral light energy source group 302 may exit clitoral finger 300 by passing through flexible cover 402 which is transmissive at the light frequencies stated herein. Clitoral finger wires 443 establish electrical communication between clitoral printed wiring board 307, clitoral vibrator 304, and controller printed wiring board 418. Clitoral finger base 419 rests upon main support structure 412. Clitoral finger wires 443 pass through clitoral finger base channel 442. Clitoral finger base 419 may further comprise clitoral finger base retaining groove 310 which is adapted to receive clitoral finger first cover retaining ring half 308 and clitoral finger second cover retaining ring half 309 such that, when clitoral finger fasteners 426 (not shown in FIG. 6) are installed and tightened, clitoral finger first cover retaining ring half 308 and clitoral finger second cover retaining ring half 309 (not shown in FIG. 6) are brought together to lock the assembled clitoral finger 300 components into place by operation of the retention properties of clitoral finger base retaining groove 310 holding the retainer ring halves, 308 and 309, in place.

Charging port connector 451 is electrically and mechanically attached to USB port printed wiring board 417, and protrudes through an opening formed in handle front cover plate 410 and handle rear cover 413 when they are assembled as described herein.

Description of the Second Physical Embodiment

In a second physical embodiment, the invention is as described above in the first physical embodiment but it does not comprise a clitoral finger: it may comprise a handle portion and a vaginal finger. In this embodiment, the clitoral finger and protuberance are not necessarily present in the invention.

Figure 12A:
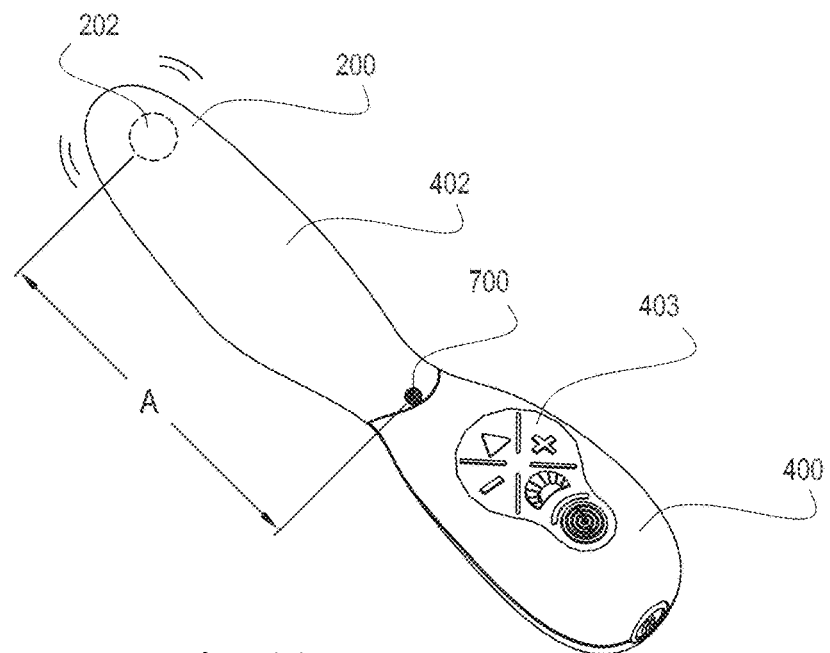
FIG. 12A depicts a front view of a second physical embodiment of the invention comprising a vaginal finger, a handle portion and an optional orientation mark.
Figure 12B:
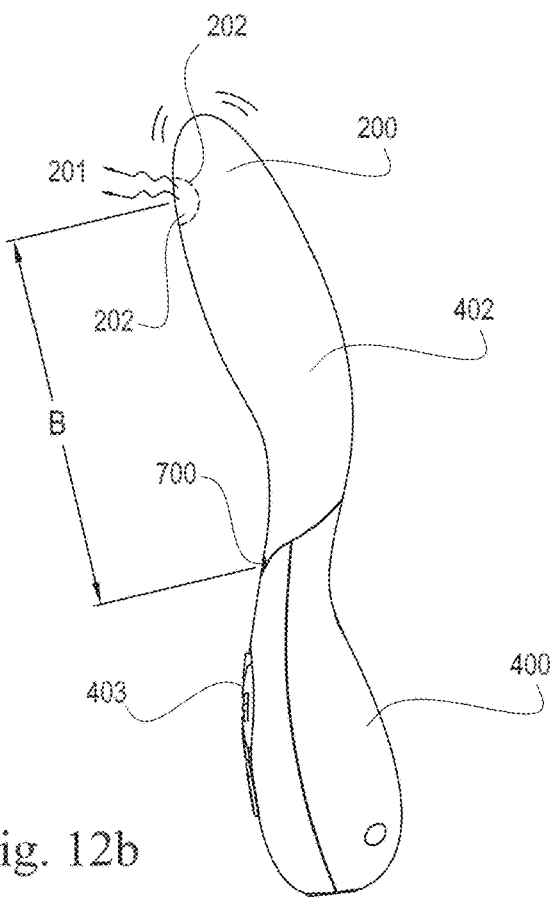
FIG. 12B depicts a side view of a second physical embodiment of the invention comprising a vaginal finger, a handle portion and an optional orientation mark.

Referring now to FIGS. 12A and 12B the second physical embodiment of the invention is depicted in a front view and side view, respectively. The physical structure of the second physical embodiment of the invention comprises vaginal finger 200 as hereinbefore described and handle portion 400, also as hereinbefore described. Keypad 403 may be disposed in handle portion 400 as hereinbefore described, and flexible cover 402 may cover vaginal finger 200 as hereinbefore described.

Figure 16:
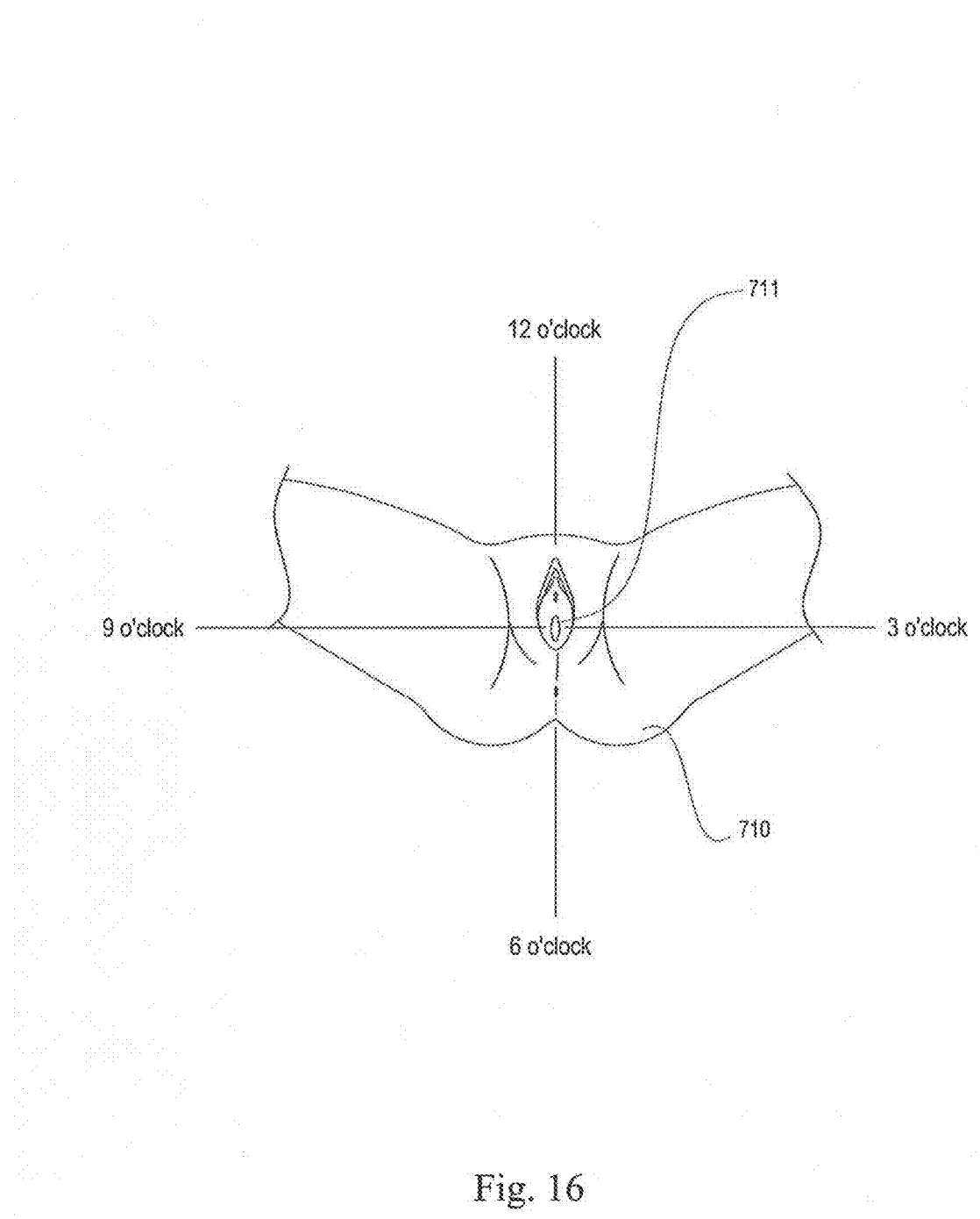
FIG. 16 depicts a reference view of a female user in which 12 o'clock, 3 o'clock, 6 o'clock and 9 o'clock orientations are depicted for reference.

Still referring to FIGS. 12A and 12B, an alternate embodiment of the second physical embodiment of the invention may comprise an orientation mark. It is preferred that, when this embodiment of the improved sexual stimulation device of the invention is used, vaginal finger 200 directly applies mechanical stimulation and/or light stimulation on an area of a female user's body that is on or near the Gräfenberg Spot, or G-spot. In this physical embodiment of the invention, a user may utilize the orientation mark to assist orientation and location of vaginal finger 200 such that vaginal finger 200 directly applies mechanical stimulation and/or light stimulation on an area of a female user's body that is on or near the Gräfenberg Spot, or G-spot, when vaginal finger 200 is slidingly engaged with the user's vagina as follows. Vaginal light source group may be located a distance A from orientation mark 700 such that when the user slidingly engages vaginal finger 200 into the vagina until orientation mark 700 is disposed just outside, or within 0.5 inches, of the vaginal opening at 12 o'clock position, vaginal finger 200 will be correctly oriented and disposed so as to allow optimal illumination of the G-spot with vaginal light energy 201 from vaginal light source group 202, or apply mechanical stimulation from vaginal vibrator 204 to the area of the G-spot, or both, as hereinbefore described. The user orients the vaginal finger 200 such that it rests just outside the vaginal opening 711 at the 12 o'clock position (see FIG. 16), which means that orientation mark 700 on vaginal finger 200 is facing directly "upwards" in the 12 o'clock position as is shown in FIG. 16. In FIG. 16, a female user of the invention is oriented with buttocks 710 in a "downward" position, which is shown in the figure as the 6 o'clock position. Thus, when the user slidingly engages vaginal finger 200 into the vagina until orientation mark 700 is disposed just outside, preferably within 0.5 inches, of the vaginal opening at 12 o'clock position, vaginal finger 200 will be correctly oriented and disposed so as to allow optimal illumination of the G-spot with vaginal light energy 201 from vaginal light source group 202, or apply mechanical stimulation from vaginal vibrator 204 to the area of the G-spot, or both, as hereinbefore described. In this manner, mechanical stimulation and/or light stimulation may be directly applied to the area of the G-spot, which is the area of the vagina known to result in maximum arousal and sexual stimulation for a female.

Although the preferred location of orientation mark 700 on the invention is as shown in FIGS. 12A and 12B, alternative locations for orientation mark 700 are within the scope of the claimed invention. The scope of the claimed invention includes any location or type of orientation mark that allows the use orient and locate orientation mark 700 by reference to a portion or feature of the user's body such that either vaginal light energy 201 from vaginal light source group 202 or mechanical stimulation resulting from the operation of vaginal vibrator 204 (not shown in FIG. 12A or 12B) is applied to all or a portion of the area of the G-spot of the user.

Orientation mark 700 may take the form of a raised or depressed dimple in the surface of the invention, a scribed mark of any shape, a mark by applying paint, ink or any other known material for marking a surface, or any other means of marking or type of marking known in the art for marking a surface.

Still referring to FIGS. 12A and 12B, the device is intended to be used primarily by a female user, who, in one of many methods of use, would hold the invention with one hand or both hands by handle 400 and slidingly engage vaginal finger 200 in the user's vagina such that vaginal finger 200 applies mechanical stimulation or vaginal light energy 201, or both, in the area of the user's G-spot, while orientation mark 700 rests just outside the vagina at the 12 o'clock position as depicted in reference diagram of FIG. 16. The distance A between the orientation mark and vaginal light source group 202 placed on the same side of finger shall be equal to the distance between the external urethral meatus in women and the G-Spot. The distance A typically falls in a range of 2.5-7.6 cm. Said vaginal light source group 202 should preferably be placed in the midline of vaginal finger 200, but may located off-midline. The application of light energy 201 or mechanical stimulation, or both, at or near the G-spot in continuous fashion, or in patterns of vibration and light therapy as may be programmed into the invention as described elsewhere herein, operate to cause more rapid and intense sexual stimulation than is possible without the invention.

Figure 12C:
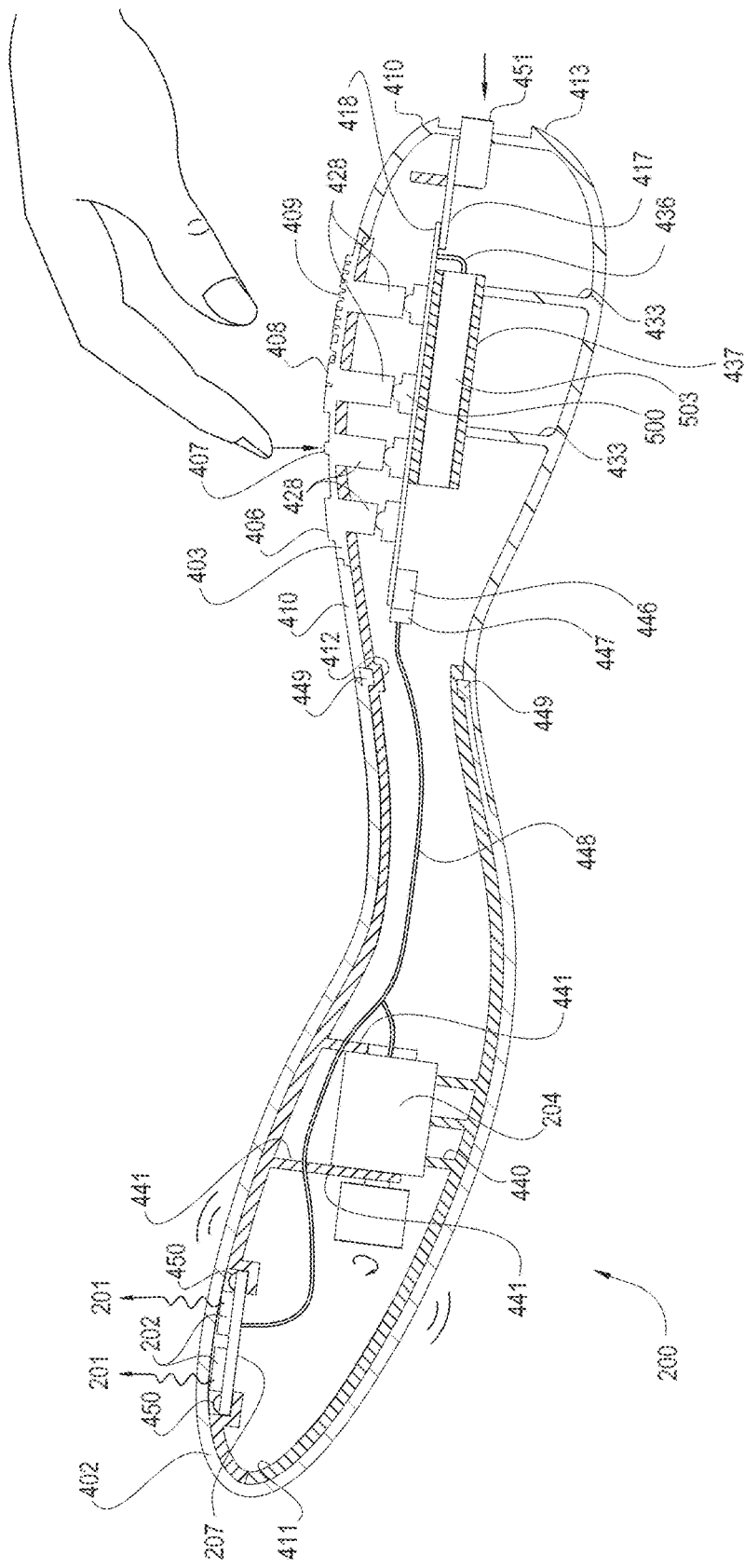
FIG. 12C depicts a cross sectional side view of a second physical embodiment of the invention comprising a vaginal finger and a handle portion.

Referring now to FIG. 12C, a cross sectional view of the second physical embodiment of the invention, in which the invention comprises a vaginal finger and handle portion, but does not comprise a clitoral finger, is shown. Keypad 403 is shown as being pressed by the finger of a user by depressing, for example, third depressible control button 407 which causes a keypad button nipple 428 to depress and activate the corresponding switch 500, which is mounted on controller printed wiring board 418. Thus a user may command and operate the improved sexual stimulation device 100 of the invention as desired by turning it on or off, manually changing modes, and commanding pre-programmed modes of operation, or the like. Battery 503 may be sandwiched in place between the underside of controller printed wiring board 418 and battery support structure 433, and may be electrically connected with battery wires 436 to controller printed wiring board 418 by a solder or other standard technique for making electrically conductive connection. Battery 503 may further comprise a battery compressive covering 437, or layers of compressive material fabricated from any suitable compressive material, so that it is sandwiched and held in place between the underside of controller printed wiring board 418 and battery support structure 433 with a compressive fit to prevent movement of the battery during shipping and use. Controller printed wiring board connector 446 mates mechanically and electrically with wiring connector 447, enabling the connection and disconnection of vaginal finger wires 448 from controller printed wiring board 418 to facilitate assembly and repair.

Still referring to FIG. 12C, flexible cover 402 covers vaginal finger 200 with a slight compressive fit, and may be further captured in place by flexible cover retaining step 449 which may be received by a matching groove in main support structure 412 and rear handle cover 413 as shown in FIG. 13. Further, vaginal vibrator 204 may be supported on its underneath side by vaginal finger vibrator retaining structure 440 when vaginal finger rear cover plate 411 is attached in place to vaginal vibrator 204 is further held in place by main support structure vaginal supports 441. Vaginal vibrator 204 may be engaged with main support structure vaginal vibrator supports 441 with a press fit engagement and for further retention may be bonded into place with adhesives. Vaginal finger printed wiring board 207 is held in place by vaginal printed wiring board fasteners 450 which are received by holes in main support structure 412 and which are adapted to receive vaginal printed wiring board fasteners 450, which may be standard threaded fasteners, self-tapping or any other fastener type known in the art. When vaginal printed wiring board 207 is mounted as shown, vaginal light energy 201 from vaginal light energy source group 202 and 202*a* may exit vaginal finger 200 by passing through flexible cover 402 which is transmissive at light frequencies stated herein. Vaginal light source groups 202 may be disposed anywhere about vaginal finger. Vaginal finger wires 448 establish electrical connection between vaginal printed wiring board 207, vaginal vibrator 204, and controller printed wiring board 418.

Charging port connector 451 is electrically and mechanically attached to USB port printed wiring board 417, and protrudes through an opening formed in handle front cover plate 410 and handle rear cover 413 when they are assembled as described herein.

Description of the Third Physical Embodiment of the Invention

Figure 13A:
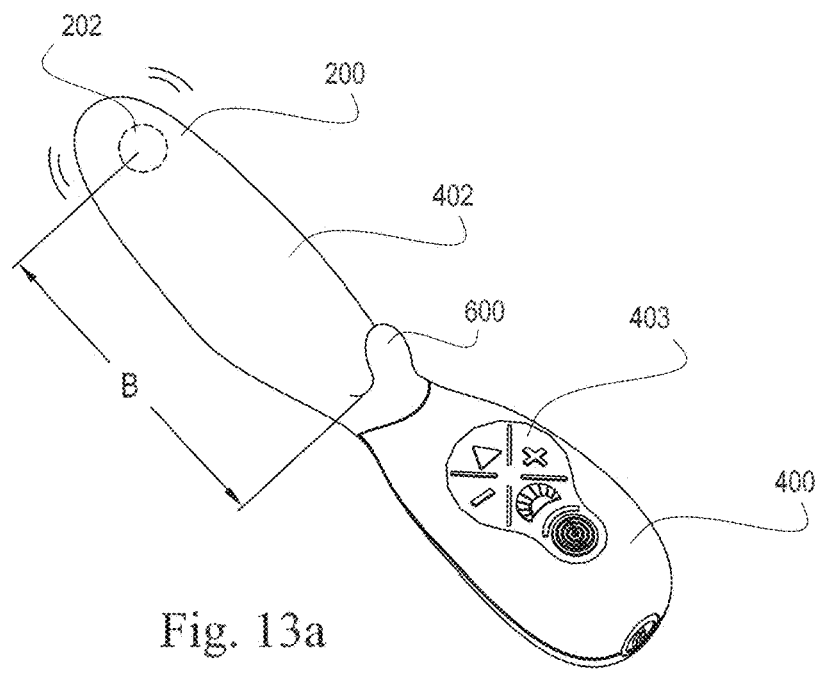
FIG. 13A depicts a front view of a third physical embodiment of the invention comprising a vaginal finger, a handle portion and a urethral protuberance.
Figure 13B:
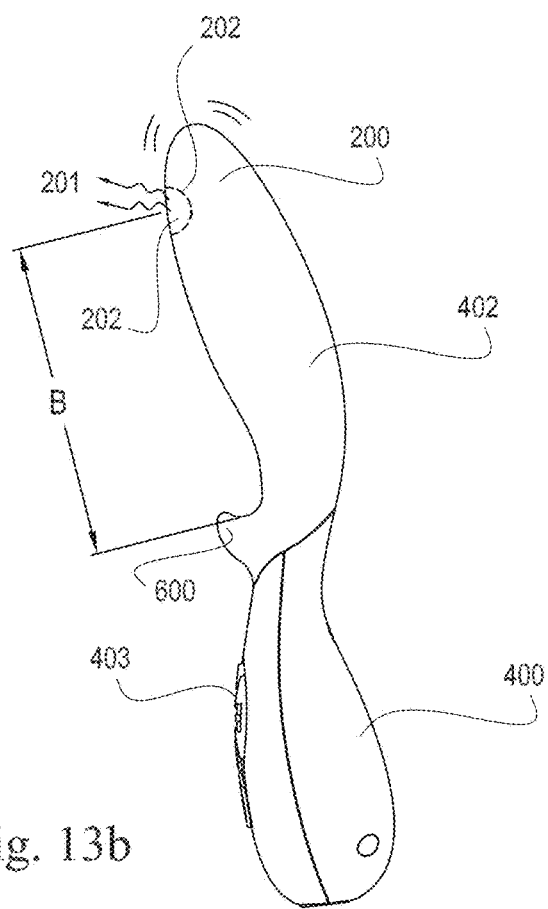
FIG. 13B depicts a side view of a third physical embodiment of the invention comprising a vaginal finger, a handle portion and a urethral protuberance.

Referring now to FIGS. 13A and 13B the third physical embodiment of the invention, in which the invention comprises a handle portion 400, a vaginal finger 200, and a protuberance 600, is depicted in a front view and side view, respectively. The physical structure of the third physical embodiment of the invention comprises vaginal finger 200 as hereinbefore described and handle portion 400, also as hereinbefore described. Keypad 403 may be disposed in handle portion 400 as hereinbefore described, and flexible cover 402 may cover vaginal finger 200 as hereinbefore described. The third physical embodiment of the invention further comprises protuberance 600, which may be used to aid the user in positioning the invention as it is slidingly engaged with a user's vagina such that mechanical stimulation and/or light stimulation may be directly applied to the area of the user's G-spot, which is the area of the vagina known to result in maximum arousal and sexual stimulation for a female.

Still referring to FIGS. 13A and 13B, when this third physical embodiment of the improved sexual stimulation device of the invention is used, vaginal finger 200 applies mechanical stimulation or vaginal light energy 201, or both, in the area of the user's Gräfenberg Spot, or G-spot, and protuberance 600 rests at or near the external urethral meatus of the user. When the user slidingly engages vaginal finger 200 into the user's vagina and rests protuberance 600 at the external urethral meatus, vaginal finger 200 will be correctly oriented and disposed within the vagina to apply mechanical stimulation and vaginal light energy 201 to the user's G-spot. In this manner, mechanical stimulation and vaginal light energy 201 are directly applied to the areas of the vagina known to result in maximum arousal and sexual stimulation. Although the preferred orientation of the protuberance as is as shown in FIGS. 13A and 13B, which may be defined as the urethral protuberance configuration, the only requirement for the position of protuberance 600 is that it be located on the outer surface of vaginal finger 200 or handle portion 400 such that when protuberance 600 rests on an anatomic feature of the user's body that is easily felt by the user, vaginal finger 200 applies mechanical stimulation or vaginal light energy 201, or both, to the user's G-Spot or any other desired anatomic structure. One example of such alternative placement is the alternate embodiment of the invention in which protuberance 600 is oriented 180 degrees from that shown in FIGS. 13A and 13B, such that it is oriented in the 6 o'clock position when the invention is slidingly engaged with a user's vagina such that vaginal light source group 202 is oriented in the 12 o'clock position, using the reference diagram shown in FIG. 16. In this alternate embodiment, the resting of the protuberance 600 on the anus or within 0.5 inches of the anus would create the appropriate placement of mechanical stimulation or vaginal light energy 201, or both, on the area of the G-Spot. This embodiment of the invention in which the protuberance rests on the anus or within 0.5 inches of the anus may be defined as the anal protuberance configuration.

Still referring to FIGS. 13A and 13B, the third physical embodiment of the invention is further discussed. The invention is intended to be used primarily by a female user, who, in the most general case, would hold the invention with one hand or both hands by handle 400 and slidingly engage vaginal finger 200 in the user's vagina such that vaginal finger 200 applies mechanical stimulation and vaginal light energy 201 within the vagina in the area of the G-spot while protuberance 600 touches or is located within 0.5 inches of the user's external urethral meatus. The distance B between protuberance 600 and vaginal light source group 202 is preferably equal to the distance between the user's external urethral meatus and the user's G-Spot. This distance B typically falls in a range of 2.5-7.6 cm. Vaginal light source group 202 should preferably be disposed in the midline of vaginal finger 200 as is depicted in the figures of the drawing, but may be remotely located using optical fibers or light tubes to transmit light energy to the area of vaginal finger 200 so as to apply vaginal light energy 201 to the area of the user's G-spot at a distance B from protuberance 600. The application of vaginal light energy 201 and mechanical stimulation at or near the G-spot in continuous fashion, or in patterns of vibration and light therapy as may be programmed into the invention as is discussed herein, operate to cause more rapid and intense stimulation than is possible without the invention.

Figure 13C:
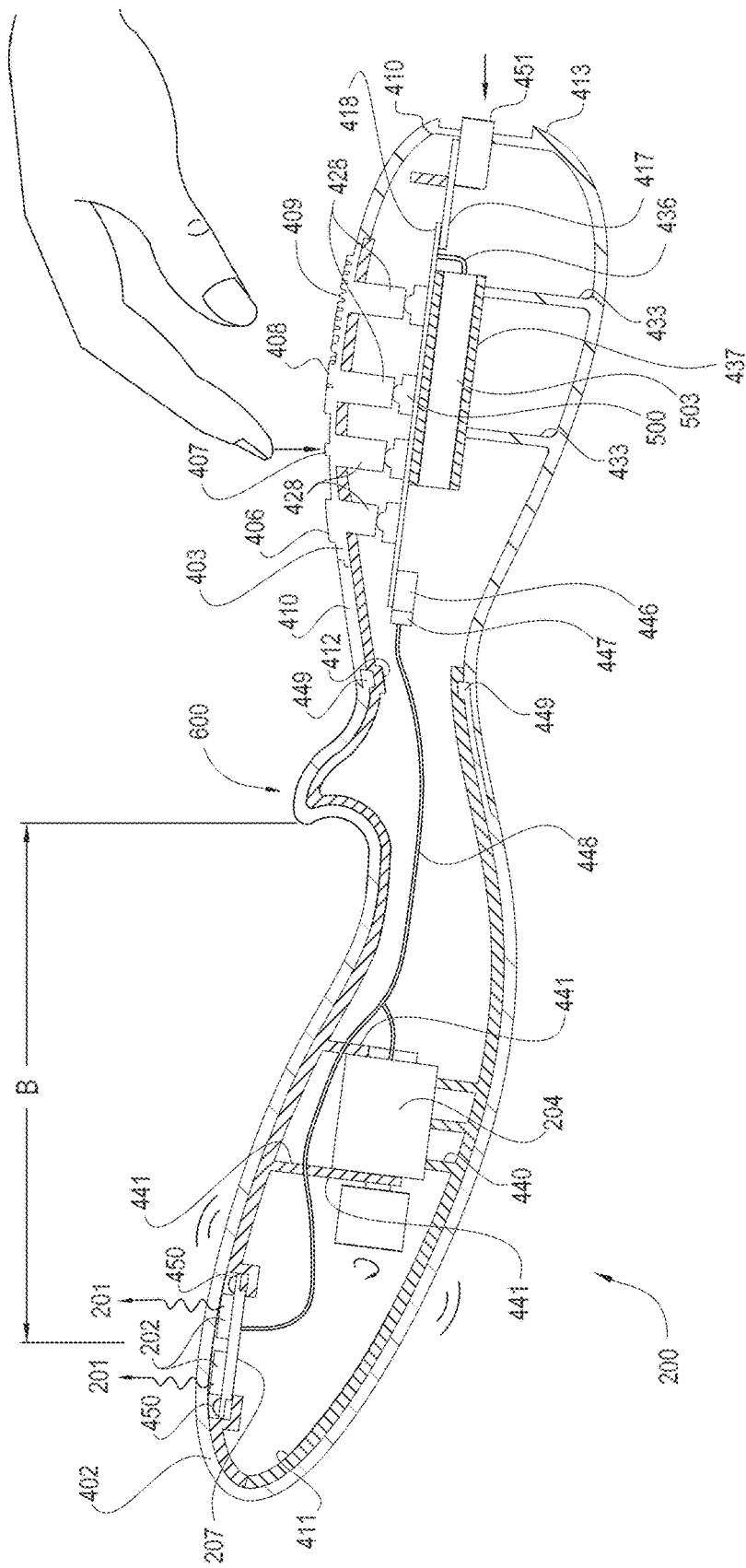
FIG. 13C depicts a cross sectional view of a third physical embodiment of the invention comprising a vaginal finger, a handle portion and a urethral protuberance.

Referring now to FIG. 13C, a cross sectional view of the second physical embodiment of the invention is shown. Keypad 403 is shown as being pressed by the finger of a user by depressing, for example, third depressible control button 407 which causes a keypad button nipple 428 to depress and activate the corresponding switch 500, which is mounted on controller printed wiring board 418. Thus a user may command and operate the improved sexual stimulation device 100 of the invention as desired by turning it on or off, manually changing modes, and commanding pre-programmed modes of operation, or the like. Battery 503 may be sandwiched in place between the underside of controller printed wiring board 418 and battery support structure 433, and may be electrically connected with battery wires 436 to controller printed wiring board 418 by a solder or other standard technique for making electrically conductive connection. Battery 503 may further comprise a battery compressive covering 437, or layers of compressive material fabricated from any suitable compressive material, so that it is sandwiched and held in place between the underside of controller printed wiring board 418 and battery support structure 433 with a compressive fit to prevent movement of the battery during shipping and use. Controller printed wiring board connector 446 mates mechanically and electrically with wiring connector 447, enabling the connection and disconnection of vaginal finger wires 448 from controller printed wiring board 418 to facilitate assembly and repair.

Still referring to FIG. 13C, flexible cover 402 covers vaginal finger 200 with a slight compressive fit, and may be further captured in place by flexible cover retaining step 449 which may be received by a matching groove in main support structure 412 and rear handle cover 413 as shown in FIG. 13. Further, vaginal vibrator 204 may be supported on its underneath side by vaginal finger vibrator retaining structure 440 when vaginal finger rear cover plate 411 is attached in place to vaginal vibrator 204 is further held in place by main support structure vaginal supports 441. Vaginal vibrator 204 may be engaged with main support structure vaginal vibrator supports 441 with a press fit engagement and for further retention may be bonded into place with adhesives. Vaginal finger printed wiring board 207 is held in place by vaginal printed wiring board fasteners 450 which are received by holes in main support structure 412 and which are adapted to receive vaginal printed wiring board fasteners 450, which may be standard threaded fasteners, self-tapping or any other fastener type known in the art. When vaginal printed wiring board 207 is mounted as shown, vaginal light energy 201 from vaginal light energy source group 202 and optional second vaginal light energy source group 202a may exit vaginal finger 200 by passing through flexible cover 402 which is transmissive at light frequencies stated herein. Vaginal light source groups 202 may be disposed anywhere about vaginal finger. Vaginal finger wires 448 establish electrical connection between vaginal printed wiring board 207, vaginal vibrator 204, and controller printed wiring board 418. The distance B between protuberance 600 and vaginal light source group 202 is preferably equal to the distance between the user's external urethral meatus and the user's G-Spot.

Charging port connector 451 is electrically and mechanically attached to USB port printed wiring board 417, and protrudes through an opening formed in handle front cover plate 410 and handle rear cover 413 when they are assembled as described herein.

Figure 7A:
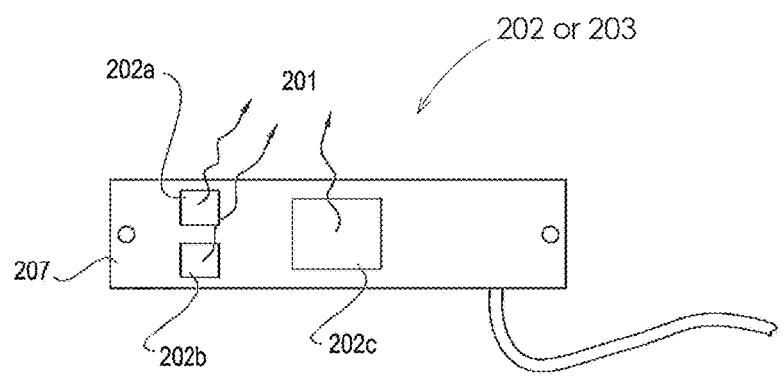
FIG. 7A depicts a top view of an exemplary embodiment of a vaginal printed wiring board of a preferred embodiment of the invention, depicting a clitoral source group in electrical and mechanical communication with a clitoral finger printed wiring board.
Figure 7B:
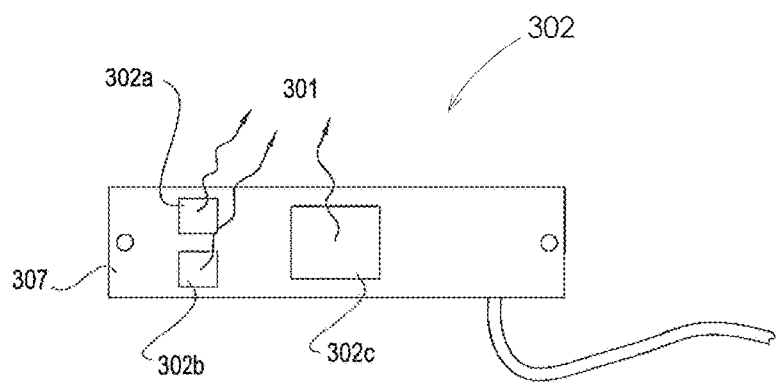
FIG. 7B depicts a top view of an exemplary embodiment of a clitoral printed wiring board of a preferred embodiment of the invention, depicting a vaginal source group in electrical and mechanical communication with a vaginal finger printed wiring board.

Referring now to FIG. 7A and FIG. 7B, details of a preferred embodiment of vaginal finger printed wiring board 207 and clitoral finger printed wiring board 307 are depicted. Both of these printed wiring boards may contain one or more light sources in electrical connection with wiring that is in electrical connection with controller printed wiring board 418 as follows. Referring first to FIG. 7A, a first vaginal finger printed wiring board 207 may comprise vaginal light source group 202 which is itself comprised of at least one light source, but preferably is comprised of a variety of light sources in order to combine a variety of frequencies of light that may be radiated as vaginal light energy 201. Vaginal light source group 202 may comprise any number of light sources. In the preferred embodiment shown in FIG. 7A, three vaginal light sources 202a, 202b and 202c are depicted as comprising vaginal light source group 202 or 203. Each light source of vaginal light source group 202 or 203 may consist of one or more light sources, which may, but are not necessarily, light emitting diodes. Vaginal light sources 202a, 202b and 202c may be soldered to vaginal finger printed wiring board 207 to provide electrical and mechanical connected thereto, or may be attached to vaginal finger printed wiring board 207 in any manner known in the electrical assembly arts. In an alternate embodiment, the light sources of vaginal light source group 202 or 203 may be individually attached to main support structure 412 or its equivalent and connected with discrete wires (not shown in FIG. 7A) to controller printed wiring board 418. Referring now to FIG. 7B, clitoral finger printed wiring board 307 may likewise comprise clitoral light source group 302 which is itself comprised of at least one light source, but preferably is comprised of a variety of light sources in order that a variety of frequencies of light may be radiated as clitoral light energy 301. Clitoral light source group 302 may comprise any number of light sources. In the preferred embodiment shown in FIG. 7B, three clitoral light sources 302a, 302b and 302c are depicted as comprising clitoral light source group 302. Each light source may consist of one or more light sources, which may, but are not necessarily, light emitting diodes. Clitoral light sources 302a, 302b and 302c may be soldered to clitoral finger printed wiring board 307 to provide electrical and mechanical connected thereto, or may be attached to clitoral finger printed wiring board 307 in any manner known in the electrical assembly arts. In an alternate embodiment, the light sources of clitoral light source group 302 may be individually attached to main support structure or its equivalent and connected with discrete wires (not shown in FIG. 7B) to controller printed wiring board 418. In a preferred embodiment, the light sources of vaginal light source group 202 or 203 may be defined as light source 202a and 202b, each having a "blue" LED emitting wavelengths between 400 nm to 515 nm and a "red" LED emitting wavelengths between 610 nm to 640 nm; and light source 202c comprising an infrared LED emitting wavelengths between 820 nm to 880 nm. Likewise, in preferred embodiment, the light sources of clitoral light source group 302 may be defined as light as light source 302a and 302b, each having a "blue" LED emitting wavelengths between 400 nm to 515 nm and a "red" LED emitting wavelengths between 610 nm to 640 nm and light source 302c comprising an infrared LED emitting wavelengths between 820 nm to 880 nm. While these exemplary light source groups are discussed herein as regards the modes of operation of the invention, it is to be understood that the exact number of light sources in each light source group is variable, as well as are the frequencies of light emitted, the output power of the emitted light energy, and the modes of operation. Thus, a light source group may consist of two "blue" LEDs, three infrared LEDs, only one "red" LED, and LEDs with differing wavelengths and output powers other than the blue, red and infrared light sources described above, and so on. All combinations of light source types are considered within the scope of the claimed invention. Likewise, vaginal light source group 202, vaginal light source group 203 and clitoral light source group 302 may each comprise any number of light sources that, preferably but not necessarily, each emit light energy at wavelength greater than 400 nm and less than 1000 nm, although all other wavelengths are within the scope of the invention.

Furthermore, alternate embodiments of the invention may comprise a light source or light sources disposed only in clitoral finger 300 and not in vaginal finger 200, and vice versa. Additionally, alternate embodiments may utilize light sources known in the art that are disposed in the handle of the device or external to the device whereby therapeutic light energy is transmitted to vaginal and or clitoral finger through light tubes or fibers such as described below.

Figure 8A:
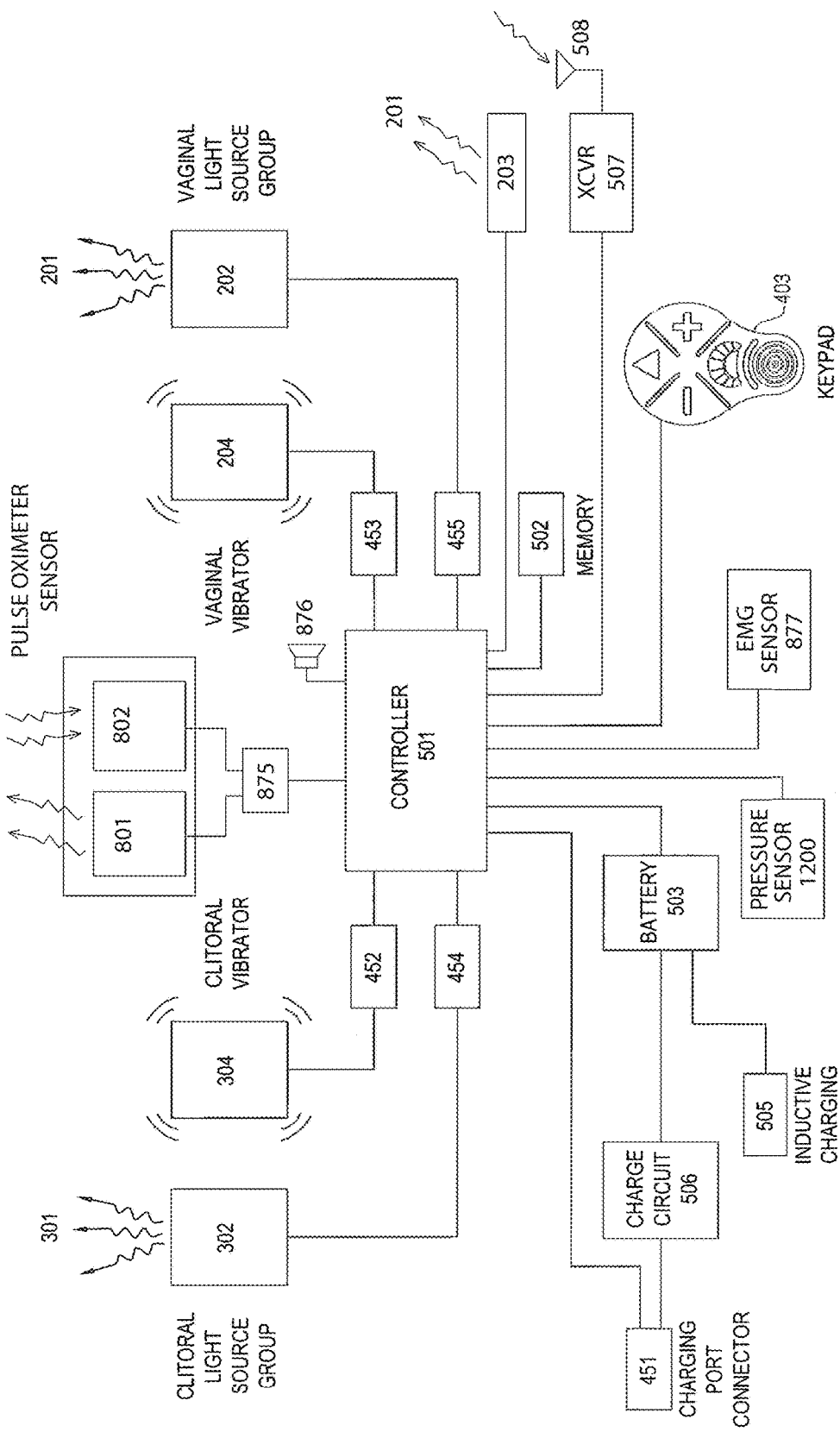
FIG. 8A depicts a functional block diagram of an embodiment of the sexual stimulation device of the invention, depicting optional elements of the invention comprising one or more optional pulse oximeter sensors, one or more optional EMG sensors, an optional transceiver and antenna and one or more optional pressure transducers.

Referring now to FIG. 8A, an electrical block diagram of the sexual stimulation device 100 of the invention is depicted, in which the electrical components of the various embodiments of the invention, some of which are optional as herein described, are depicted. The invention may comprise a vaginal light source group 202, a clitoral light source group 302, a vaginal vibrator 204, a clitoral vibrator 304, a controller 501, a memory 502 which may be a non-transitory computer readable memory, a charging circuit 506, an inductive charging circuit 505, a charging and programming port connector, such as a USB connector, 451, a keypad 403. Controller 501 may reside on controller printed wiring board 418 (not shown in FIG. 8) and be soldered thereto. Controller 501 may be a single electrical device or a plurality of electrical devices that allow control inputs to be accepted from a user through the use of keypad 403, by a user depressing one or more depressible control buttons as hereinbefore described. Controller 501 may comprise any electrical components, which, either alone or in combination, are known in the art for executing commands, which may be in the form of computer readable instructions, and providing an output based on user inputs, pre-programmed data stored in non-transitory computer readable memory 502, or combinations thereof. Thus, controller 501 may comprise programmable logic devices, non-field-programmable firmware devices, field programmable firmware devices, microprocessors, microcontrollers, discrete logic and other logic devices adapted to perform the functions of receiving an input from a user and commanding the vibrators or other motors and light sources of the invention to operate in any desired modes, which are further defined herein. Computer readable non transitory memory 502 may be integral with the controller 501, such as "on-board memory" as is known in electrical arts, or may be one or more separate memory devices in electrical communication with controller 501. Computer readable non transitory memory 502 may be utilized to store pre-programmed modes of operation and to store other computer readable information as may be required by controller 501. Battery 503 is in electrical communication with and provides power to drive controller 501, memory 502, clitoral light source group 302, clitoral vibrator 304, vaginal vibrator 204, vaginal light source group 202, and any other electrical devices of the invention. Battery 503 may drive these devices directly or may drive them through their electrical connection with controller 501. Battery 503 may also be in electrical communication with charge circuit 506, which may condition power received through charging port connector 451. Alternatively, charging port connector 451 may be in direct communication with battery 503 for directly charging the battery. Battery 503 may also be in electrical communication with inductive charging circuit 505, which may be adapted to produce a charging current when placed in proximity with magnetic field, as is known in the art of inductive charging circuits. In a further alternate embodiment, not shown in FIG. 8A, battery 503 may comprise a replaceable battery or group of batteries, such that they are replaced with a new battery or group of batteries when a given discharge level is reached, for example, when battery 503 is no longer able to power the improved sexual stimulation device 100 of the invention to a user's satisfaction. In any of the embodiments described herein, battery 503 may be a single battery or a group of batteries. Also, the electrical connection at charging port connector 451 may be any connector suitable to fit within the envelope of the invention and provide electrical communication as described herein. Thus, any type of electrical connector, whether a standard connector or a custom connector, may be used and is therefore within the scope of the claims. In a still further embodiment, charging port connector 451 may be in electrical communication with controller 501 such that modes of operation, firmware for operation of the vibrators and light sources of the invention, programming of keypad button functions, and other programmable aspects of the invention may be download and or uploaded and used by controller 501 and stored in memory 502. Thus, charging port connector 451 may also be a programming port.

Still referring to FIG. 8A, controller 501 may further comprise an infrared or RF wireless interface such as, for example, the interface known as Bluetooth®, the interface known as WiFi, the interface known as Near Field Communications (NFC) or any other wireless interface as is known by persons of ordinary skill in the art, in order to wirelessly control the invention and download new or changed modes of operation information and or other information and the like to be stored in either controller 501 or memory 502, or the like. Any type of information may be downloaded and stored in this manner. Such wireless interfaces are well known in the electronic arts and, as such, do not require undue experimentation to understand and implement.

Still referring to FIG. 8A, controller 501 may be in electrical communication with a vaginal light source group 202 through vaginal finger wires 448 (not shown in FIG. 8A), a clitoral light source group 302 through clitoral finger wires 443 (not shown in FIG. 8A), a vaginal vibrator 204 through vaginal finger wires 448 (not shown in FIG. 8), and a clitoral vibrator 304 through clitoral finger wires 443. These devices may be powered off, powered on, pulsed, operated continuously, or driven to various levels of output power directly by the circuitry of controller 501, or by drivers 452, 453, 454, or 455 which may be in electrical communication with controller 501, as the user desires. These drivers may be discrete electric circuits or may be incorporated directly in controller 501 as "on-board" drivers. Vaginal light source group 202, clitoral light source group 302, vaginal vibrator 204, and clitoral vibrator 304 may thus be individually commanded by controller 501 to operate in any patterns desired by the user, which patterns may be coordinated in order to achieve a desired stimulation effect in the user. The patterns of control are discussed below.

Still referring to one exemplary embodiment of the invention depicted in FIG. 8A, controller 501, computer readable non transitory memory 502, charge circuit 506, and drivers 452, 453, 454, and 455 may be located on controller printed wiring board 418 (not shown in FIG. 8A), which may be located in handle 400 (not shown in FIG. 8A) along with keypad 403. Battery 503, charging port connector 451 and inductive charging circuit 505 may also be located in the handle 400 (not shown in FIG. 8A), and may be connected through discrete wires preferably with solder attachments. Vaginal vibrator 204 and vaginal light source group 202 may be located in vaginal finger 200 (not shown in FIG. 8A) and clitoral vibrator 304 and clitoral light source group 302 may be located in clitoral finger 300 (not shown in FIG. 8A). In alternate embodiments of the invention, the various components comprising the invention may be located in any location within the invention and interconnected electrically as is conceivable by the techniques and methods known by persons of ordinary skill in the electro-mechanical arts. Such alternate embodiments are within the scope of the claims, as are equivalent structures and components.

Still referring to FIG. 8A, in the second and third physical embodiments of the invention, clitoral light source group 302, clitoral vibrator 304, and drivers 452 and 454 are not present in the invention, as there is no clitoral finger in the second and third physical embodiments of the invention.

Still referring to FIG. 8A, the invention may, but does not necessarily, comprise optional transceiver 507. Transceiver 507 may be in electrical communication with controller 501 either directly or indirectly, and may be any wireless RF or optical transceiver capable of receiving and/or transmitting RF energy and data to or from the optional remote pulse oximeter(s) of the invention (described below). If transceiver 507 is an RF transceiver, it may communicate with the optional remote pulse oximeter(s) of the invention by using any data channel, physical later or communication protocol known in the arts for RF data communication such as WiFi, Bluetooth®, Near Field Communication (NFC), or any data channel which may comprise analog or digital communications channels. Likewise, if transceiver 507 is an optical transceiver, it may communicate with the optional remote pulse oximeter(s) of the invention by using any data channel, physical later or communication protocol known in the arts for optical data communication including infrared or any other optical wavelength.

Still referring to FIG. 8A, any of the first, second or third physical embodiments of the invention may comprise optional second vaginal light source group 203, which emits vaginal light energy 201 and is in electrical communication with drive 458, which in turn is in electrical communication with controller 501 such that optional second vaginal light source group 203 may be controlled by controller 501 as described herein.

Still referring to FIG. 8A, any of physical embodiments of the invention may comprise optional pulse oximeter circuitry 875, pulse oximeter transmitter 801, and pulse oximeter receiver 802. Pulse oximeter circuitry 875 maybe in electrical communication with controller 501 and with battery 503 in those embodiments of the invention which comprise a reflective pulse oximeter. Pulse oximeter circuitry 875 may comprise a controller or microprocessor in electrical communication with non transitory computer readable memory which may contain instructions for operation of the pulse oximeter as commanded by controller 501. At least one pulse oximeter light source 801, but preferably at least two pulse oximeter light sources 801 as described herein may be in electrical communication with pulse oximeter circuitry 875 and may emit pulse oximeter emitted light D to be reflected from the body of a user as pulse oximeter reflected light E. Likewise, at least one but preferably at least two pulse oximeter light sensors 802 as described herein may be in electrical communication with pulse oximeter circuitry 875 and may receive pulse oximeter reflected light E.

Still referring to FIG. 8A, any of physical embodiments of the invention may comprise optional pressure sensor 1200. Pressure sensor 1200 maybe in electrical communication with controller 501 and with battery 503. Pressure sensor 1200 may comprise a controller or microprocessor in electrical communication with non-transitory computer readable memory which may contain instructions for operation of the pressure sensor as commanded by controller 501. Pressure sensor 1200 may be located in any surface of the invention but is preferably located in vaginal finger 200.

Still referring to FIG. 8A, any of physical embodiments of the invention may comprise optional EMG sensor 877. EMG sensor 877 maybe in electrical communication with controller 501 and with battery 503. EMG sensor 877 may comprise a controller or microprocessor in electrical communication with non-transitory computer readable memory which may contain instructions for operation of the EMG sensor as commanded by controller 501.

Figure 8B:
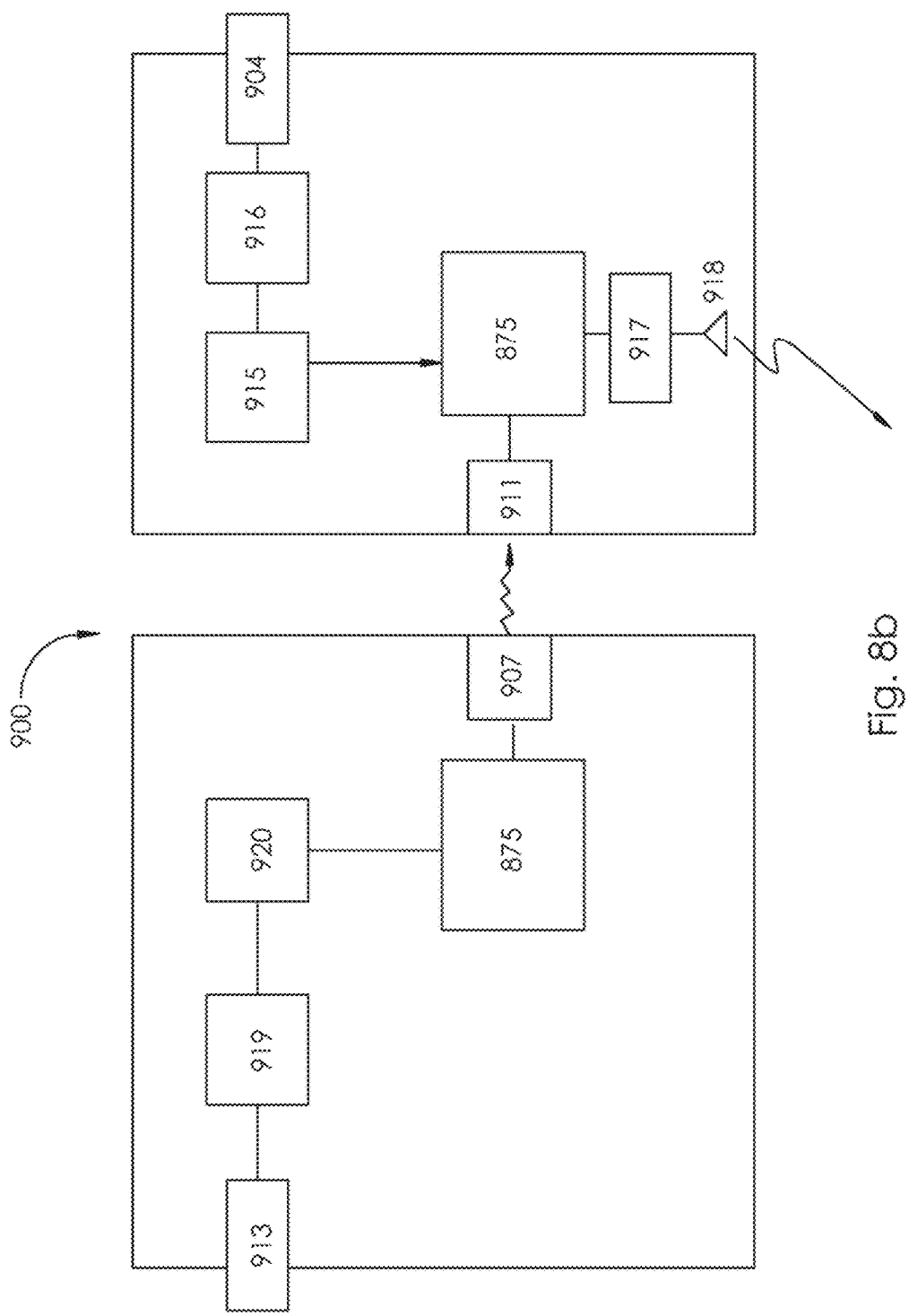
FIG. 8B depicts a functional block diagram of a remote transmissive pulse oximeter embodiment of the invention in which the pulse oximeter is located remotely, i.e. is not located in the vaginal finger, clitoral finger or handle of the invention.

Referring now to FIG. 8B, an electrical diagram of a remote sensor of the invention is depicted. The remote physiologic sensor may be any sensor as defined herein, but may be, for example, a pulse oximeter sensor. In the embodiment in which the remote sensor is a transmissive pulse oximeter sensor, pulse oximeter sensor circuitry 875 may be in electrical communication with pulse oximeter light sources 907 which transmit light energy that is received by pulse oximeter light sources 911. Body tissue of a user, such as an ear lobe or a finger, may be placed between oximeter light sources 907 and pulse oximeter light sources 911. Battery 920 may provide power to the electrical circuit elements of the remote sensor on one side of the transmissive sensor, and battery 915 may provide power to the electrical circuit elements of the remote sensor on the other side of the transmissive sensor. Batteries 915 and 920 may be charged by applying charging current through connectors 904 and 915 and charging circuitry 916 and 919, respectively. Blood oxygen saturation and pulse rate information may be transmitted from transceiver 917 through antenna 918 to a paired transceiver that is in RF or optical communication with transceiver 917 and which resides in, for example, handle 400 (not shown in FIG. 8B) and that is in electrical communication with controller 501. In this manner, sensed Blood oxygen saturation and pulse rate information may be transmitted from the remote sensor to controller 501.

Figure 8C:
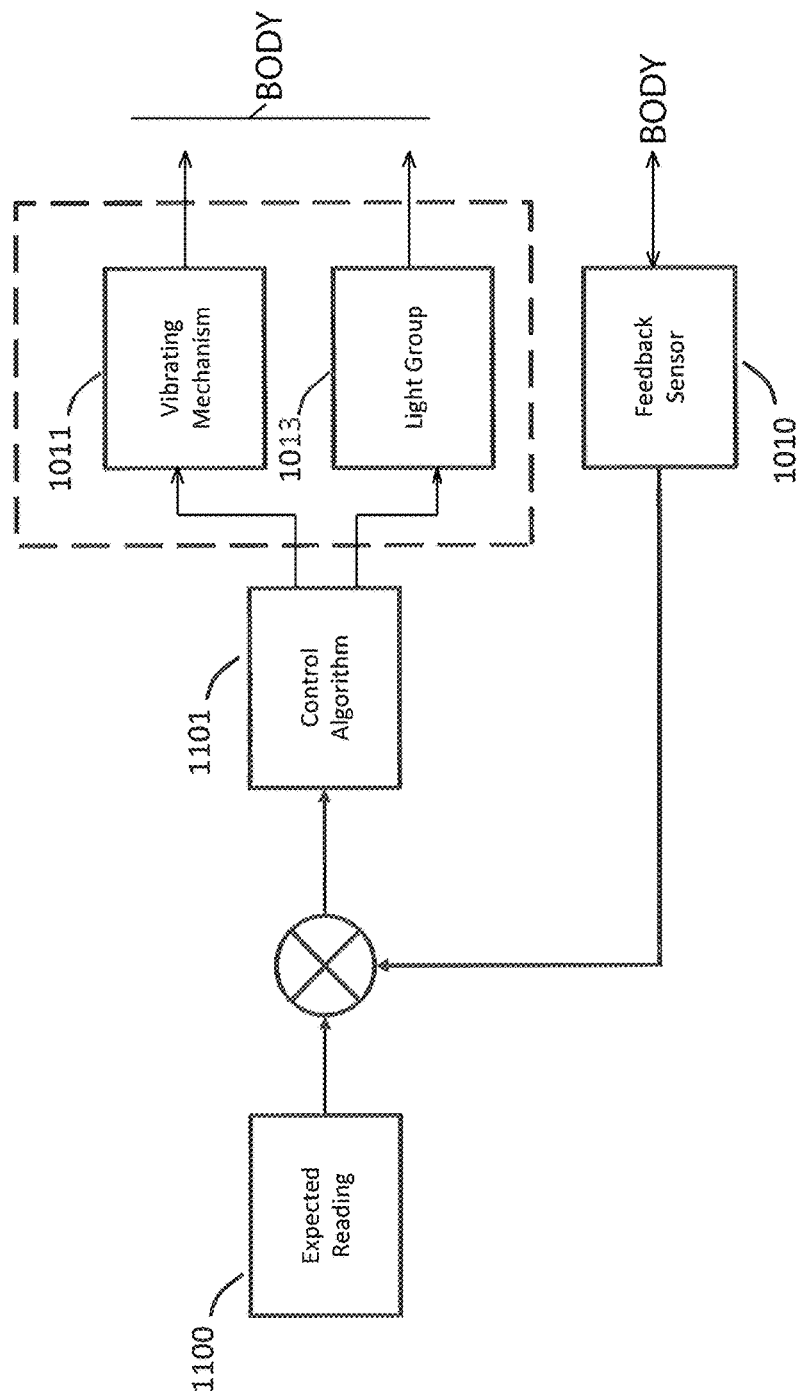
FIG. 8C depicts a feedback loop of the invention.

Referring now to FIG. 8C, a feedback loop of the invention is depicted. A predetermined, expected physiologic parameter 1100 may be stored in computer readable non transitory memory 502 (not shown in FIG. 8C). Physiologic sensor(s) 1010 provide sensed physiologic parameter information to controller 501 (not shown in FIG. 8C). Controller 501 compares the sensed physiologic parameter information to the predetermined, expected physiologic parameter 1100 and determines a variance therebetween, and, using the variance as compared to an expected variance or range of variances, controls parameters of sexual stimulation by controlling mechanical stimulation 1011 and/or light stimulation 1013 in order to achieve a desired sexual stimulation effect on a user.

Alternate Embodiment of the Light Sources of the Invention

Figure 14A:
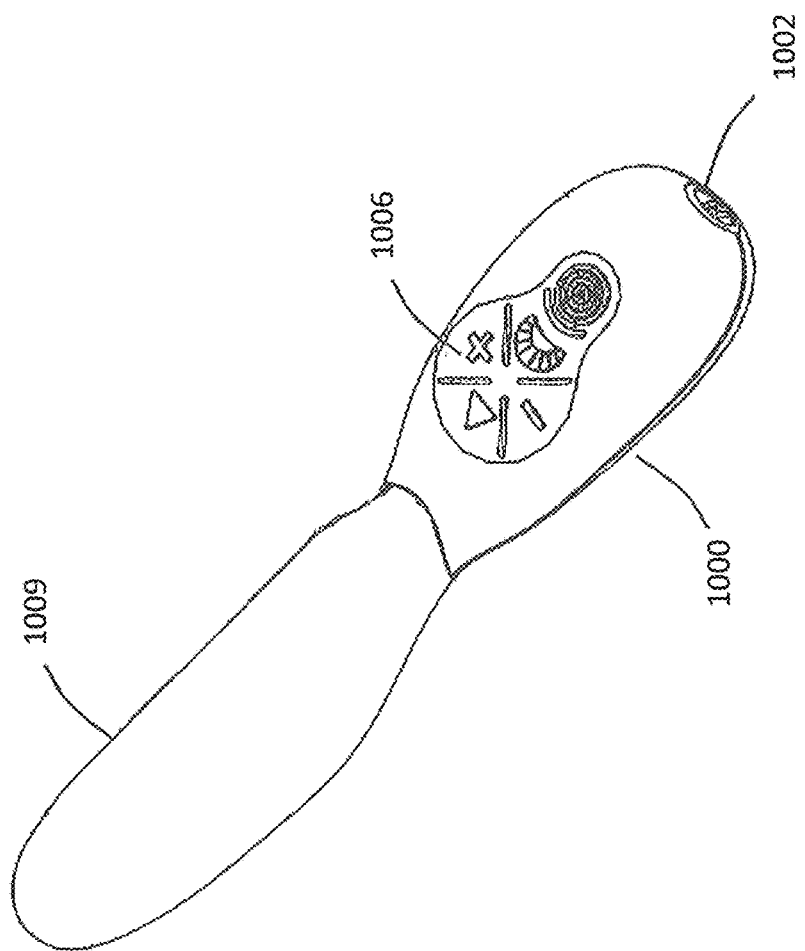
FIG. 14a depicts a perspective view of an embodiment of the invention comprising a vaginal finger and a handle portion.

Referring now to FIG. 14A a cross-sectional view of an alternate embodiment of the improved sexual stimulation device of the invention is depicted in which an optional second vaginal light source group 203, which may comprise a second vaginal finger printed wiring board 207 comprising at least one, or any combination of, three vaginal light sources 202a, 202b and 202c as depicted in FIG. 7A which may radiate a second vaginal light energy 201 onto the posterior vaginal wall of the user, with the beneficial physiological effects hereinbefore described. Optional second vaginal light source group 203 is defined in the paragraphs directed to FIG. 7A hereinabove.

Still referring to FIG. 14A, keypad 403 is shown as being pressed by the finger of a user by depressing, for example, third depressible control button 407 which causes a keypad button nipple 428 to depress and activate the corresponding switch 500, which is mounted on controller printed wiring board 418. Thus a user may command and operate the improved sexual stimulation device of the invention as desired by turning it on or off, manually changing modes, and commanding pre-programmed modes of operation, or the like. Battery 503 may be sandwiched in place between the underside of controller printed wiring board 418 and battery support structure 433, and may be electrically connected with battery wires 436 to controller printed wiring board 418 by a solder or other standard technique for making electrically conductive connection. Battery 503 may further comprise a battery compressive covering 437, or layers of compressive material fabricated from any suitable compressive material, so that it is sandwiched and held in place between the underside of controller printed wiring board 418 and battery support structure 433 with a compressive fit to prevent movement of the battery during shipping and use. Controller printed wiring board connector 446 is electrically connected 509 to laser diode or light emitting diode 510. Light tubes or light transmitting laser fibers 511 are connected directly to the diode 510. These laser fibers or light tubes transmit the light energy to the windows 514 in the vaginal finger 200. The fibers are secured in place by tube terminal boards 514 that are held in place by fasteners 515.

Still referring to FIG. 14A flexible cover 402 covers vaginal finger 200 with a slight compressive fit, and may be further captured in place by flexible cover retaining step 449 which may be received by a matching groove in main support structure 412 and rear handle cover 413 as shown in FIG. 12. Further, Vaginal vibrator 204 may be supported on its underneath side by vaginal finger vibrator retaining structure 440 when vaginal finger rear cover plate 411 is attached in place to vaginal vibrator 204 is further held in place by main support structure vaginal supports 441. Vaginal vibrator 204 may be engaged with main support structure vaginal vibrator supports 441 with a press fit engagement and for further retention may be bonded into place with adhesives. Vaginal finger printed wiring board 207 is held in place by vaginal printed wiring board fasteners 450 which are received by holes in main support structure 412 and which are adapted to receive vaginal printed wiring board fasteners 450, which may be standard threaded fasteners, self-tapping or any other fastener type known in the art. When tube terminal board 514 is mounted as shown, vaginal light energy 201 from light tube or laser fiber source group 511 may exit vaginal finger 200 by passing through flexible cover 402 which is transmissive at light frequencies stated herein. Vaginal finger light tubes or laser fibers 511 establish connection between tube terminal boards 514 and laser diode or light emitting diode 510. Vaginal finger wires 448 establish electrical connection between vaginal vibrator 204, and controller printed wiring board 418. Charging port connector 451 is electrically and mechanically attached to USB port printed wiring board 417, and protrudes through an opening formed in handle front cover plate 410 and handle rear cover 413 when they are assembled as described herein.

Figure 14B:
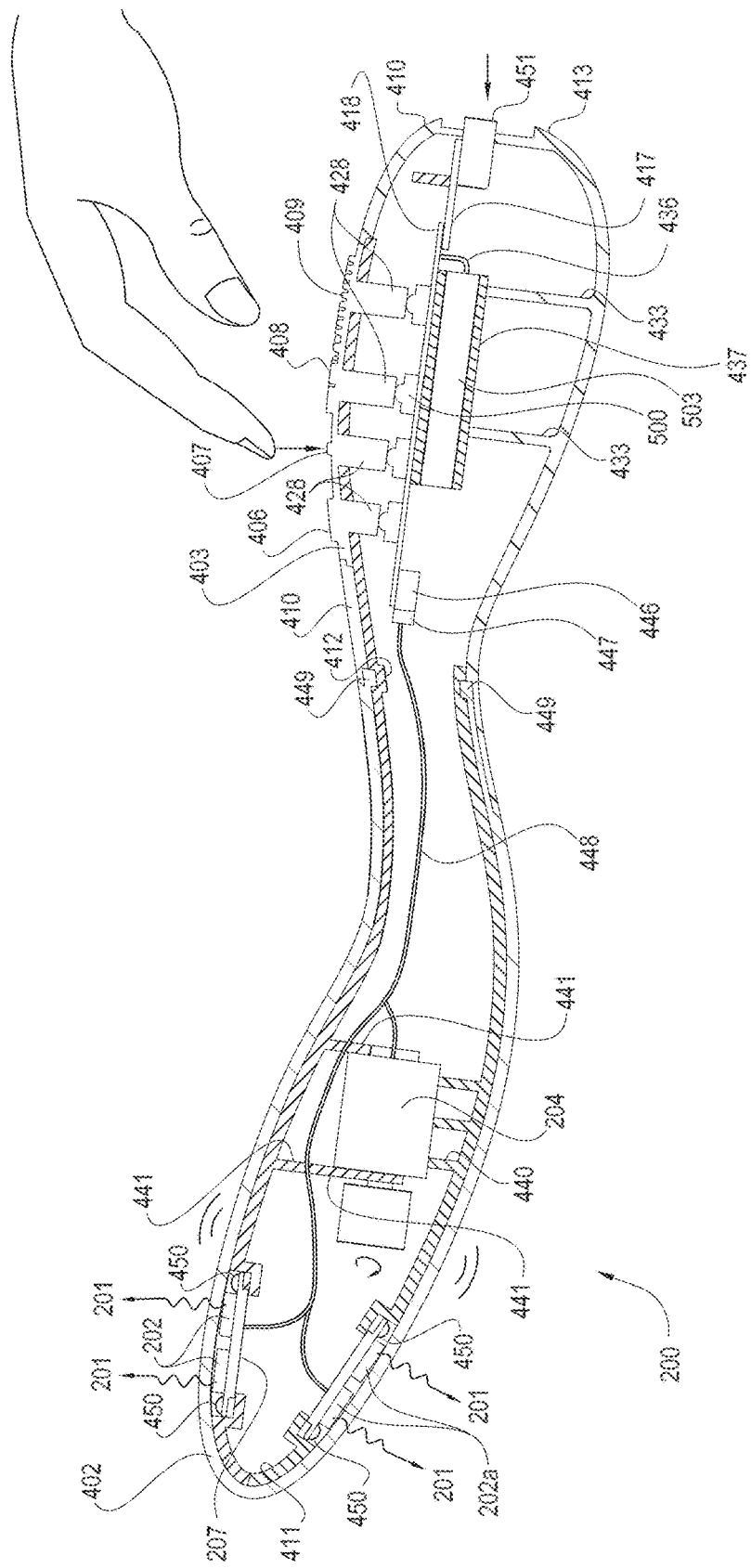
FIG. 14b depicts a cross sectional view of the second physical embodiment of the invention, in which an optional second vaginal light source group radiates therapeutic light energy.
Figure 14C:
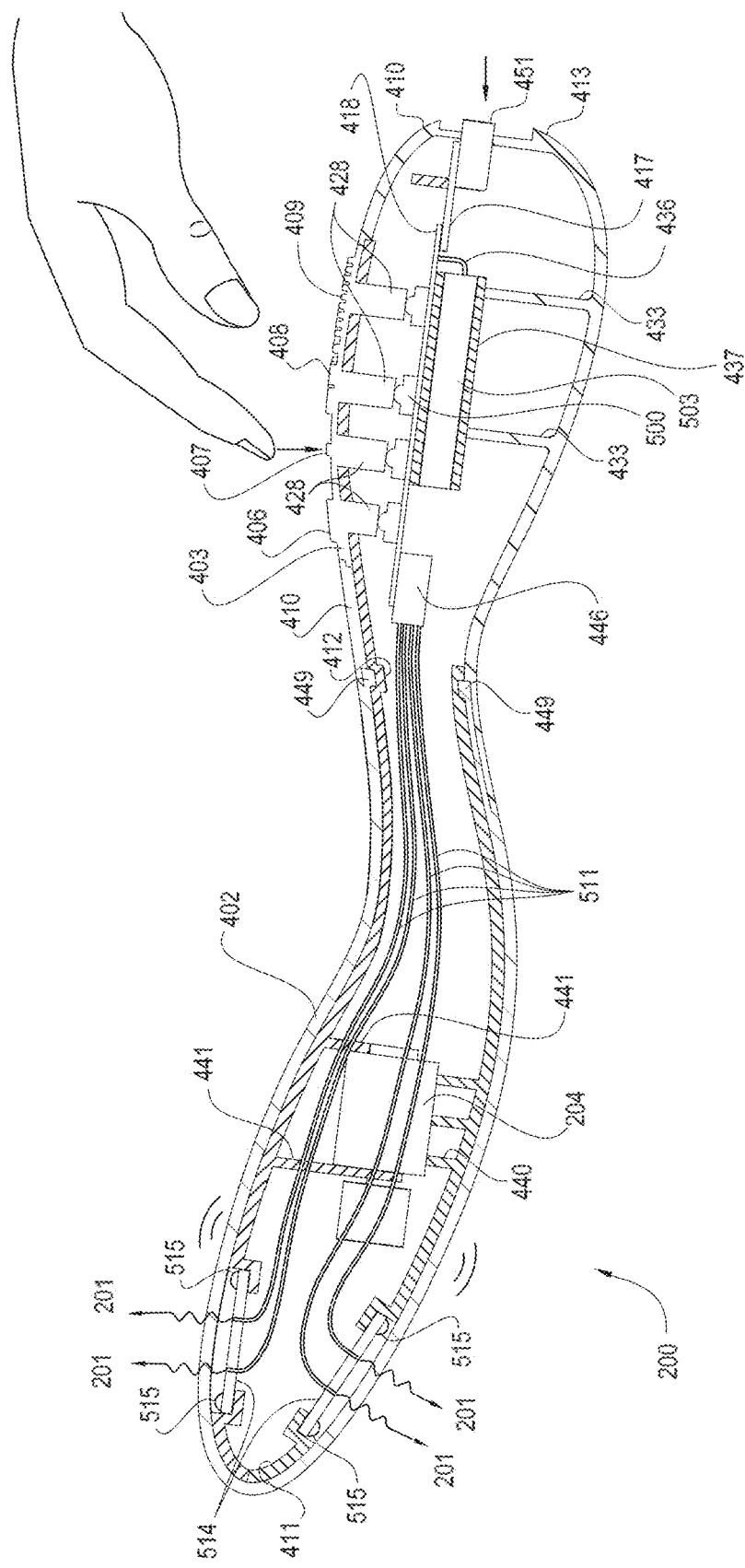
FIG. 14c depicts a cross sectional view of the second physical embodiment of the invention, in which vaginal light source groups comprise light sources located in the handle of the invention, and wherein light energy is transmitted to the vaginal finger and radiated onto the vaginal tissue of a user via light tubes, which may be but are not necessarily optical fibers.
Figure 15:
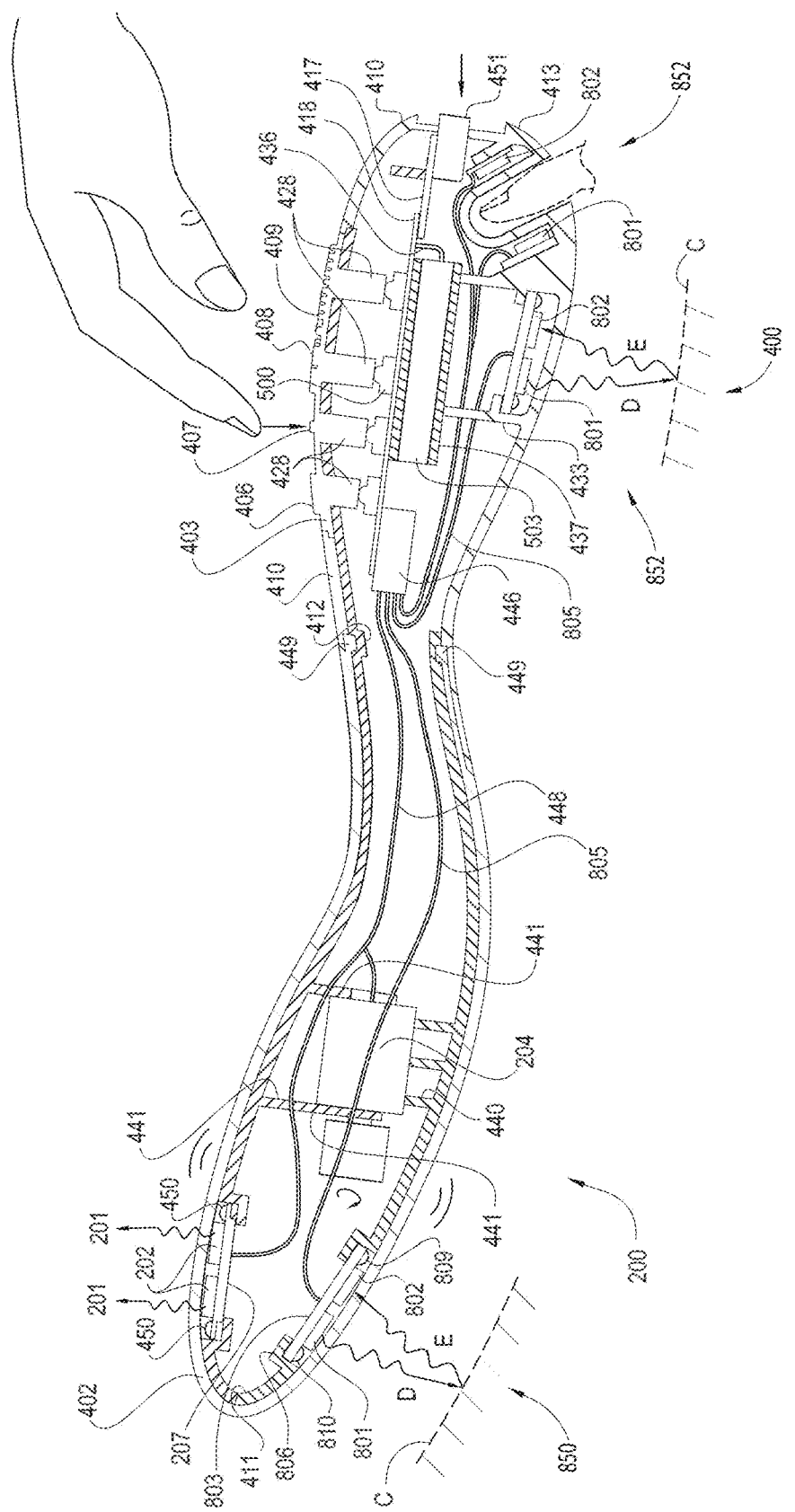
FIG. 15 depicts an embodiment of the invention in which a pulse oximeter may be located in one or several locations in the vaginal finger or handle of the invention.

Referring now to FIG. 14B a cross-sectional view of an alternate embodiment of the improved sexual stimulation device of the invention is depicted in which the optical light sources are located in handle 400, and may be, but not necessarily, specifically located on controller printed wiring board 418. In this alternate embodiment of the invention, light energy is transmitted from optical sources of energy such as, for example, light emitting diodes or laser diodes, located in handle 400 via light tubes 511 which may be, for example, optical fibers. Light energy may be couple into light tubes 511. Light tubes 511 may run to vaginal light tube termination board 514, where they are terminated and retained by any means known in the art, for instance, chemical bonding by bonding the outer diameter of the light tube to the inner diameter of a hole through vaginal light tube termination board 514 which is adapted to accept a light tube 511 such that light tube 511 may be inserted into the hole and may traverse the cross section of vaginal light tube termination board 514. The light tube 511 may be chemically bonded to vaginal light tube termination board 514 while it is disposed thus in the hole in vaginal light tube termination board 514. The terminated end of light tubes 511 are optically transmissive, for instance cleaved optical fiber ends which may also optionally be polished, such that light energy coupled into light tubes 511 from the light energy sources in handle 400 is radiated as vaginal light energy 201. While FIG. 15 depicts two vaginal light tube termination boards 514, one radiating posteriorly one radiating anteriorly, the invention may comprise either one or both of vaginal light tube termination boards 514 radiating in either direction. Furthermore, the invention may comprise one vaginal light source group 202 or 203 on a vaginal finger printed wiring board 207 and one vaginal light tube termination board 514. In other words all combinations of vaginal light sources described herein, any of which may radiate posteriorly or anteriorly, are within the scope of the invention.

Referring now to FIG. 15, a reference view of a female user in which 12 o'clock, 3 o'clock, 6 o'clock and 9 o'clock orientations are depicted for reference.

Alternate Embodiment of the Mechanical Stimulation Sources of the Invention

In a yet further alternate embodiment of the invention, the mechanical simulation of the vaginal finger may comprise any of the means for mechanical stimulation described hereinabove, such as, for instance, an offset vibrator motor, in which the mechanical stimulation means is located in handle 400. Such an embodiment may further comprise a rigid or semi-rigid elongate structure attached to the means for mechanical stimulation and extending into the vaginal finger such that it transmits mechanical energy to vaginal finger 200, enabling a user to perceive vaginal mechanical stimulation when the invention is slidingly engaged with the vagina of the user.

Description of the Physiological Sensor Embodiments of the Invention

It is one feature of the invention to utilize information from physiologic sensors to provide physiological feedback to control the parameters of the vibration and/or light stimulation provided to a user by the invention. Thus the invention may comprise various physiological sensors, or combinations of sensors, which perform the function of sensing or measuring certain physiologic conditions or measuring biometric data. The physiological information processed by the physiological sensors may then be communicated to controller 501 by wires, optically, or wirelessly, where computer instructions, which may be stored in non-transitory computer readable memory 502, may be executed by controller 501, which is in communication with the means for mechanical stimulation and light sources of the invention, thus allowing controller 501 to control of the mechanical stimulation and light energy by controlling such parameters as on state, off state, intensity, frequency, pulsed operation, shapes of pulses, and various waveforms such as sinusoidal or otherwise to achieve a desired sexual stimulation effect on the user in response to the measured physiological information.

The invention may comprise various physiologic sensors such as, for example, pulse oximeter sensors, electromyography sensors, pressure sensors or other sensors either alone or in any combination. The sensors may disposed in the invention in vaginal finger 200, clitoral finger 300, or handle portion 400; or, alternatively or in combination with the foregoing, the sensors may be remote sensors that are clipped onto a user's finger or ear, strapped to a user's abdomen using a belt or other wearable device or are located in sensing proximity to any part of user's body. In the case of the remote sensors, such remote sensors may be in wireless communication with controller 501 by any wireless communication means known in the art which may include, by way of example, radio frequency (RF) communication such as the standards known as WiFi, Bluetooth, or Near Field Communication (NFC); may be any RF wireless link; may be an optical link; or may be a wired link in which the remote sensors are connected to the sexual stimulation device of the invention by electrically conductive wires using connectors and wires as is known in the electrical arts. In the remote sensor embodiments comprising optical wireless communication, both the remote sensor and the sexual stimulation device of the invention further comprise optical transceivers. The remote sensing device comprises an optical transceiver in electrical communication with a power source such as a battery, and is also in electrical communication with the sensor element.

The invention may comprise one or a plurality of sensors that measure any one of, or any combination of, biometric parameters of a user which may include pulse rate, blood oxygen saturation, blood pressure, temperature, electrical activity, or other biometric parameters. The invention may comprise any one, any plurality or any combination of these sensors in any of the first physical embodiment, second physical embodiment or third physical embodiment of the invention described herein. Furthermore, each of these alternate embodiments may also comprise a source of auditory stimulation, such as a speaker. The invention may comprise any of the first, second or third physical embodiments, light sources, mechanical stimulation sources, and auditory sources described herein, in any combination.

In any embodiment of the invention, the user of the invention may have the option to deactivate the sensor or sensors of the invention by entering commands on the keypad causing the execution of program instructions stored in non-transitory computer readable memory that operate to cause the microprocessor or microcontroller of the invention to ignore measurements from the sensor or sensors. Likewise, the user of the invention may have option to deactivate the sensor or sensors of the invention by entering commands on the keypad causing the execution of program instructions stored in non-transitory computer readable memory that operate to cause the microprocessor or microcontroller of the invention to refrain from issuing alerts in the form of auditory, visual or vibrotactile alerts from the invention.

The sexual stimulation device and remote sensors may also comprise a means of alerting the user that a pre-defined physiological state has been achieved. Such means of alerting may comprise a source of sound in order to provide an audio alert; a source of light in order to provide a visual alert; a source of tactile alert that applies a tactile alert or buzz to the user; or any combination of these means for alerting a user. The source of sound may be a speaker, buzzer, or any device known in the art to emit sound upon application of a signal. The source of light may be an LED, laser diode or any device known in the art to emit light upon application of a signal. The source of tactile energy may be a vibrotactile transducer, vibrator motor, or any device known in the art to cause tactile sensation in a user upon application of a signal. The one or more means for alert are in communication with controller 501 either directly or indirectly by wired electrical conductors or wirelessly, and may also be in electrical communication with battery 503, or in the case of means for alert that are disposed in a remote sensor, the means for alert may be in electrical communication with a batter housed within the remote sensor.

Pulse Oximeter Sensor Embodiments of the Invention

Figure 17:
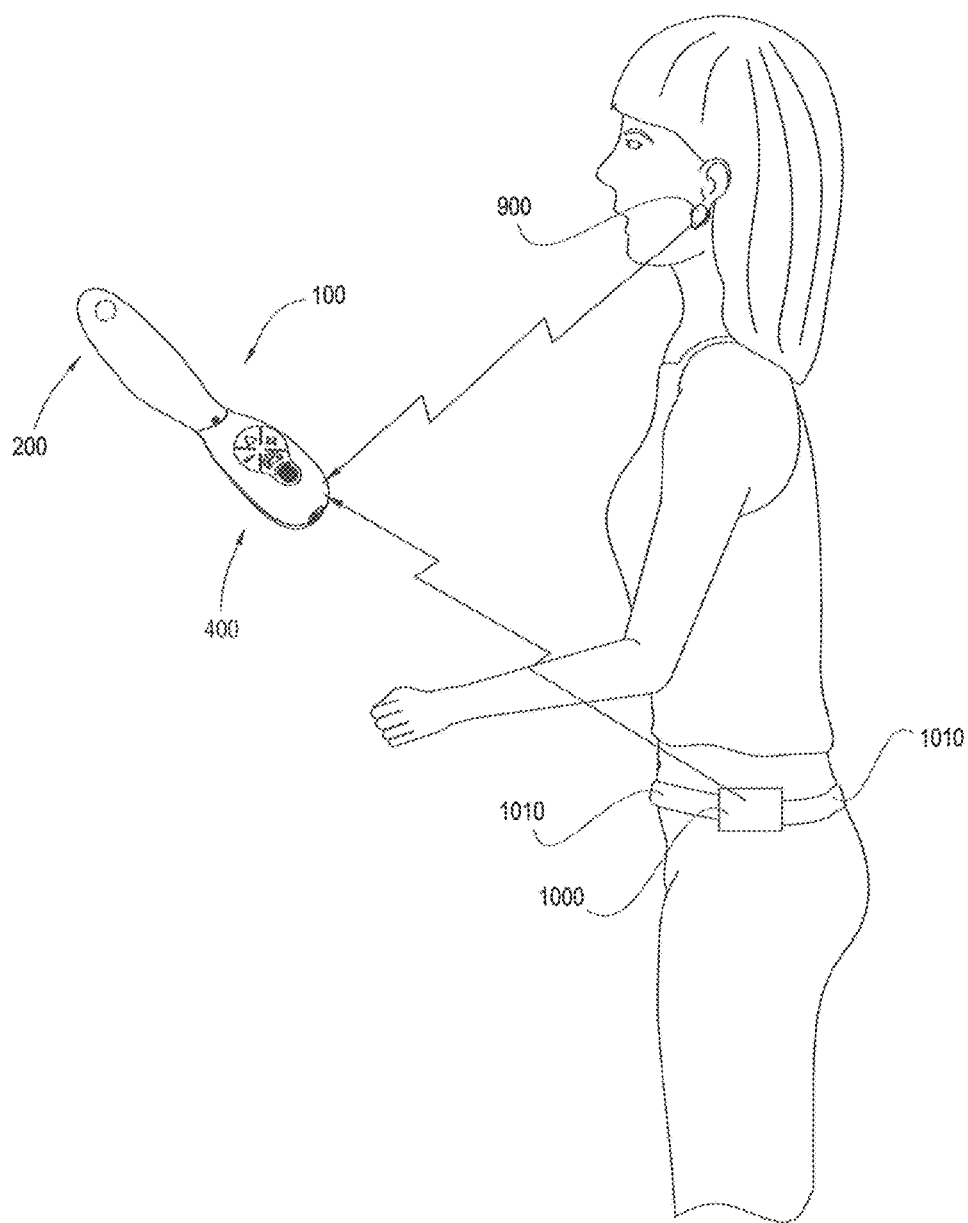
FIG. 17 depicts a system view of an embodiment of the invention which comprises remote sensors, which may be on or more pulse oximeters, which may be worn on the earlobe or abdomen of a user, and which communicate with the controller of the invention via an RF or optical data link.

Referring now to FIGS. 15, 17, 18A, 18B, 19A and 19B, the invention may comprise one pulse oximeter sensor or a plurality of pulse oximeter sensors for measuring physiological conditions such as heart rate, oxygen saturation level of the blood, or both. The pulse oximeter sensor or sensors may be located in vaginal finger 200 or in handle 400 as is depicted in FIGS. 15 and 17, or may be disposed remotely as depicted in the clip sensor of FIGS. 18A and 18B or in the belt-worn sensor of FIGS. 19A and 19B. As used herein, "pulse oximeter sensor" means any type of pulse oximeter sensor presently known in the medical arts. Pulse oximeter sensors may measure the absorption or reflection of light, which may be red and infrared light, by pulsatile blood. Pulse oximeter sensors operate on the principle that oxygenated blood absorbs light of specific frequencies at a level determined by the level of oxygenation of the blood. As an example, oxygenated blood absorbs light preferentially at 660 nm (red light), whereas deoxygenated blood absorbs light preferentially at 940 nm (infra-red). Pulse oximeter sensors may comprise one or more light sources which may be diode lasers or light emitting diodes. The pulse oximeters of the invention may comprise one laser diode or one LED transmitting at 600 nm, and one laser diode or one LED transmitting at 940 nm. The pulse oximeters of the invention may further comprise one or a plurality, for example, two, pulse oximeter light sensors 802 such as photodiodes which measure the amount of red and/or infra-red light traversed by or reflected from a user's body tissues from one or a plurality of pulse oximeter light sources 801. The relative absorption of light by oxyhemoglobin (HbO) and deoxyhemoglobin in the user is processed by the pulse oximeter sensor by measuring the level of reflected or transmitted light at each frequency, and an using the measured levels to determine oxygen saturation level by algorithms known in the art. The pulse oximeter sensor is typically adapted to ignore local noise from the tissues. The result is a continuous qualitative measurement of the patient's oxyhemoglobin status or blood oxygenation level; pulse rate can also be measured by, for example, the pulse oximeter measuring the timing of the surges of blood in the user. Pulse oximeter sensors known in the art may thus deliver physiological information about the pulse rate, oxygen saturation (SpO2) and even cardiac output of the user. The pulse oximeter sensors known in the art are generally available in two varieties: reflective and transmissive. Reflective pulse oximeter sensors measure light reflected from body tissue; transmissive pulse oximeter sensors measure light transmitted through body tissue, such as, for example, a finger. In an alternative embodiment the reflective sensor may utilize visible or non-visible light other than red and infrared.

Although the invention may comprise both transmissive and reflective pulse oximeter sensors, the preferred sensor comprising the present invention is a reflective sensor. The preferred reflective pulse oximeter sensor or sensors may be independently chosen from the group of pulse oximeter sensors known in the art that utilize photoplethysmography to estimate heart rate and hemoglobin oxygen saturation. The reflective pulse oximeter sensor or sensors may be disposed anywhere on the invention that allows light energy from the pulse oximeter to be transmitted onto the body of the user and reflected back so that the pulse oximeter of the invention may make the aforementioned measurements. Preferably, the pulse oximeter of the invention may be disposed 1) on a surface of vaginal finger 200, or under an optically transmissive window disposed in vaginal finger 200, allowing the transmission and reception of light by the pulse oximeter; 2) in a recess in handle 400 such that a user may insert a finger, such as an index finger, into the recess allowing the aforementioned physiological information to be processed by the pulse oximeter; or 3) remotely in a wearable configuration such as may be clipped onto a user's finger or earlobe (FIGS. 18A and 18B), or worn in a belt on the user's abdomen or other part of the user's body (FIGS. 19A and 19B).

The pulse oximeter sensor or sensors may be in electrical communication with controller 501 of the invention, either directly or indirectly, for instance through a serial peripheral interface bus, conditioning circuitry or other interface circuitry as may be required to adapt the sensor input and output to the controller and allowing measured physiological conditions such as heart rate and blood oxygen saturation levels to be communicated to the microcontroller or microprocessor of the invention. The controller 501 of the invention may execute computer-readable program instructions stored in the non-transitory computer readable memory of the invention using the measured physiological information as described above to control the level, intensity, waveform and ON/OFF timing of the application of vaginal and/or clitoral mechanical stimulation, vaginal and/or clitoral light energy, auditory stimulation, or any combination thereof as may be provided by the invention to the body of the user. Such desired level of stimulation may be modulated by the invention to achieve a desired effect on the user utilizing the measured physiological condition of the user as a constant or repetitive input, and allowing closed-loop control of the mechanical stimulation, therapeutic light stimulation, and/or auditory stimulation of the invention to produce a desired effect on the user. Such desired effect may be, for example, a particular level or pattern of heart rate of the user.

Various Physical Embodiments of the Pulse Oximeter of the Invention

Referring now to FIG. 15, three optional locations the pulse oximeter of the invention are depicted: the invention may comprise a pulse oximeter at any one, any combination, or all three locations. In first pulse oximeter embodiment 850 in vaginal finger 200, the invention may comprise a reflective pulse oximeter as shown in FIG. 15 in which pulse oximeter light source 801 transmits light energy D as described above which is reflected from the body surface of a user C, which may be the user's posterior vaginal wall. Reflected light energy E is received by pulse oximeter light sensor 802, and the received signal is processed by pulse oximeter circuitry 875 located on pulse oximeter printed wiring board 803 (not shown in FIG. 15)) as described above, and the processed signal containing pulse rate or oxygen saturation is communicated to controller 510 by pulse oximeter wiring 805.

Still referring to FIG. 15, in a second pulse oximeter embodiment 851 in the handle 400, the invention may comprise a reflective pulse oximeter as shown in FIG. 15 in which pulse oximeter light source 801 transmits light energy D as described above which is reflected from the body surface of a user C, which may be the user's hand. Reflected light energy E is received by pulse oximeter light sensor 802, and the received signal is processed by pulse oximeter circuitry 875 located on pulse oximeter printed wiring board 803 (not shown in FIG. 15) as described above, and the processed signal containing pulse rate or oxygen saturation is communicated to controller 510 by pulse oximeter wiring 805.

Still referring to FIG. 15, in a third pulse oximeter embodiment 852 in the handle 400, the invention may comprise a transmissive pulse oximeter as shown in FIG. 15 in which pulse oximeter light source 801 transmits light energy D as described above which is transmitted through a user's finger which has been inserted into a cavity in handle 400. The light energy D that is transmitted through the user's finger is received by pulse oximeter light sensor 802, and the received signal is processed by pulse oximeter circuitry 875 located on pulse oximeter printed wiring board 803 (not shown in FIG. 15) as described above, and the processed signal containing pulse rate or oxygen saturation is communicated to controller 510 by pulse oximeter wiring 805.

Still referring to FIG. 15, in all three of the above embodiments, first pulse oximeter embodiment 850, second pulse oximeter embodiment 851 and third pulse oximeter embodiment 852 pulse oximeter printed wiring board 803 may be mounted to pulse oximeter mounting flange 806 or similar structure using pulse oximeter printed wiring board mounting hardware 809, or by any other mounting means known in the mechanical arts such as for example, chemical bonding. At least one, but preferably two, pulse oximeter light sources 801 and at least one, but preferably two, pulse oximeter light sensors, which may be photodiodes, 802 may be mounted on pulse oximeter printed wiring board 803 and may be in electrical communication with pulse oximeter circuitry 875 which comprises electrical components capable of executing computer readable instructions stored on non-transitory computer readable memory, all of which may also be mounted onto pulse oximeter printed wiring board 803 and all which may be in electrical communication with one another. Pulse oximeter light source(s) 801 may emit light energy D as described above, which light energy may be reflected from the body surface of user or may be transmitted through a body part of a user such a finger. The reflected light energy E or, in the case of the third pulse oximeter embodiment 852, transmitted light energy D is received by pulse oximeter light sensor(s) 802, which may be photodiodes. The resulting electrical signal may be processed by signal conditioning circuitry such as amplifier (s) and filter(s), then digitized, as is known in the art, and then communicated electrically to pulse oximeter microprocessor or controller, whereupon pulse oximeter microprocessor or controller executes computer readable instructions stored on non-transitory computer readable memory and the resulting digital information which contains information regarding the pulse rate of the user, the oxygen saturation of the user or other physiological information as is known in the pulse oximeter art may be communicated to controller 501 through pulse oximeter wiring 805.

Referring now to FIGS. 17, 18A, 18B, 19A and 19B in yet a further alternative embodiment of the pulse oximeter embodiments of the invention, the pulse oximeter sensor(s) comprising the invention may be remotely disposed in a separate pulse oximeter sensor housing that is adapted to slide onto the finger of a user (not shown in FIG. 17), clip onto the ear of a user using remote clip pulse oximeter 900 or be worn on the user's abdomen as a remote wearable pulse oximeter 1000 by means such as a belt or elastic band 1010. The pulse oximeter sensor may communicate with the controller 501 (not shown in FIG. 17) of the invention 100 directly via electrical wiring, or alternatively may be in communication with controller 501 of the invention wirelessly via any wireless communication means known in the art including but not limited to Radio Frequency means such as the RF standard known as WiFi, Bluetooth, Near Field Communications (NFC), WiFi (IEEE 802.11) or other RF means; or, alternatively, the remote pulse oximeter sensor may communicate with controller 501 via optical means such as an infrared communication link. Wireless communication such as RF and optical wireless communication is well known in the art. Vaginal finger 200 and handle 400 are shown for reference.

Figure 18B:
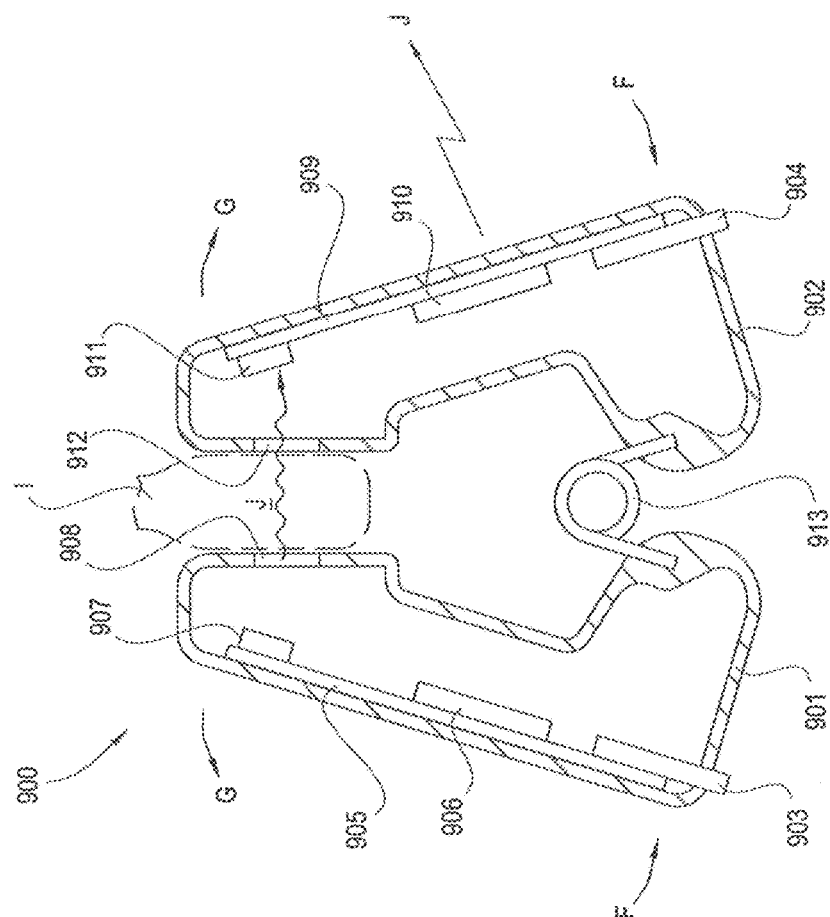
FIG. 18B depicts a cross sectional view of the optional spring-clip pulse oximeter sensor of the invention which may be, but is not necessarily, worn on the ear of a user.
Figure 18A:
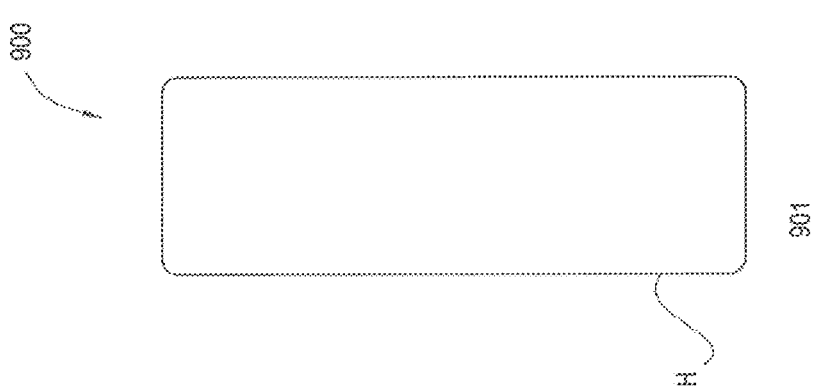
FIG. 18A depicts a front view of the optional spring-clip pulse oximeter sensor of the invention which may be, but is not necessarily, worn on the ear of a user.

Referring now to FIGS. 18A and 18B, an embodiment of the invention in which the pulse oximeter of the invention may be worn on the finger or ear I of a user is depicted. The outside remote clip pulse oximeter shape H of remote clip pulse oximeter 900 may be any shape and is not be limited by the exemplary shape depicted in FIG. 18A. Remote clip pulse oximeter 900, which may be a transmissive pulse oximeter or a reflective pulse oximeter, may be clipped onto any body part of a user, but preferably may be clipped onto a finger or earlobe of a user I, in order to measure pulse rate, blood oxygenation level or any other biometric parameter capable of being measured by the pulse oximeters known in the art, and transmits this physiological information either by wires (not shown in FIG. 18A or 18B) or wirelessly to controller 501 (not depicted in FIG. 18A or 18B).

Referring now specifically to FIG. 18B, a cross section of the transmissive pulse oximeter embodiment of remote clip pulse oximeter 900 of FIG. 18A is depicted. Torsion spring 903 is attached to two housings 901 and 902, which allows a spring-loaded engagement between housings 901 and 902 such that the surfaces containing optically transmissive windows 908 and 912 are forced together by action of spring 903 unless and until a user applies forces F as shown in the figure. When a user applies forces F as shown in the figure with sufficient force to overcome the force of spring 903, the surfaces containing optically transmissive windows 908 and 912 are forced apart in the direction depicted by arrows G, allowing the remote clip pulse oximeter 900 of the invention to be clipped onto a finger, ear or other body part I of a user. First component mounting substrate 905, which be any material including but not limited a printed wiring board or other similar printed circuit substrate, may be attached to an interior surface of housing 901 and may comprise a battery, a battery charging circuit 919 in electrical communication with battery 920, pulse oximeter circuitry 875 in electrical communication with battery 920 and in electrical communication with one or more pulse oximeter light sources 907, shown collectively as 906; and electrical connector 913 in electrical communication battery charging circuit 919 and with pulse oximeter circuitry 875 for receiving charging current and programming information. One or more pulse oximeter light sources 907 radiate pulse oximeter emitted light J through optically transmissive window 908 through the ear, finger or other body part I of the user. The pulse oximeter emitted light J may pass through optically transmissive window 912 in housing 902 where it is received by pulse oximeter light sensor or sensors 911, which may be attached to second component mounting substrate 909, which be any material including but not limited to a printed wiring board or other similar printed circuit substrate. Also located on second component mounting substrate 909 may be a battery 915, a battery charging circuit 916 for charging battery 915 in electrical communication with battery 915, pulse oximeter circuitry 875 as is known in the art which may comprise a controller in electrical communication with the battery and with one or more pulse oximeter light sensors 911, an RF transceiver 917 in electrical communication with pulse oximeter circuitry 875 and antenna 918 or optical transceiver 917 in electrical communication with pulse oximeter circuitry 875, shown collectively as 906 in FIG. 18B; and electrical connector 904 for receiving charging current and programming information. The connectors of the remote clip pulse oximeter 900 may be any connector known in the art such as, by way of example, Mini-USB or Micro-USB connectors. While a particular embodiment of the remote clip pulse oximeter 900 of the invention is depicted in FIGS. 18A and 18B it is understood that the invention may comprise any embodiment of clip-on pulse oximeter known in the art, and the scope of the invention is not to be limited to the exemplary embodiment shown but includes all embodiments of clip-on pulse oximeters known in the art.

Still referring to FIGS. 18A and 18B, it is to be understood that the remote clip pulse oximeter 900 of the invention may be a reflective pulse oximeter, in which case pulse oximeter emitted light J may be reflected by a finger, ear or other body part I of a user to be reflected back through optically transmissive window 908 and to be received by pulse oximeter light sensor or sensors 911, which, in the reflective pulse oximeter case not depicted in FIG. 18B, may be mounted for example on first component mounting substrate 905. In this embodiment, all circuit components described above may be located on first component mounting substrate 905.

Referring now to FIGS. 19A and 19B, an embodiment of a remote pulse oximeter of the invention is depicted. In this embodiment, a remote reflective pulse oximeter is used to measure blood oxygen saturation of a user's torso, stomach or other body surface. A belt 1010 may be used to allow a user to wear the remote pulse oximeter 1000 in sensing proximity to a user as is further depicted in exemplary fashion in FIG. 17. Referring now to FIG. 19B, a cross section of an embodiment reflective pulse oximeter embodiment of the wearable configuration is depicted. Remote pulse oximeter 1000, which may be a reflective pulse oximeter, may comprise a housing 1002, a component mounting substrate 1001, a connector 1005, one or more electronic components comprising pulse oximeter and other circuitry 1006, standoffs 1003, and housing window 1004. Component mounting substrate 1001, which be any material including but not limited a printed wiring board or other similar printed circuit substrate, may be attached to an interior surface of housing 1002 using standoffs or any other known attachment means, and may comprise a battery, a battery charging circuit in electrical communication with battery, pulse oximeter circuitry 875 in electrical communication with battery and in electrical communication with one or more pulse oximeter light sources 1007 emitting pulse oximeter emitted light M through window 1004; and electrical connector 1005 may be in electrical communication battery charging circuit and with pulse oximeter circuitry 875 for receiving charging current and programming information. One or more pulse oximeter light sources 1007 radiate pulse oximeter emitted light M through optically transmissive window 1004 to contact and be reflected from a surface of a user's body L, where it is received by pulse oximeter light sensor 1008. Also, circuitry 1006 may comprise a wireless transceiver, which may be an RF transceiver or an optical transceiver, in electrical communication with pulse oximeter circuitry 875 and an antenna or optical, shown collectively as 1006 in FIG. 19B. The wireless transceiver may also be in wireless data connection with controller 501 through transceiver 507 (not shown in FIGS. 19A and 19B but shown in FIG. 8A. The connector or connectors of the wearable pulse oximeter 1000 may be any connector known in the art such as, by way of example, Mini-USB or Micro-USB connectors. While a particular embodiment of the wearable pulse oximeter 1000 of the invention is depicted in FIGS. 19A and 19B it is understood that the invention may comprise any embodiment of clip-on pulse oximeter known in the art, and the scope of the invention is not to be limited to the exemplary embodiment shown but includes all embodiments of wearable pulse oximeters known in the art. In this manner, the wearable pulse oximeter 1000 of the invention may measure the blood oxygen saturation of a user using reflective pulse oximeter readings, and then may transmit the measured blood oxygen saturation levels of a user to controller 501 for processing and for controlling the parameters of sexual stimulation being applied to a user in response to a user's measured blood oxygen saturation level, as measured by the wearable pulse oximeter of the system.

Exemplary Embodiments of the Electromyography Sensor of the Invention

Figure 20A:
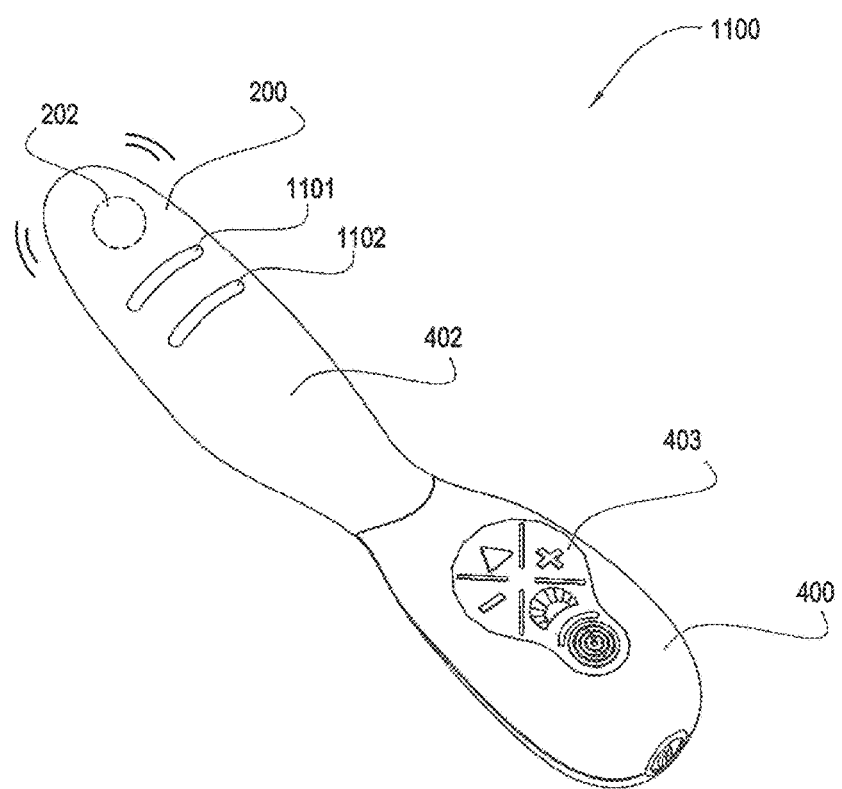
FIG. 20A depicts a front view of the optional EMG sensor of the invention in which the EMG conductors are disposed in the vaginal finger of the invention.
Figure 20B:
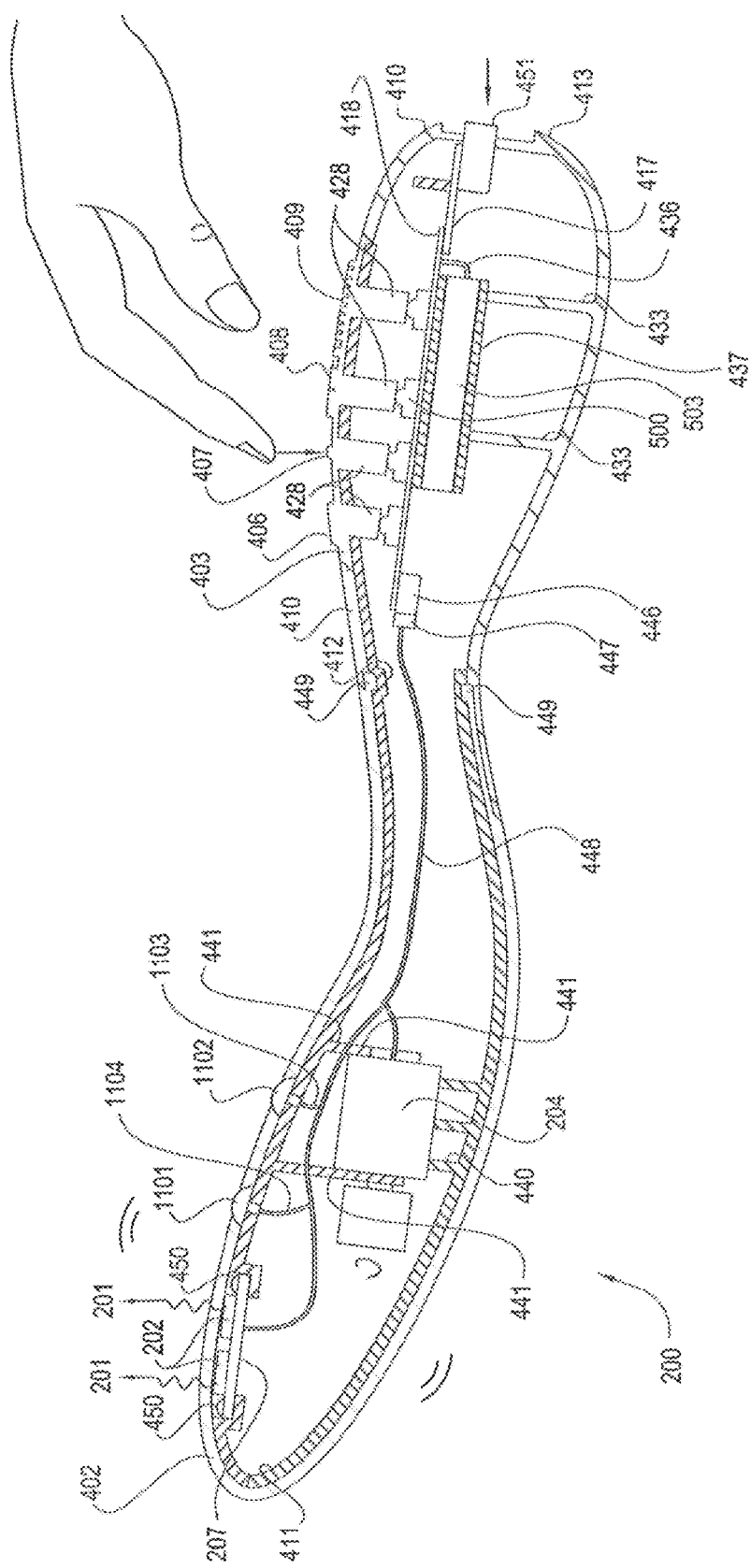
FIG. 20B depicts a cross-sectional view of the optional EMG sensor of the invention in which an optional EMG sensor is disposed in the vaginal finger of the invention.

Referring now to FIGS. 20A and 20B, an alternate embodiment of the ElectroMyoGraphy (EMG) sensor of the invention is depicted. The invention may comprise electromyographic sensors may to measure the electrical activity produced by skeletal muscles, especially intra-vaginal muscles. In a preferred embodiment, surface EMG sensors which comprise a first electrode and second electrode disposed on any outer surface of any of the physical embodiments of the invention may be used to measure skeletal muscle electrical activity. Such skeletal muscle activity may indicate a measure of the physiologic parameter of muscle activation or contraction. When the first electrode and second electrode are disposed on an outer surface of the vaginal finger of the invention, the physiologic parameter of muscle activation or contraction may be measured.

Still referring to FIGS. 20A and 20B, an embodiment of the invention 1100 comprising an EMG sensor is depicted in which the first electrode 1101 and second electrode 1102 are disposed on an outer surface of vaginal finger 200 is depicted. First electrode 1101 and second electrode 1102 are in electrical communication with EMG processing circuitry which may be located on the controller printed wiring board 418 by electrically conductive wires 1104 and 1103. The EMG processing circuitry may be in electrical communication with controller 501. Alternatively, controller 501 may act as EMG processing circuitry by executing non transitory instructions stored in non-transitory computer readable memory 502. Controller 501 may control at least one parameter of sexual stimulation by executing non transitory instructions, using EMG information provided by said EMG processing circuitry, to change at least one parameter of sexual stimulation in response to said EMG information.

Exemplary Embodiments of the Pressure Sensor of the Invention

Figure 21:
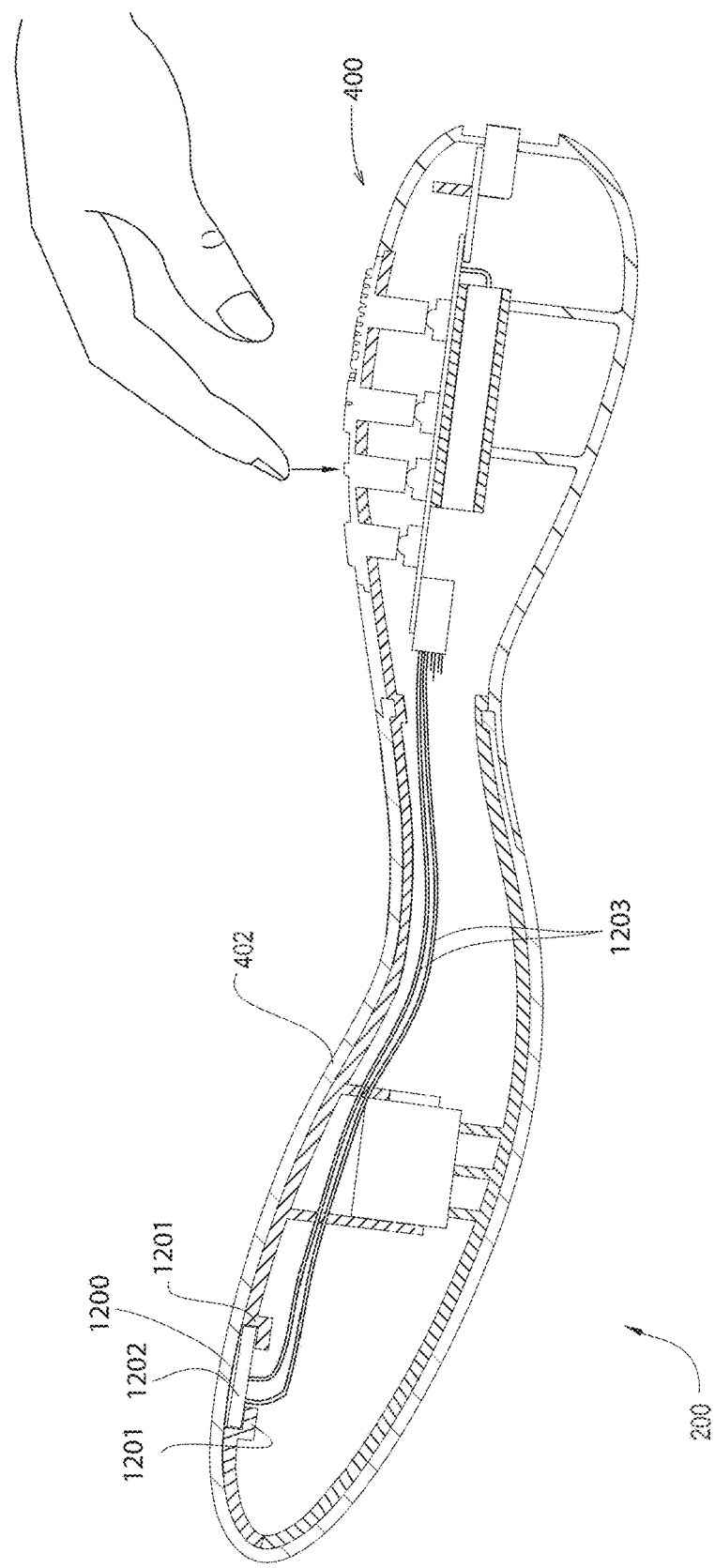
FIG. 21 depicts a cross-sectional view of the optional EMG sensor of the invention in which an optional pressure sensor is disposed in the vaginal finger of the invention.

Referring now to FIG. 21, an embodiment of the invention that comprises an optional pressure sensor 1200 located is depicted. The optional pressure sensor 1200 may be attached to pressure sensor mounting plate 1202 that may be attached to attachment features in main support structure 412. The attachment may be accomplished by any attachment means known in the art. Pressure sensor 1200 may have a pressure sensing surface that is in pressure sensing contact with an interior surface of flexible cover 402, or may be in pressure sensing contact with any other window or cover material, or may be in pressure sensing contact directly with a body surface of a user. Pressure sensor 1200 may be in electrical communication via pressure sensor wiring 1203 with pressure signal processing circuitry that may be, for example, located on controller printed wiring board and which may be in electrical communication with controller 501 such that pressure signal information is processed and communicated to controller 501. In this manner, controller 501 may process signals produced by pressure sensor 1200 so as to determine the pressure by which the vaginal finger of the invention 200 is being pressed against a body surface of a user. The body surface most commonly experiencing the measured pressure would be an internal vaginal surface of a user, but in practice the measured body surface could be any body surface of a user.

Still referring to FIG. 21, it is understood and within the scope of the invention that pressure sensor 1200 may be located on any surface of vaginal finger 200. The location of the pressure shown in FIG. 21 is exemplary only. It is also understand that one, or a plurality, of pressure sensors may be located on any surface of the invention. Thus, as an example of one of many alternate embodiments of the invention, a plurality of pressure sensors may be located on the surfaces of vaginal finger 200. Also an array of pressure sensors may be located on the surfaces of vaginal finger 200, preferably located under flexible cover 402 but in pressure sensing contact with flexible cover 402.

Pressure sensor 1200 may be any pressure sensor known in the art that can sense or measure the contact pressure between two surfaces. Specifically, pressure sensor 1200 measures the contact pressure between the surface of the invention in which pressure sensor 1200 is mounted and a body surface of a user. In a typical scenario at least one pressure sensor 1200, but in the alternative a plurality of pressure sensors 1200, may be located in vaginal finger 200. In a preferred embodiment of the invention, pressure sensor 1200 may be a piezo-resistive or piezo-electric contact pressure sensor. However, pressure sensor 1200 may be any type of contact pressure sensor known in the art such as a microtip, water-charged, air-charged or fiber-optic pressure sensor.

During use, a user may press vaginal finger 200 against an internal vaginal surface of the user's body. The pressure that is applied by the user may vary during the use of the invention, and may be used as an indicator as to which stage of the sexual response cycle a user is experiencing. By sensing the pressure between the sexual stimulation device of the invention and a body surface of user, controller 501 may execute computer readable instructions stored in non-transitory computer readable memory 502 to change at least one parameter of sexual stimulation applied to the user's body in response to the indicated pressure, or, in the instance of a plurality of pressures sensors, pressures. Controller 501 may also cue the user to press more firmly or less firmly by visual, vibratory or auditory means. For instance controller 501 may command a particular mode of operation of the lights of the invention, the vibration means of the invention, or may cause sounds to emanate from speaker 876.

Description of the Operating Modes and Programmable Elements of the Invention

Exemplary modes of operation and control of the states and patterns used to operate the vibrators and light sources of the invention are now discussed. While a preferred embodiment is discussed for purpose of description herein, it is to be understood that the programmable nature of the invention allows any variation, and therefore any pattern, of intensity and wave shape for both the light sources and vibration of the invention. Thus, the embodiment shown is exemplary only. The intensity of vibration of clitoral vibrator 304 and vaginal vibrator 204 may be controlled by pulse width modulation (PWM) control of power to the vibrator motor by controller 501, such that, for example, a 50% duty cycle represents LOW power, a 75% duty cycle represents MEDIUM power, and a 100% duty cycle represents HIGH power. These designations of power level may be set as desired, such that various terms may be given to corresponding duty cycles, and any number of power levels, which are the result of variation of the pulse width of the PWM drive signal driving the vibrators, may be defined as desired. It is a feature of controller 501 that any of the vibrators of the invention may be driven at any duty cycle desired, whether constant or in a pattern such as a pulsed pattern, sinusoidal pattern, or otherwise, based upon the desire of the user as programmed into controller 501, and, preferably, stored into memory 502.

A user may depress the depressible buttons 405-409 on keypad 403 to control operation of the invention in the following manner. It is to be understood that, due to the programmable nature of the invention, any combination of vibration patterns and light patterns may be programmed into controller 501 and memory 502. The modes of operation described hereinbelow are exemplary and not limiting. In the exemplary embodiment used in for description of operating modes below, vaginal light source group 202 comprises "blue" LEDs, "red" LEDs and an infrared LED; and likewise clitoral light source group 302 comprises "blue" LEDs, "red" LEDs and an infrared LED. Again, these configurations of light source groups are merely exemplary. Furthermore, in the exemplary embodiment used in for description of operating modes below, vaginal finger 200 comprises a vaginal vibrator 204 and clitoral finger 300 comprises clitoral vibrator 304.

In the exemplary embodiment shown in figures and described herein, the invention may be powered on by pressing first depressible control button 405 and third depressible control button 407 simultaneously for three seconds, which may power the invention ON in a base operating mode. In this mode, vaginal vibrator 204 operates in a continuous LOW power state; the blue, red and infrared LEDs of vaginal light source group 202 are powered in the base pattern depicted in FIG. 9; clitoral vibrator 304 operates in a LOW power state; and the blue, red and infrared LEDs of clitoral light source group 302 are also powered in the base pattern depicted in FIG. 9. Next, pressing and releasing second depressible control button 406 may cause controller 501 to command clitoral vibrator 304 and the light sources of clitoral light source group 302 to an OFF state. Next, pressing and releasing second depressible button 406 may cause controller 501 to command clitoral vibrator 304 to a continuous LOW power state, and cause the light sources of clitoral light source group 302 to operate in the base pattern state of FIG. 9, while commanding vaginal vibrator 204 and the light sources of vaginal light source group 202 to an OFF state. Next, pressing and releasing second depressible button 406 may cause controller 501 to command vaginal vibrator 204 and clitoral vibrator 304 to pulse between OFF and ON states in an out-of-phase pattern in LOW power mode, while commanding the light sources of both vaginal light source group 202 and clitoral light source group 302 to operate in the base pattern shown in FIG. 9. Next, pressing and releasing second depressible button 406 may cause controller 501 to command vaginal vibrator 204 and clitoral vibrator 304 to pulse between OFF and ON states in an in-phase pattern with a high pulse rate, such as, for example, greater than 2.0 Hz pulse rate, in LOW power mode, while light source groups 202 and 302 remain operating in the base pattern shown in FIG. 9. It is to be understood that the pulse rate may be any rate commanded by controller 501. Next, pressing and releasing second depressible button 406 may cause controller 501 to command vaginal vibrator 204 and clitoral vibrator 304 to operate in a substantially sinusoidal-shaped intensity profile, in which the PWM signal driving each vibrator is characterized by a pulse width that varies sinusoidally. Next, pressing and releasing second depressible button 406 may cause controller 501 to command vaginal vibrator 204 and clitoral vibrator 304, and light source groups 202 and 302, back into the base operating mode described above in which vaginal vibrator 204 operates in a continuous LOW power state; the blue, red and infrared LEDs of vaginal light source group 202 are powered in the base pattern depicted in FIG. 9; clitoral vibrator 304 operates in a continuous LOW power state; and the blue, red and infrared LEDs of clitoral light source group 302 are also powered in the base pattern depicted in FIG. 9.

Continuing to discuss now the exemplary mode of operation described above, when the invention is in the base operating mode, pressing third depressible control button 407 alone causes controller 501 to command vaginal vibrator 204 and clitoral vibrator 304 to increase intensity by commanding a higher duty cycle as hereinbefore described, and pressing third depressible control button 407 again causes controller 501 to command vaginal vibrator 204 and clitoral vibrator 304 to further increase intensity. Each press may, for example, result in an increase of $\frac{1}{6}^{th}$ of intensity range until maximum intensity is reached. Thus, in the exemplary base operating mode described herein, pressing third depressible control button 407 generally results in an increase in perceived vibration intensity to the user. Likewise, when the invention is in the base operating mode, pressing first depressible control button 405 alone causes controller 501 to command vaginal vibrator 204 and clitoral vibrator 304 to decrease intensity by commanding a lower duty cycle. Thus, in the exemplary base operating mode described herein, pressing first depressible control button 405 generally results in a decrease in perceived vibration intensity to the user. In this manner the user may select a desired intensity of vibration. Any number of vibration intensity levels may be programmed into controller 501 and memory 502.

Figure 9:
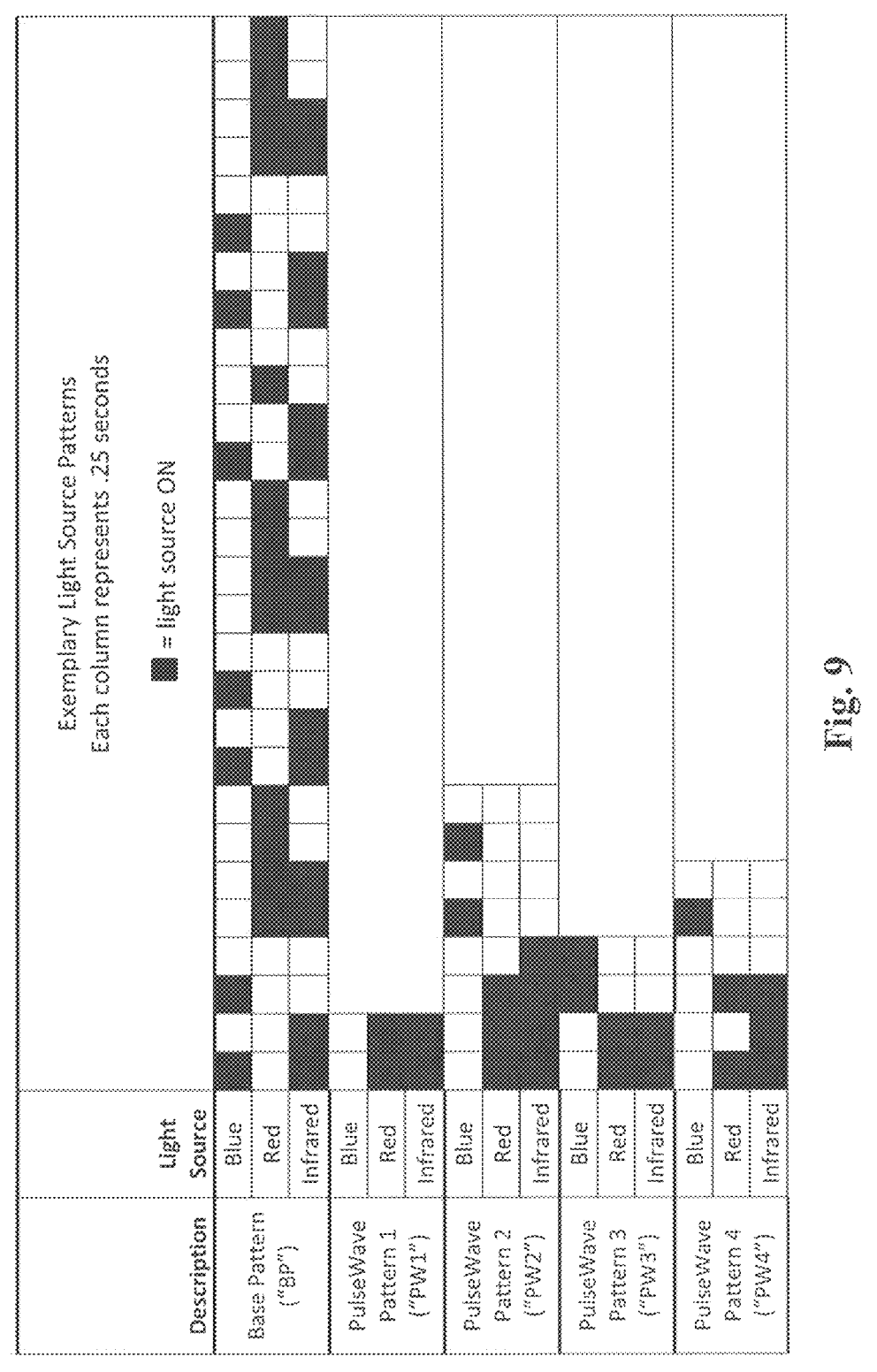

Continuing to discuss now the exemplary mode of operation described above, when the invention is in the base operating mode, depressing and holding fifth depressible control button 409 may cause controller 501 to command vaginal vibrator 204 and clitoral vibrator 304 and the light sources of light source groups 202 and 302 to cycle through a series of programmed states which may include, for the vibrators: continuous ON in LOW power state, continuous OFF state, pulsed ON and OFF in both in-phase and out-of-phase states; and sinusoidal in both in-phase and out-of-phase states; and, for the light source groups 202 and 302: continuous ON state for all light sources, continuous OFF state for all light sources, the base pattern and other patterns shown in FIG. 9. The invention may cycle through each of these states in series as programmed into controller 501 and memory 502, taking, for example, approximately seven minutes to complete the cycle. The length of time of the cycle may be programmable, as is the sequencing and description of the states of the vibrators and light sources. Pressing any button during the cycle may return the invention to the base operating mode. An exemplary preferred program of light energy and motor stimulation is shown in FIGS. 9 and 10.

Continuing to discuss now the exemplary mode of operation described above, when the invention is in the base operating mode, pressing first depressible control button 405 and third depressible control button 407 simultaneously for three seconds may cause controller 501 to command vaginal vibrator 204 and clitoral vibrator 304 to an OFF state, and likewise commend all light sources of vaginal light source group 202 and clitoral light source group 302 to an OFF state.

It is to be noted that pulse width of the PWM drive signal to the vibrators of the invention may be varied independently of one another by controller 501 in any pattern desired such as, for example, continuous ON, continuous OFF, sinusoidal, square, ramped, and so on, by modulation of the pulse width of the PWM drive signal. Also, as herein used, "in-phase" means that the PWM signal to vaginal vibrator 204 and clitoral vibrator 304 are of like waveform with substantially identical timing "Out-of-phase" means that the PWM signal to vaginal vibrator 204 and clitoral vibrator 304 are of like waveform but are substantially 180 degrees out of phase. It is further to be noted that the PWM drive signals provided to vaginal vibrator 204 and clitoral vibrator 304 are provided independently of one another. Thus, the PWM waveforms to vaginal vibrator 204 and clitoral vibrator 304 may take independently take any shape desired.

Referring now to FIG. 9, and keeping with the exemplary embodiment used in the above description of an exemplary mode of operation of the invention, the timing of various exemplary light source patterns are depicted to provide further detail as to the variety of patterns of light energy emission that may be programmed into controller 501 and memory 502. It can readily be seen that the pattern defined as Base Pattern, for example, causes the blue and infrared LEDs of a light source group to turn ON for 0.25 seconds, after which the blue LED turns OFF for 0.25 seconds while the infrared LED remains ON, and so on. In this manner any number of light source patterns may be defined and programmed into controller 501. Once the patterns have run their course they may repeat. In the examples shown in FIG. 9, five light source patterns are depicted for the exemplary case in which a light source group comprises blue LEDs, red LEDs, and infrared LEDs, in keeping with the exemplary embodiment used in the description of the exemplary mode of operation above. The five exemplary patterns depicted in FIG. 9 are Base Pattern ("BP"); PulseWave Pattern 1 ("PW1"); PulseWave Pattern 2 ("PW2"); PulseWave Pattern 3 ("PW3"); and PulseWave Pattern 4 ("PW4"). Once such patterns are defined and programmed into controller 501 and memory 502, they may be used in combination with vibrator patterns also programmed into controller 501 and memory 502 in order to define further exemplary modes of operation of the invention, as discussed below.

Referring next to FIG. 10, and keeping with the exemplary embodiment used in the above description of an exemplary mode of operation of the invention, the timing of various exemplary vibrator patterns are depicted to provide further detail as to the variety of patterns of vibration that may be programmed into controller 501 and memory 502. It can readily be seen that the pattern defined as Constant, for example, causes the vibrators to operate continuously at a constant power level. In this manner any number of vibration patterns may be defined and programmed into controller 501 and memory 502. Once the patterns have run their course they may repeat. In the examples shown in FIG. 10, six vibration patterns are depicted for the exemplary case in which the invention comprises a vaginal vibrator 204 and a clitoral vibrator 304, in keeping with the exemplary embodiment used in the description of the exemplary mode of operation above. The six exemplary vibrator patterns depicted in FIG. 10 are constant ("C"), In Phase Pulse ("IPP"), Out of Phase Pulse ("OPP"), In Phase Wave ("IPW"), Out of Phase Wave ("OPW"), and Fast Pulse ("FP"). Once such patterns are defined and programmed into controller 501 and memory 502, they may be used in combination with light source patterns also programmed into controller 501 and memory 502 in order to define further exemplary modes of operation of the invention, as discussed below.

Referring now to FIG. 11, another exemplary mode of operation is defined, consistent with the above description of an exemplary mode of operation, for the exemplary embodiment of the invention which both clitoral and vaginal light source groups 302 and 202, respectively, comprise blue LED light sources, red LED light sources, and infrared LED light sources and in which vaginal finger 200 and clitoral finger 300 comprise a vibrator. It is readily seen from FIG. 11 that in the first sixty seconds, both vaginal vibrator 204 and clitoral vibrator 304 operate in a continuous mode at LOW power while vaginal light source group 202 and clitoral light source group 302 operate in pattern PW1 as was defined in FIG. 9. After the first sixty seconds and until 180 seconds have elapsed, both vaginal vibrator 204 and clitoral vibrator 304 operate in a continuous mode at MEDIUM power while vaginal light source group 202 and clitoral light source group 302 operate in pattern PW2 as was defined in FIG. 9. After 180 seconds have elapsed and until 300 seconds have elapsed, both vaginal vibrator 204 and clitoral vibrator 304 operate in a continuous mode at MEDIUM power while vaginal light source group 202 and clitoral light source group 302 operate in pattern PW3 as was defined in FIG. 9. After 300 seconds have elapsed and until 480 seconds have elapsed, both vaginal vibrator 204 and clitoral vibrator 304 operate in a continuous mode at HIGH power while vaginal light source group 202 and clitoral light source group 302 operate in pattern PW4 as was defined in FIG. 9. After 480 seconds have elapsed, both vaginal vibrator 204 and clitoral vibrator 304 operate in a continuous mode at MEDIUM power while vaginal light source group and clitoral light source group operate in pattern PW4 as was defined in FIG. 9. In this exemplary mode of operation, the invention will continue to run in this state until the user powers the invention to an OFF state as defined above, or presses any button which returns the invention to base motor and light patterns, in an alternate embodiment, the invention may time out after a set period of time.

It is not necessary that the vibrators and light sources of the invention operate in the same pattern at the same time; in fact, the great majority of vibrator and light source patterns may comprise different patterns for the vibrators and light sources of the invention as they are all controlled individually by controller 501. It is thus readily seen that any pattern of operation of vibration and light source patterns may be programmed into controller 501 and computer readable non-transitory memory 502.

Methods of Using the Invention

One exemplary method of the invention may comprise the following steps: applying lubrication, a lubricating light coupling agent or a combination of such agents as desired to vaginal finger 200, slidingly engaging vaginal finger 200 in a vagina while resting urethral protuberance 600 on or near the external urethral meatus, turning the vaginal light source group 202 of the apparatus ON, turning the vaginal vibrator 204 of the apparatus ON, and holding and applying movement as desired by grasping handle 400. Alternatively, light source groups and or vibrator may be turned on prior to contact of finger to body tissue. The invention may further comprise control circuitry located in the handle 400 of the invention which may be used to operate the invention in one or more of many possible operational modes which are discussed further herein. Keypad 403 may cover the internal circuitry of the invention in such a manner as to provide environmental protection for the circuitry while at the same time allowing a user to control the operation of the invention by pressing on keypad 403 which is in physical contact with and engages switches 500 in electrical communication with the control circuitry. In normal use, handle 400 remains outside the body of the user.

Figure 22:
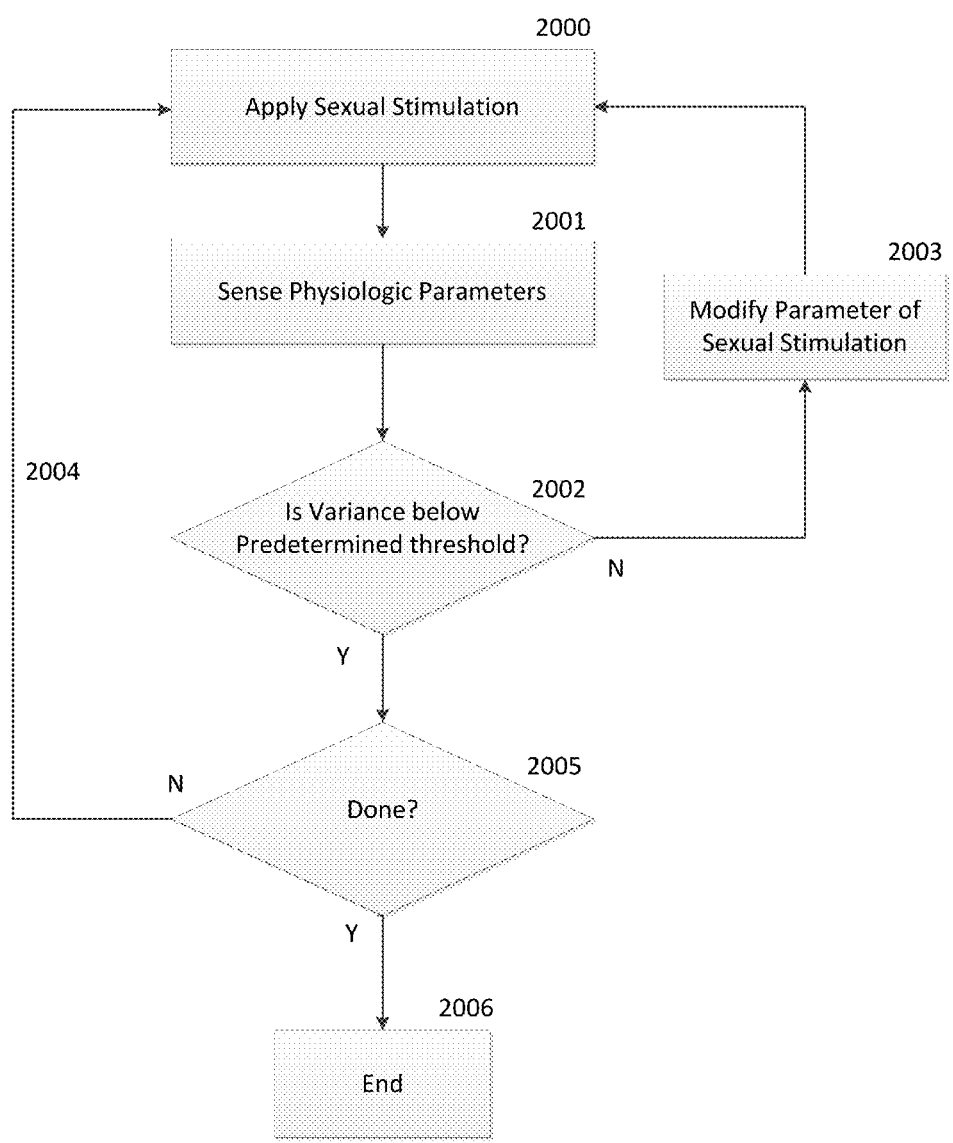
FIG. 22 depicts a flow chart of a method of the invention in which at least one physiologic sensor provides physiologic parameter information which is compared against a predetermined physiologic parameter value, resulting in a variance, and where the variance is compared against a threshold for determining changes to be made to parameters of sexual stimulation in order to achieve a desired effect of sexual stimulation to a user.

Referring now to FIG. 22, a flow chart of a method of the invention is depicted. In initial stimulation step 2000, sexual stimulation is applied to a user of the invention, in any aforementioned manner. Thus, mechanical stimulation and/or light stimulation may be applied to the user in any combination, level of intensity, or pattern. For example, mechanical stimulation in the form of vibration may be applied to an area near the Graffenberg Spot of a user while mechanical stimulation in the form of vibration may be applied to the clitoris of a user. Light stimulation may be applied to an area near the Graffenberg Spot of a user at the same time as the mechanical vibration, and likewise light stimulation may be applied to the clitoris of a user at the same time. Initial stimulation step 2000 may comprise any combination of sexual stimulation methods, within any range of parameters taught herein. As the initial sexual stimulation of step 2000 is applied to a user, at least one, but preferably, a plurality of physiologic sensors sense the physiologic parameters while the user is being sexually stimulated in step 2001. The physiologic sensors provide physiological information in the form of signals to controller 501 of the invention (not shown in FIG. 22). In step 2002, controller 501 may execute instructions comparing the physiological information provided by physiologic sensors to at least one predetermined physiologic state parameter value to arrive at a variance between the sensed physiologic parameter and the predetermined physiologic parameter value. Said predetermined desired physiologic parameter value may, for example, be stored in non-transitory computer readable memory 502. For instance, the predetermined desired physiologic parameter value may be a predetermined heart rate, a predetermined blood oxygenation level, or a predetermined level of electromyographic activity. If the variance is below a predetermined threshold, "Y" of step 2002, and if the user has not completed the sexual activity "N" of step 2005, then the applied sexual stimulation is continued, and the process repeats. If the variance is above a predetermined threshold, "N" of step 2002, Controller 501 may execute a sequence of computer readable instructions stored in non-transitory computer readable memory 502, which results in the changing of the parameters of the sexual stimulation being applied to the user in step 2003. After the parameters of the sexual stimulation being applied to the user are changed, the process repeats: if the changes to the parameters of the sexual stimulation being applied to the user result in an increase in the variance, controller 501 may execute a sequence of computer readable instructions stored in non-transitory computer readable memory 502, which results in further changing of the parameters of the sexual stimulation being applied to the user 2003, and so on, until the variance is below the predetermined threshold. Once the user has completed the sexual activity, the method may be ended step 2006. It can be seen that any number of predetermined physiologic parameters, of various types, may be stored in non-transitory computer readable memory 502; and likewise any number of sensed physiologic parameters may be sensed by the physiologic sensors of the invention. The variance may be a variance between a single sensed physiologic parameter value and a predetermined physiologic parameter value; or the variance may comprise a combination of sensed physiologic parameter values and predetermined physiologic parameter values of any quantity and any physiologic parameter type.

Still referring to FIG. 22, knowledge of the changes to the physiologic parameters during the various phases of sexual stages sexual response cycle may be used to determine the predetermined physiologic parameter values that are used in arriving at the variance. These physiologic parameters may be individualized to a particular user by the user inputting information into the invention through, for example, keypad 403 (not shown in FIG. 22) as the user experiences various phases of the sexual response cycle. For instance, as a user experiences various phases of the sexual response cycle they may press a button or buttons on keypad 403, whereupon controller 501 may cause computer readable non transitory memory 502 to store the physiologic parameter information being provided at that time by the physiological sensors of the invention. In this manner, the invention may utilize physiologic parameter values for a particular user, and may therefore change the sexual stimulation applied to the user in step 2003 to achieve physiological parameters for a particular user.

Alternatively, the predetermined physiological parameter values may originate from any source. For example, survey, statistical, or other information may be used to determine the predetermined physiologic parameters that are used in calculating the variance.

Although a detailed description of the preferred and alternate embodiments as provided in the description and drawings contains many specifics for the purposes of illustration, a person of ordinary skill in the art will appreciate that many variations and alterations to the details are within the scope of the invention. Accordingly, the preferred and alternate embodiments of the invention are set forth without any loss of generality to, and without imposing limitations upon, the claimed invention. Thus the scope of the invention should be determined by the appended claims and their legal equivalents, and not merely by the preferred examples or embodiments given.

INDUSTRIAL APPLICABILITY

The improved sexual stimulation device using light therapy and vibration of the invention presents a novel and unique structure, not heretofore found in the prior art, which combines vibrational energy and light energy to improve vaginal and clitoral blood flow such that the experience of a user of the invention is enhanced over the devices of the prior art. In the present invention, physiological sensors may sense physiologic parameters of a user and to provide signals representing the sensed physiologic parameters to a controller, whereupon the controller may use the signals representing the sensed physiologic parameters to control at least one parameter of sexual stimulation applied to a user by the invention. Additional benefits may include improved blood supply to genitals and a decrease in both pathogenic bacteria and fungi. The improved sexual stimulation device using light therapy and vibration of the invention has direct applicability to the adult toy industry and related markets, and represents a significant improvement in the state of the art of adult pleasure objects.

What is claimed is:

1. A sexual stimulation device, comprising:
a vaginal finger portion having a first mechanical stimulation means; and
a handle portion having a power source and a controller disposed therein;
wherein said handle portion comprises a keypad in communication with said controller, and wherein said controller is adapted to receive commands for entering into modes of operation by a user's operation of said keypad;
wherein said vaginal finger portion and said handle portion are in communication forming a structure configured such that when said vaginal finger portion is slidingly engaged with and inserted into a vagina of said user, said handle portion remains outside said vagina; and
wherein said controller is in electrical communication with said first mechanical stimulation means and said power source, and wherein said controller is adapted to receive power from said power source, and wherein said controller is further adapted to control operation of said first mechanical stimulation means; and
wherein said vaginal finger portion is defined as an elongated shape having a longitudinal axis and having a first end and a second end wherein said vaginal finger portion first end is adapted to be inserted into said vagina and said vaginal finger portion second end is in communication with said handle portion;
wherein said controller is adapted to compare a sensed physiologic parameter from a physiologic sensor with a predetermined physiologic parameter for determining a variance between said sensed physiologic parameter and said predetermined physiologic parameter, and for controlling said first mechanical simulation means to achieve a desired sexual stimulation effect in said user; and
wherein said sexual stimulation device further comprises said physiologic sensor in communication with said controller, wherein said physiologic sensor is disposed in said vaginal finger portion.

2. The sexual stimulation device of claim 1, wherein said vaginal finger portion further comprises a first light source group wherein said first light source group comprises at least one light source adapted to emit vaginal light energy from said vaginal finger portion.

3. The sexual stimulation device of claim 2, wherein said vaginal finger portion further comprises a mark, said mark located on said vaginal finger portion such that said vaginal light energy impacts the user's body in an area of the Graffenberg Spot of said user when said vaginal finger portion is slidingly engaged with and inserted into the vagina of said user and when said mark is just visible outside the user's vagina.

4. The sexual stimulation device of claim 1, wherein said physiologic sensor is selected from the group consisting of a pulse oximeter, an electromyography sensor and a pressure sensor.

5. The sexual stimulation device of claim 2, wherein said physiologic sensor is selected from the group consisting of a pulse oximeter, an electromyography sensor and a pressure sensor.

6. The sexual stimulation device of claim 2 wherein said vaginal light energy emitted by said first light source group is between 400 nm and 1000 nm in wavelength.

7. The sexual stimulation device of claim 5 wherein said pulse oximeter is further defined as being in a mechanical housing that is separate from any of said vaginal finger portion and said handle portion, and is in sensing contact with the skin of the user's body.

8. The sexual stimulation device of claim 7, wherein said pulse oximeter is further configured to be clipped onto an ear of the user.

9. A sexual stimulation device, comprising:
a vaginal finger portion having a first mechanical stimulation means; and
a handle portion having a power source and a controller disposed therein;
wherein said handle portion comprises a keypad in communication with said controller, and wherein said controller is adapted to receive commands for entering into modes of operation by a user's operation of said keypad;
wherein said vaginal finger portion and said handle portion are in communication forming a structure configured such that when said vaginal finger portion is slidingly engaged with and inserted into a vagina of said user, said handle portion remains outside said user's vagina; and
wherein said controller is in electrical communication with said first mechanical stimulation means and said power source, and wherein said controller is adapted to receive power from said power source and wherein said controller is further adapted to control operation of said first mechanical stimulation means; and
wherein said vaginal finger portion is defined as an elongated shape having a longitudinal axis and having a first end and a second end wherein said vaginal finger portion first end is adapted to be inserted into said vagina of said user and said vaginal finger portion second end is in communication with said handle portion; and
wherein said sexual stimulation device further comprises at least one physiologic sensor in communication with said controller, wherein said at least one physiologic sensor is selected from the group consisting of a pulse oximeter and an electromyography sensor and is disposed in said handle portion;

wherein said controller is adapted to compare a sensed physiologic parameter from said at least one physiologic sensor with a predetermined physiologic parameter for determining a variance between said sensed physiologic parameter and said predetermined physiologic parameter, and for controlling said first mechanical simulation means to achieve a desired sexual stimulation effect in said user.

10. The sexual stimulation device of claim 9, wherein said vaginal finger portion further comprises a first light source group wherein said first light source group comprises at least one light source adapted to emit vaginal light energy from said vaginal finger portion.

11. The sexual stimulation device of claim 10, wherein said vaginal finger portion further comprises a mark, said mark located on said vaginal finger portion such that said vaginal light energy impacts the user's body in an area of the Graffenberg Spot of said user when said vaginal finger portion is slidingly engaged with and inserted into the vagina of said user and when said mark is just visible outside the user's vagina.

* * * * *